US012637470B2

(12) United States Patent
Zhang et al.

(10) Patent No.: US 12,637,470 B2
(45) Date of Patent: May 26, 2026

(54) SALTS OF NITROGEN-CONTAINING HETEROCYCLIC COMPOUND, AND SOLID FORMS OF SALTS, PHARMACEUTICAL COMPOSITION AND USE THEREOF

(71) Applicant: Wuhan Humanwell Innovative Drug Research And Development Center Limited Company, Wuhan Hubei (CN)

(72) Inventors: Xuejun Zhang, Wuhan Hubei (CN); Yang Yue, Wuhan Hubei (CN); Sijun Lei, Wuhan Hubei (CN); Qingfeng Xia, Wuhan Hubei (CN); Yuan Li, Wuhan Hubei (CN); Qiongfeng Yang, Wuhan Hubei (CN); Min'an Liu, Wuhan Hubei (CN); Shaoxia Yang, Wuhan Hubei (CN); Ming Liu, Wuhan Hubei (CN); Bin Hu, Wuhan Hubei (CN); Shoubo Zhang, Wuhan Hubei (CN); Xiaohua Ding, Wuhan Hubei (CN); Zhe Liu, Wuhan Hubei (CN)

(73) Assignee: WUHAN HUMANWELL INNOVATIVE DRUG RESEARCH AND DEVELOPMENT CENTER LIMITED Company, Wuhan City (CN)

( * ) Notice: Subject to any disclaimer, the term of this patent is extended or adjusted under 35 U.S.C. 154(b) by 611 days.

(21) Appl. No.: 18/018,761

(22) PCT Filed: Jul. 28, 2021

(86) PCT No.: PCT/CN2021/108940
§ 371 (c)(1),
(2) Date: Jan. 30, 2023

(87) PCT Pub. No.: WO2022/022570
PCT Pub. Date: Feb. 3, 2022

(65) Prior Publication Data

US 2023/0312582 A1 Oct. 5, 2023

(30) Foreign Application Priority Data

Jul. 28, 2020 (CN) ........................ 202010727300.5

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .................................................... C07D 487/04
See application file for complete search history.

(56) References Cited

U.S. PATENT DOCUMENTS

| | | | | |
|---|---|---|---|---|
| 12,221,449 | B2 * | 2/2025 | Zhang | A61P 19/02 |
| 2014/0200231 | A1 | 7/2014 | Beauchamp et al. | |
| 2022/0064172 | A1 | 3/2022 | Zhang et al. | |

FOREIGN PATENT DOCUMENTS

| | | | |
|---|---|---|---|
| CN | 104903327 | A | 9/2015 |
| CN | 111518101 | A | 8/2020 |
| EP | 2943494 | B1 | 2/2017 |
| JP | 2016505010 | A | 2/2016 |
| JP | 2016512254 | A | 4/2016 |
| WO | 2020156459 | A1 | 8/2020 |

OTHER PUBLICATIONS

Zhang, Cells, 2021, 10, 939 (Year: 2021).*
Blackadar World Journal of Clinical Oncology, Feb. 10, 2016; 7(1): 54-86 (Year: 2016).*
The American Cancer Society, cancer.org, Can Acute Lymphocytic Leukemia Be Prevented?, https://web.archive.org/web/20241209175137/https://www.cancer.org/cancer/types/acute-lymphocytic-leukemia/causes-risks-prevention/prevention.html, Last updated Oct. 17, 2018 (Year: 2018).*

(Continued)

*Primary Examiner* — Andrew D Kosar
*Assistant Examiner* — Phillip Matthew Rzeczycki
(74) *Attorney, Agent, or Firm* — Lei Fang, Esq.; Smith Tempel Blaha LLC

(57) ABSTRACT

Provided are salts of a compound of formula (I) having an ATX inhibitory activity. The salts comprises inorganic acid salts or organic acid salts, and solid forms of the salts, such as crystal forms. The salts of the compound of formula (I) and their crystal forms according to the present disclosure have a good solubility, stability and hygroscopicity, and are more suitable for medicinal use. Moreover, their preparation methods are simple and convenient, and are suitable for large-scale production.

(I)

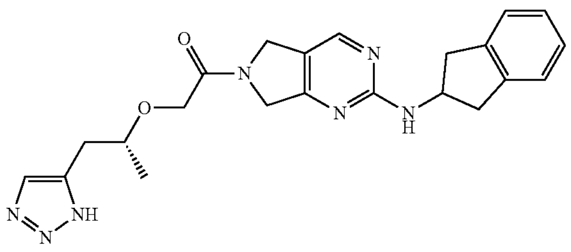

9 Claims, 22 Drawing Sheets

(56) References Cited

OTHER PUBLICATIONS

The American Cancer Society, cancer.org, Can Hodgkin Lymphoma be Prevented?, https://web.archive.org/web/20231211145704/https://www.cancer.org/cancer/types/hodgkin-lymphoma/causes-risks-prevention/prevention.html, Last updated May 1, 2018 (Year: 2018).*
Hassanpour, Journal of Cancer Research and Practice, 4, 2017, 127-129 (Year: 2017).*
Acharya, Dosage Form Design Considerations, vol. I, 2018, pp. 435-472 (Year: 2018).*
International Search Report for PCT /CN2021/108940 mailed Oct. 22, 2021. 3 pgs.
Jones. S.B. et al. Novel Autotaxin Inhibitors for the Treatment of Osteoarthritis Pain: Lead Optimization via Structure-Based Drug Design ACS Medicinal Chemistry Letters, vol. 7. No. 9. Aug. 2, 2016 (Aug. 2, 2016). pp. 1-26. especially p. 13. compound 9.
The extended European search report dated May 7, 2024 for EP App No. 21848860.9.

* cited by examiner

SALTS OF NITROGEN-CONTAINING HETEROCYCLIC COMPOUND, AND SOLID FORMS OF SALTS, PHARMACEUTICAL COMPOSITION AND USE THEREOF

CROSS-REFERENCE TO RELATED APPLICATIONS

The present disclosure is a U.S. National Application that claims priority to PCT/CN2021/108940 filed Jul. 28, 2021, which claims priority to Chinese Patent Application No. 202010727300.5 filed with the China National Intellectual Property (CNIPA) on Jul. 28, 2020, the entirety of these disclosures are incorporated herein by reference.

TECHNICAL FIELD

The present disclosure relates to the field of pharmaceutical chemistry, and particularly relates to a salt of a nitrogen-containing heterocyclic compound, and a solid form of the salt, a pharmaceutical composition and use thereof.

BACKGROUND

Autotaxin (ATX) is a secreted glycoprotein with phosphodiesterase (PDE) activity, and belongs to a member of the ectonucleotide pyrophosphatase/phosphodiesterase (ENPP) family and is therefore also known as ENPP2. ATX further has lysophospholipase D (LysoPLD) activity, and is capable of hydrolyzing lysophosphatidylcholine (LPC) to lysophosphatidic acid (LPA) with biological activity. LPA is an intracellular lipid mediator that affects many biological and biochemical processes. Studies have shown that under pathological conditions, inhibition of ATX can reduce LPA levels, thereby providing therapeutic benefits to unmet clinical demands, including cancer, lymphocyte homing, chronic inflammation, neuropathic pain, fibrosis, thrombosis, cholestatic pruritus, or fibrosis diseases induced, mediated and/or propagated by increased LPA levels and/or ATX activation. It has now been found that ATX inhibitors may be used to treat diseases associated with increased LPA levels, including cancer, lymphocyte homing, chronic inflammation, neuropathic pain, fibrosis, thrombosis, cholestatic pruritus, and fibrosis diseases, such as idiopathic pulmonary fibrosis (IPF).

The Chinese Patent Application No. 202010074393.6 describes a compound of formula (I) having an ATX inhibitory activity:

(I)

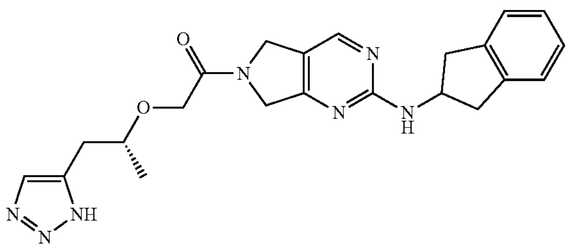

The chemical name of the compound of formula (I) is (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one. On the basis of the good biological activity of the compound, it is necessary to develop a suitable salt form and a solid form thereof so as to obtain improved druggability or other properties.

SUMMARY

In order to solve the above technical problems, the present disclosure provides a salt of a compound of formula (I) or a solid form of the salt:

(I)

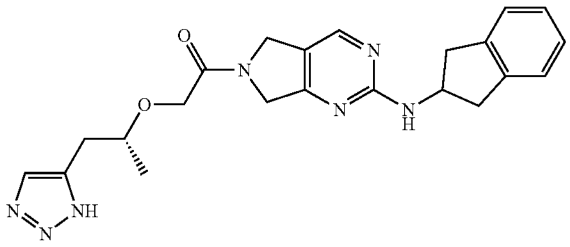

wherein the salt is selected from an inorganic acid salt or an organic acid salt; and the solid form may be a crystal form or an amorphous form.

According to an embodiment of the present disclosure, the inorganic acid salt is a salt formed from a compound of formula (I) and an inorganic acid. Preferably, the inorganic acid is selected from one or more of the following: hydrochloric acid, sulfuric acid, phosphoric acid and hydrobromic acid.

According to an embodiment of the present disclosure, the inorganic acid salt includes, but is not limited to, one or more selected from the following salts of the compound of formula (I): hydrochloride, sulfate, phosphate, hydrobromide and the like.

According to an embodiment of the present disclosure, the organic acid salt is a salt formed from a compound of formula (I) and an organic acid. Preferably, the organic acid is selected from one or more of the following: aspartic acid, maleic acid, glutamic acid, mucic acid, tartaric acid, fumaric acid, citric acid, glycolic acid, malic acid, hippuric acid, lactic acid, ascorbic acid, succinic acid, adipic acid, sebacic acid, lauric acid, p-toluenesulfonic acid, methanesulfonic acid, benzenesulfonic acid, benzoic acid and nicotinic acid.

According to an embodiment of the present disclosure, the organic acid salt includes, but is not limited to, one or more selected from the following salts of the compound of formula (I): aspartate, maleate, glutamate, mucate, tartrate, fumarate, citrate, glycolate, malate, hippurate, lactate, ascorbate, succinate, adipate, sebacate, laurate, p-toluenesulfonate, methanesulfonate, benzenesulfonate, benzoate, nicotinate and the like.

According to an exemplary embodiment of the present disclosure, the salt is selected from the hydrochloride, the fumarate or the benzenesulfonate of the compound of formula (I).

According to an embodiment of the present disclosure, the compound of formula (I) and the salt-forming acid (e.g., inorganic acid or organic acid) in the salt may be in a molar ratio of 1:(0.5-2), for example, 1:(0.5-1).

According to an embodiment of the present disclosure, the crystal form may be selected from solid forms of the following salts of the compound of formula (I): hydrochloride (1:1), sulfate (1:1), maleate (1:1), phosphate (1:1), tartrate (1:1), fumarate (1:1), citrate (1:1), glycolate (1:0.5), succinate (1:(0.5-1)), adipate (1:1), sebacate (1:1), p-toluenesulfonate (1:1), benzenesulfonate (1:1) and hydrobromide (1:1), for example, the crystal forms or the amorphous forms thereof; wherein the ratio indicated in parentheses after each salt is a molar ratio of the compound of formula (I) to the corresponding acid in the salt. In the context of the present disclosure, when the salts are mentioned, they all have molar ratios indicated in parentheses.

According to an embodiment of the present disclosure, the crystal form may be selected from crystal forms of the following salts of the compound of formula (I): crystal form A of hydrochloride, crystal form A of sulfate, crystal form A of maleate, crystal form A of phosphate, crystal form A of tartrate, crystal form B of tartrate, crystal form C of tartrate, crystal form A of fumarate, crystal form A of citrate, crystal form A of glycolate, crystal form A of succinate, crystal form B of succinate, crystal form B of adipate, crystal form A of sebacate, crystal form A of p-toluenesulfonate, crystal form A of benzenesulfonate, crystal form A of hydrobromide or crystal form B of hydrobromide, for example, selected from the crystal form A of hydrochloride, the crystal form A of fumarate or the crystal form A of benzenesulfonate of the compound of formula (I).

In the context of the present disclosure, unless otherwise stated, an error range for 2θangle values in X-ray powder diffraction (XRPD) data is ±0.2°.

According to an embodiment of the present disclosure, the crystal form A of hydrochloride has characteristic peaks in an X-ray powder diffraction pattern using Cu-Kα radiation at the following 2θangles: 7.48±0.20°, 13.13±0.20°, 16.47±0.20° and 23.94±0.20°.

According to an embodiment of the present disclosure, the crystal form A of hydrochloride has characteristic peaks in an X-ray powder diffraction pattern at the following 2θ angles: 7.48±0.20°, 13.13±0.20°, 16.47±0.20°, 18.29±0.20°, 19.89±0.20° and 23.94±0.20°.

According to an embodiment of the present disclosure, the crystal form A of hydrochloride has characteristic peaks in an X-ray powder diffraction pattern at the following 2θ angles: 7.48±0.20°, 13.13±0.20°, 14.86±0.20°, 16.47±0.20°, 18.29±0.20°, 19.89±0.20°, 23.94±0.20° and 26.92±0.20°. According to an embodiment of the present disclosure, the 2θ diffraction angle, D-value and/or relative intensity of the X-ray powder diffraction pattern using Cu-Kα radiation by the crystal form A of hydrochloride are shown in Table 1 below:

TABLE 1

XRPD diffraction peak data for the crystal form A of hydrochloride

| No. | Position [°2θ] | D-spacing [A] | Relative intensity [%] |
|---|---|---|---|
| 1 | 7.48 | 11.82 | 100.00 |
| 2 | 13.13 | 6.75 | 20.03 |
| 3 | 14.86 | 5.96 | 8.50 |
| 4 | 16.47 | 5.38 | 22.61 |
| 5 | 18.29 | 4.85 | 9.69 |
| 6 | 19.89 | 4.46 | 15.94 |
| 7 | 23.94 | 3.72 | 21.43 |
| 8 | 26.92 | 3.31 | 8.86 |

According to an embodiment of the present disclosure, the crystal form A of hydrochloride has an X-ray powder diffraction pattern substantially as shown in FIG. 1.

According to an embodiment of the present disclosure, the crystal form A of hydrochloride has one, two, three or four of the following characteristics:

(1) the TGA curve of the crystal form A of hydrochloride having a weight loss of about 2.83% at 150.0±3° C.;

(2) the DSC curve of the crystal form A of hydrochloride having a starting point of an endothermic peak at 163.5±3° C.;

(3) the DSC curve of the crystal form A of hydrochloride having an endothermic peak at 170.9±10° C.; particularly, the DSC curve of the crystal form A of hydrochloride having an endothermic peak at 170.9±5° C.; and (4) the DVS curve of the crystal form A of hydrochloride having a vapor sorption of less than about 10%, such as less than about 5%, particularly less than about 3.85% at 0% RH to 80% RH.

According to an embodiment of the present disclosure, the crystal form A of hydrochloride has one, two or three of the following characteristics:

(1) the crystal form A of hydrochloride having a TGA curve substantially as shown in FIG. 20;

(2) the crystal form A of hydrochloride having a DSC curve substantially as shown in FIG. 20; and (3) the crystal form A of hydrochloride having a DVS curve substantially as shown in FIG. 37.

According to an embodiment of the present disclosure, the crystal form A of sulfate has characteristic peaks in an X-ray powder diffraction pattern using Cu-Kα radiation at the following 2θ angles: 5.49±0.20°, 15.88±0.20°, 17.48±0.20° and 22.40±0.20°.

According to an embodiment of the present disclosure, the crystal form A of sulfate has characteristic peaks in an X-ray powder diffraction pattern at the following 2θ angles: 5.49±0.20°, 6.93±0.20°, 11.08±0.20°, 15.88±0.20°, 17.48±0.20°, 20.82±0.20° and 22.40±0.20°.

According to an embodiment of the present disclosure, the 2θ diffraction angle, D-value and/or relative intensity of the X-ray powder diffraction pattern using Cu-Kα radiation by the crystal form A of sulfate are shown in Table 2 below:

TABLE 2

XRPD diffraction peak data for the crystal form A of sulfate

| No. | Position [°2θ] | D-spacing [A] | Relative intensity [%] |
|---|---|---|---|
| 1 | 5.49 | 16.09 | 100.00 |
| 2 | 6.93 | 12.76 | 7.65 |
| 3 | 11.08 | 7.99 | 8.82 |
| 4 | 15.88 | 5.58 | 23.79 |
| 5 | 17.48 | 5.07 | 10.35 |
| 6 | 20.82 | 4.27 | 8.15 |
| 7 | 22.40 | 3.97 | 9.65 |

According to an embodiment of the present disclosure, the crystal form A of sulfate has an X-ray powder diffraction pattern substantially as shown in FIG. 2.

According to an embodiment of the present disclosure, the crystal form A of sulfate has one, two or three of the following characteristics:

(1) the TGA curve of the crystal form A of sulfate having a weight loss of about 3.53% at 150.0±3° C.;

(2) the DSC curve of the crystal form A of sulfate having a starting point of an endothermic peak at 131.8±3° C.; and (3) the DSC curve of the crystal form A of sulfate having an endothermic peak at 141.9±10° C.; particularly, the DSC curve of the crystal form A of sulfate having an endothermic peak at 141.9±5° C.

According to an embodiment of the present disclosure, the crystal form A of sulfate has one or two of the following characteristics:

(1) the crystal form A of sulfate having a TGA curve substantially as shown in FIG. 21; and (2) the crystal form A of sulfate having a DSC curve substantially as shown in FIG. 21.

According to an embodiment of the present disclosure, the crystal form A of maleate has characteristic peaks in an X-ray powder diffraction pattern using Cu-Kα radiation at the following 2θ angles: 4.43±0.20°, 13.86±0.20°, 14.41±0.20°, 15.00±0.20°, 22.07±0.20°, 22.65±0.20°, 25.58±0.20° and 27.34±0.20°.

According to an embodiment of the present disclosure, the crystal form A of maleate has characteristic peaks in an X-ray powder diffraction pattern at the following 2θ angles: 4.43±0.20°, 9.92±0.20°, 13.86±0.20°, 14.41±0.20°, 15.00±0.20°, 17.82±0.20°, 22.07±0.20°, 22.65±0.20°, 25.58±0.20° and 27.34±0.20°.

According to an embodiment of the present disclosure, the crystal form A of maleate has characteristic peaks in an X-ray powder diffraction pattern at the following 2θ angles: 4.43±0.20°, 9.92±0.20°, 13.86±0.20°, 14.41±0.20°, 15.00±0.20°, 17.82±0.20°, 22.07±0.20°, 22.65±0.20°, 24.20±0.20°, 24.53±0.20°, 25.58±0.20°, 25.84±0.20° and 27.34±0.20°.

According to an embodiment of the present disclosure, the 2θ diffraction angle, D-value and/or relative intensity of the X-ray powder diffraction pattern using Cu-Kα radiation by the crystal form A of maleate are shown in Table 3 below:

TABLE 3

XRPD diffraction peak data for the crystal form A of maleate

| No. | Position [°2θ] | D-spacing [A] | Relative intensity [%] |
|---|---|---|---|
| 1 | 4.43 | 19.96 | 45.39 |
| 2 | 9.92 | 8.91 | 15.60 |
| 3 | 12.64 | 7.01 | 3.20 |
| 4 | 13.33 | 6.64 | 6.08 |
| 5 | 13.86 | 6.39 | 37.68 |
| 6 | 14.41 | 6.15 | 100.00 |
| 7 | 15.00 | 5.91 | 18.65 |
| 8 | 15.45 | 5.74 | 4.20 |
| 9 | 16.13 | 5.49 | 6.55 |
| 10 | 17.82 | 4.98 | 14.09 |
| 11 | 18.57 | 4.78 | 8.48 |
| 12 | 19.15 | 4.64 | 8.09 |
| 13 | 19.63 | 4.52 | 6.72 |
| 14 | 22.07 | 4.03 | 21.22 |
| 15 | 22.65 | 3.93 | 16.45 |
| 16 | 24.20 | 3.68 | 17.63 |
| 17 | 24.53 | 3.63 | 23.17 |
| 18 | 25.58 | 3.48 | 53.81 |
| 19 | 25.84 | 3.45 | 24.56 |
| 20 | 26.69 | 3.34 | 7.92 |
| 21 | 27.34 | 3.26 | 27.20 |
| 22 | 28.27 | 3.16 | 6.16 |
| 23 | 29.09 | 3.07 | 2.49 |
| 24 | 29.92 | 2.99 | 11.00 |
| 25 | 30.84 | 2.90 | 6.53 |
| 26 | 32.57 | 2.75 | 4.22 |
| 27 | 33.79 | 2.65 | 2.99 |
| 28 | 36.21 | 2.48 | 1.01 |

According to an embodiment of the present disclosure, the crystal form A of maleate has an X-ray powder diffraction pattern substantially as shown in FIG. 3.

According to an embodiment of the present disclosure, the crystal form A of maleate has one or two of the following characteristics:

(1) the TGA curve of the crystal form A of maleate having a weight loss of about 10.48% at 150.0±3° C.; and (2) the DSC curve of the crystal form A of maleate having two endothermic peaks at 103.0±10° C. and 132.8±10° C.; particularly, the DSC curve of the crystal form A of maleate having two endothermic peaks at 103.0±5° C. and 132.8±5° C.

According to an embodiment of the present disclosure, the crystal form A of maleate has one or two of the following characteristics:

(1) the crystal form A of maleate having a TGA curve substantially as shown in FIG. 22; and (2) the crystal form A of maleate having a DSC curve substantially as shown in FIG. 22.

According to an embodiment of the present disclosure, the crystal form A of phosphate has characteristic peaks in an X-ray powder diffraction pattern using Cu-Kα radiation at the following 2θ angles: 5.08±0.20°, 15.93±0.20°, 24.37±0.20° and 25.19±0.20°.

According to an embodiment of the present disclosure, the 2θ diffraction angle, D-value and/or relative intensity of the X-ray powder diffraction pattern using Cu-Kα radiation by the crystal form A of phosphate are shown in Table 4 below:

TABLE 4

XRPD diffraction peak data for the crystal form A of phosphate

| Position [°2θ] | D-spacing [A] | Relative intensity [%] |
|---|---|---|
| 5.08 | 17.41 | 100.00 |
| 15.93 | 5.56 | 75.29 |
| 24.37 | 3.65 | 22.44 |
| 25.19 | 3.54 | 31.38 |

According to an embodiment of the present disclosure, the crystal form A of phosphate has an X-ray powder diffraction pattern substantially as shown in FIG. 4.

According to an embodiment of the present disclosure, the crystal form A of phosphate has one or two of the following characteristics:

(1) the TGA curve of the crystal form A of phosphate having a weight loss of about 12.68% at 150.0±3° C.; and (2) the DSC curve of the crystal form A of phosphate having two endothermic peaks at 89.4±3° C. and 94.3±3° C.

According to an embodiment of the present disclosure, the crystal form A of phosphate has one or two of the following characteristics:

(1) the crystal form A of phosphate having a TGA curve substantially as shown in FIG. 23; and (2) the crystal form A of phosphate having a DSC curve substantially as shown in FIG. 23.

According to an embodiment of the present disclosure, the crystal form A of tartrate has characteristic peaks in an X-ray powder diffraction pattern using Cu-Kα radiation at the following 2θ angles: 5.00±0.20° and 15.88±0.20°.

According to an embodiment of the present disclosure, the crystal form A of tartrate has characteristic peaks in an X-ray powder diffraction pattern at the following 2θ angles: 5.00±0.20°, 7.34±0.20°, 8.59±0.20°, 15.88±0.20°, 19.54±0.20°, 21.46±0.20°, 23.43±0.20° and 25.08±0.20°.

According to an embodiment of the present disclosure, the 2θ diffraction angle, D-value and/or relative intensity of the X-ray powder diffraction pattern using Cu-Kα radiation by the crystal form A of tartrate are shown in Table 5 below:

TABLE 5

XRPD diffraction peak data for the crystal form A of tartrate

| No. | Position [°2θ] | D-spacing [A] | Relative intensity [%] |
|---|---|---|---|
| 1 | 5.00 | 17.66 | 100.00 |
| 2 | 7.34 | 12.04 | 9.51 |
| 3 | 8.59 | 10.29 | 10.07 |
| 4 | 15.88 | 5.58 | 50.13 |
| 5 | 19.54 | 4.54 | 9.72 |
| 6 | 21.46 | 4.14 | 18.23 |
| 7 | 23.43 | 3.80 | 12.44 |
| 8 | 25.08 | 3.55 | 17.21 |

According to an embodiment of the present disclosure, the crystal form A of tartrate has an X-ray powder diffraction pattern substantially as shown in FIG. 5.

According to an embodiment of the present disclosure, the crystal form A of tartrate has one or two of the following characteristics:

(1) the TGA curve of the crystal form A of tartrate having a weight loss of about 14.67% at 150.0±3° C.; and (2) the DSC curve of the crystal form A of tartrate having an endothermic peak at 96.8±10° C.; particularly, the DSC curve of the crystal form A of tartrate having an endothermic peak at 96.8±5° C.

According to an embodiment of the present disclosure, the crystal form A of tartrate has one or two of the following characteristics:

(1) the crystal form A of tartrate having a TGA curve substantially as shown in FIG. 24; and (2) the crystal form A of tartrate having a DSC curve substantially as shown in FIG. 24.

According to an embodiment of the present disclosure, the crystal form B of tartrate has characteristic peaks in an X-ray powder diffraction pattern using Cu-Kα radiation at the following 2θ angles: 5.24±0.20° and 23.94±0.20°.

According to an embodiment of the present disclosure, the 2θ diffraction angle, D-value and/or relative intensity of the X-ray powder diffraction pattern using Cu-Kα radiation by the crystal form B of tartrate are shown in Table 6 below:

TABLE 6

XRPD diffraction peak data for the crystal form B of tartrate

| Position [°2θ] | D-spacing [A] | Relative intensity [%] |
|---|---|---|
| 5.24 | 16.85 | 100.00 |
| 23.94 | 3.72 | 57.28 |

According to an embodiment of the present disclosure, the crystal form B of tartrate has an X-ray powder diffraction pattern substantially as shown in FIG. 6.

According to an embodiment of the present disclosure, the crystal form B of tartrate has one, two or three of the following characteristics:

(1) the TGA curve of the crystal form B of tartrate having a weight loss of about 4.87% at 150.0±3° C.;

(2) the DSC curve of the crystal form B of tartrate having a starting point of an endothermic peak at 173.9±3° C.; and (3) the DSC curve of the crystal form B of tartrate having an endothermic peak at 175.3±3° C.

According to an embodiment of the present disclosure, the crystal form B of tartrate has one or two of the following characteristics:

(1) the crystal form B of tartrate having a TGA curve substantially as shown in FIG. 25; and (2) the crystal form B of tartrate having a DSC curve substantially as shown in FIG. 25.

According to an embodiment of the present disclosure, the crystal form C of tartrate has characteristic peaks in an X-ray powder diffraction pattern using Cu-Kα radiation at the following 2θ angles: 4.60±0.20°, 16.15±0.20° and 18.13±0.20°.

According to an embodiment of the present disclosure, the crystal form C of tartrate has characteristic peaks in an X-ray powder diffraction pattern at the following 2θ angles: 4.60±0.20°, 7.58±0.20°, 14.39±0.20°, 16.15±0.20°, 18.13±0.20°, 22.32±0.20°, 24.44±0.20° and 26.69±0.20°.

According to an embodiment of the present disclosure, the 2θ diffraction angle, D-value and/or relative intensity of the X-ray powder diffraction pattern using Cu-Kα radiation by the crystal form C of tartrate are shown in Table 7 below:

TABLE 7

XRPD diffraction peak data for the crystal form C of tartrate

| No. | Position [°2θ] | D-spacing [A] | Relative intensity [%] |
|---|---|---|---|
| 1 | 4.60 | 19.22 | 100.00 |
| 2 | 7.58 | 11.66 | 20.06 |
| 3 | 9.35 | 9.46 | 6.16 |
| 4 | 14.39 | 6.16 | 10.45 |
| 5 | 16.15 | 5.49 | 27.62 |
| 6 | 18.13 | 4.89 | 70.29 |
| 7 | 22.32 | 3.98 | 14.92 |
| 8 | 24.44 | 3.64 | 12.08 |
| 9 | 26.69 | 3.34 | 10.11 |

According to an embodiment of the present disclosure, the crystal form C of tartrate has an X-ray powder diffraction pattern substantially as shown in FIG. 7.

According to an embodiment of the present disclosure, the crystal form A of fumarate has characteristic peaks in an X-ray powder diffraction pattern using Cu-Kα radiation at the following 2θ angles: 9.52±0.20°, 13.29±0.20°, 14.92±0.20° and 25.23±0.20°.

According to an embodiment of the present disclosure, the crystal form A of fumarate has characteristic peaks in an X-ray powder diffraction pattern at the following 2θ angles: 9.52±0.20°, 13.29±0.20°, 14.92±0.20°, 19.02±0.20°, 21.39±0.20°, 25.23±0.20° and 28.07±0.20°.

According to an embodiment of the present disclosure, the 2θ diffraction angle, D-value and/or relative intensity of the X-ray powder diffraction pattern using Cu-Kα radiation by the crystal form A of fumarate are shown in Table 8 below:

TABLE 8

XRPD diffraction peak data for the crystal form A of fumarate

| No. | Position [°2θ] | D-spacing [A] | Relative intensity [%] |
|---|---|---|---|
| 1 | 9.52 | 9.29 | 100.00 |
| 2 | 13.29 | 6.66 | 39.24 |
| 3 | 14.92 | 5.94 | 41.59 |
| 4 | 19.02 | 4.67 | 25.97 |
| 5 | 21.39 | 4.15 | 29.70 |
| 6 | 25.23 | 3.53 | 91.11 |
| 7 | 28.07 | 3.18 | 12.58 |

According to an embodiment of the present disclosure, the crystal form A of fumarate has an X-ray powder diffraction pattern substantially as shown in FIG. 8.

According to an embodiment of the present disclosure, the crystal form A of fumarate has one, two, three or four of the following characteristics:

(1) the TGA curve of the crystal form A of fumarate having a weight loss of about 3.86% at 150.0±3° C.;

(2) the DSC curve of the crystal form A of fumarate having a starting point of an endothermic peak at 208.6±3° C.;

(3) the DSC curve of the crystal form A of fumarate having an endothermic peak at 210.2±3° C.; and (4) the DVS curve of the crystal form A of fumarate having a vapor sorption of less than about 1%, such as less than about 0.8%, particularly less than about 0.60% at 0% RH to 80% RH.

According to an embodiment of the present disclosure, the crystal form A of fumarate has one, two or three of the following characteristics:

(1) the crystal form A of fumarate having a TGA curve substantially as shown in FIG. 26;

(2) the crystal form A of fumarate having a DSC curve substantially as shown in FIG. 26; and (3) the crystal form A of fumarate having a DVS curve substantially as shown in FIG. 38.

According to an embodiment of the present disclosure, the crystal form A of citrate has characteristic peaks in an X-ray powder diffraction pattern using Cu-Kα radiation at the following 2θ angles: 4.96±0.20° and 15.76±0.20°.

According to an embodiment of the present disclosure, the 2θ diffraction angle, D-value and/or relative intensity of the X-ray powder diffraction pattern using Cu-Kα radiation by the crystal form A of tartrate are shown in Table 9 below:

TABLE 9

XRPD diffraction peak data for the crystal form A of citrate

| No. | Position [°2θ] | D-spacing [A] | Relative intensity [%] |
|---|---|---|---|
| 1 | 4.96 | 17.82 | 100.00 |
| 2 | 15.76 | 5.62 | 52.29 |

According to an embodiment of the present disclosure, the crystal form A of citrate has an X-ray powder diffraction pattern substantially as shown in FIG. 9.

According to an embodiment of the present disclosure, the crystal form A of citrate has one or two of the following characteristics:

(1) the TGA curve of the crystal form A of citrate having a weight loss of about 10.24% at 150.0±3° C.; and (2) the DSC curve of the crystal form A of citrate having an endothermic peak at 91.2±5° C.; particularly, the DSC curve of the crystal form A of citrate having an endothermic peak at 91.2±3° C.

According to an embodiment of the present disclosure, the crystal form A of citrate has one or two of the following characteristics:

(1) the crystal form A of citrate having a TGA curve substantially as shown in FIG. 27; and (2) the crystal form A of citrate having a DSC curve substantially as shown in FIG. 27.

According to an embodiment of the present disclosure, the crystal form A of glycolate has characteristic peaks in an X-ray powder diffraction pattern using Cu-Kα radiation at the following 2θ angles: 5.26±0.20°, 7.27±0.20°, 14.12±0.20°, 16.02±0.20° and 24.11±0.20°.

According to an embodiment of the present disclosure, the 2θ diffraction angle, D-value and/or relative intensity of the X-ray powder diffraction pattern using Cu-Kα radiation by the crystal form A of glycolate are shown in Table 10 below:

TABLE 10

XRPD diffraction peak data for the crystal form A of glycolate

| No. | Position [°2θ] | D-spacing [A] | Relative intensity [%] |
|---|---|---|---|
| 1 | 5.26 | 16.81 | 100.00 |
| 2 | 7.27 | 12.15 | 61.43 |
| 3 | 14.12 | 6.27 | 61.90 |
| 4 | 16.02 | 5.53 | 96.56 |
| 5 | 24.11 | 3.69 | 35.48 |

According to an embodiment of the present disclosure, the crystal form A of glycolate has an X-ray powder diffraction pattern substantially as shown in FIG. 10.

According to an embodiment of the present disclosure, the crystal form A of glycolate has one or two of the following characteristics:

(1) the TGA curve of the crystal form A of glycolate having a weight loss of about 7.72% at 150.0±3° C.; and (2) the DSC curve of the crystal form A of glycolate having an endothermic peak at 103.1±15° C.; particularly, the DSC curve of the crystal form A of glycolate having an endothermic peak at 103.1±10° C.

According to an embodiment of the present disclosure, the crystal form A of glycolate has one or two of the following characteristics:

(1) the crystal form A of glycolate having a TGA curve substantially as shown in FIG. 28; and (2) the crystal form A of glycolate having a DSC curve substantially as shown in FIG. 28.

According to an embodiment of the present disclosure, the crystal form A of succinate has characteristic peaks in an X-ray powder diffraction pattern using Cu-Kα radiation at the following 2θ angles: 5.26±0.20°, 14.00±0.20°, 15.76±0.20°, 21.07±0.20°, 22.00±0.20° and 27.08±0.20°.

According to an embodiment of the present disclosure, the crystal form A of succinate has characteristic peaks in an X-ray powder diffraction pattern at the following 2θ angles: 5.26±0.20°, 6.99±0.20°, 7.35±0.20°, 14.00±0.20°, 15.76±0.20°, 21.07±0.20°, 22.00±0.20° and 27.08±0.20°.

According to an embodiment of the present disclosure, the 2θ diffraction angle, D-value and/or relative intensity of the X-ray powder diffraction pattern using Cu-Kα radiation by the crystal form A of succinate are shown in Table 11 below:

TABLE 11

XRPD diffraction peak data for the crystal form A of succinate

| No. | Position [°2θ] | D-spacing [A] | Relative intensity [%] |
|---|---|---|---|
| 1 | 5.26 | 16.80 | 100.00 |
| 2 | 6.99 | 12.65 | 25.35 |
| 3 | 7.35 | 12.03 | 25.34 |
| 4 | 14.00 | 6.33 | 17.35 |
| 5 | 15.76 | 5.62 | 35.65 |
| 6 | 16.22 | 5.47 | 13.27 |
| 7 | 21.07 | 4.22 | 19.43 |
| 8 | 22.00 | 4.04 | 81.50 |
| 9 | 26.11 | 3.41 | 5.48 |
| 10 | 27.08 | 3.29 | 20.90 |
| 11 | 32.34 | 2.77 | 8.01 |

According to an embodiment of the present disclosure, the crystal form A of succinate has an X-ray powder diffraction pattern substantially as shown in FIG. 11.

According to an embodiment of the present disclosure, the crystal form A of succinate has one or two of the following characteristics:

(1) the TGA curve of the crystal form A of succinate having a weight loss of about 3.74% at 150.0±3° C.; and (2) the DSC curve of the crystal form A of succinate having four endothermic peaks at 73.3±10° C., 102.2±10° C., 136.6±10° C. and 173.6±10° C.; particularly, the DSC curve of the crystal form A of succinate having four endothermic peaks at 73.3±5° C., 102.2±5° C., 136.6±5° C. and 173.6±5° C.

According to an embodiment of the present disclosure, the crystal form A of succinate has one or two of the following characteristics:

(1) the crystal form A of succinate having a TGA curve substantially as shown in FIG. 29; and (2) the crystal form A of succinate having a DSC curve substantially as shown in FIG. 29.

According to an embodiment of the present disclosure, the crystal form B of succinate has characteristic peaks in an X-ray powder diffraction pattern using Cu-Kα radiation at the following 2θ angles: 9.54±0.20°, 12.60±0.20°, 14.91±0.20°, 19.17±0.20°, 21.02±0.20° and 24.88±0.20°.

According to an embodiment of the present disclosure, the crystal form B of succinate has characteristic peaks in an X-ray powder diffraction pattern at the following 2θ angles: 9.54±0.20°, 12.60±0.20°, 13.28±0.20°, 14.91±0.20°, 15.20±0.20°, 19.17±0.20°, 21.02±0.20°, 24.88±0.20° and 28.15±0.20°.

According to an embodiment of the present disclosure, the crystal form B of succinate has characteristic peaks in an X-ray powder diffraction pattern at the following 2θ angles: 9.54±0.20°, 12.60±0.20°, 13.28±0.20°, 14.91±0.20°, 15.20±0.20°, 19.17±0.20°, 19.77±0.20°, 21.02±0.20°, 21.44±0.20°, 24.88±0.20°, 25.22±0.20° and 28.15±0.20°.

According to an embodiment of the present disclosure, the 2θ diffraction angle, D-value and/or relative intensity of the X-ray powder diffraction pattern using Cu-Kα radiation by the crystal form B of succinate are shown in Table 12 below:

TABLE 12

XRPD diffraction peak data for the crystal form B of succinate

| No. | Position [°2θ] | D-spacing [A] | Relative intensity [%] |
|---|---|---|---|
| 1 | 7.79 | 11.34 | 5.73 |
| 2 | 9.54 | 9.27 | 51.65 |
| 3 | 10.68 | 8.28 | 5.28 |
| 4 | 12.60 | 7.02 | 22.35 |
| 5 | 12.91 | 6.86 | 10.81 |
| 6 | 13.28 | 6.67 | 19.52 |
| 7 | 14.36 | 6.17 | 5.83 |
| 8 | 14.91 | 5.94 | 22.70 |
| 9 | 15.20 | 5.83 | 19.32 |
| 10 | 16.84 | 5.26 | 9.89 |
| 11 | 17.40 | 5.10 | 11.42 |
| 12 | 18.21 | 4.87 | 4.27 |
| 13 | 19.17 | 4.63 | 45.74 |
| 14 | 19.77 | 4.49 | 12.63 |
| 15 | 20.06 | 4.43 | 14.41 |
| 16 | 21.02 | 4.23 | 46.20 |
| 17 | 21.44 | 4.15 | 20.70 |
| 18 | 22.75 | 3.91 | 3.80 |
| 19 | 24.88 | 3.58 | 100.00 |
| 20 | 25.22 | 3.53 | 18.23 |
| 21 | 28.15 | 3.17 | 17.06 |
| 22 | 29.04 | 3.08 | 5.65 |
| 23 | 31.78 | 2.82 | 1.58 |
| 24 | 32.72 | 2.74 | 2.07 |

According to an embodiment of the present disclosure, the crystal form B of succinate has an X-ray powder diffraction pattern substantially as shown in FIG. 12.

According to an embodiment of the present disclosure, the crystal form B of succinate has one, two or three of the following characteristics:

(1) the TGA curve of the crystal form B of succinate having a weight loss of about 0.83% at 150.0±3° C.;

(2) the DSC curve of the crystal form B of succinate having a starting point of an endothermic peak at 128.8±3° C.; and (3) the DSC curve of the crystal form B of succinate having an endothermic peak at 129.9±3° C.

According to an embodiment of the present disclosure, the crystal form B of succinate has one or two of the following characteristics:

(1) the crystal form B of succinate having a TGA curve substantially as shown in FIG. 30; and (2) the crystal form B of succinate having a DSC curve substantially as shown in FIG. 30.

According to an embodiment of the present disclosure, the crystal form B of adipate has characteristic peaks in an X-ray powder diffraction pattern using Cu-Kα radiation at the following 2θ angles: 4.98±0.20°, 10.69±0.20°, 13.88±0.20°, 21.41±0.20°, 24.97±0.20° and 26.15±0.20°.

According to an embodiment of the present disclosure, the crystal form B of adipate has characteristic peaks in an X-ray powder diffraction pattern at the following 2θ angles: 4.98±0.20°, 10.69±0.20°, 13.88±0.20°, 14.28±0.20°, 20.72±0.20°, 21.41±0.20°, 24.97±0.20° and 26.15±0.20°.

According to an embodiment of the present disclosure, the crystal form B of adipate has characteristic peaks in an X-ray powder diffraction pattern at the following 2θ angles: 4.98±0.20°, 9.23±0.20°, 10.69±0.20°, 13.88±0.20°, 14.28±0.20°, 19.35±0.20°, 20.72±0.20°, 21.41±0.20°, 24.97±0.20° and 26.15±0.20°.

According to an embodiment of the present disclosure, the 2θ diffraction angle, D-value and/or relative intensity of the X-ray powder diffraction pattern using Cu-Kα radiation by the crystal form B of adipate are shown in Table 13 below:

TABLE 13

XRPD diffraction peak data for the crystal form B of adipate

| No. | Position [°2θ] | D-spacing [A] | Relative intensity [%] |
|---|---|---|---|
| 1 | 4.98 | 17.76 | 100.00 |
| 2 | 9.23 | 9.58 | 10.76 |
| 3 | 10.69 | 8.28 | 66.57 |
| 4 | 13.88 | 6.38 | 29.18 |
| 5 | 14.28 | 6.20 | 15.70 |
| 6 | 15.90 | 5.58 | 6.08 |
| 7 | 17.97 | 4.94 | 7.25 |
| 8 | 19.35 | 4.59 | 11.12 |
| 9 | 20.72 | 4.29 | 13.47 |
| 10 | 21.41 | 4.15 | 24.88 |
| 11 | 24.97 | 3.57 | 30.67 |
| 12 | 26.15 | 3.41 | 55.99 |

According to an embodiment of the present disclosure, the crystal form B of adipate has an X-ray powder diffraction pattern substantially as shown in FIG. 13.

According to an embodiment of the present disclosure, the crystal form B of adipate has one, two or three of the following characteristics:

(1) the TGA curve of the crystal form B of adipate having a weight loss of about 1.23% at 150.0±3° C.;

(2) the DSC curve of the crystal form B of adipate having a starting point of an endothermic peak at 112.8±3° C.; and (3) the DSC curve of the crystal form B of adipate having an endothermic peak at 115.6±3° C.

According to an embodiment of the present disclosure, the crystal form B of adipate has one or two of the following characteristics:

(1) the crystal form B of adipate having a TGA curve substantially as shown in FIG. 31; and (2) the crystal form B of adipate having a DSC curve substantially as shown in FIG. 31.

According to an embodiment of the present disclosure, the crystal form A of sebacate has characteristic peaks in an X-ray powder diffraction pattern using Cu-Kα radiation at the following 2θ angles: 4.57±0.20°, 9.27±0.20°, 11.20±0.20°, 14.40±0.20°, 20.16±0.20°, 24.63±0.20° and 26.73±0.20°.

According to an embodiment of the present disclosure, the crystal form A of sebacate has characteristic peaks in an X-ray powder diffraction pattern at the following 2θ angles: 4.57±0.20°, 9.27±0.20°, 11.20±0.20°, 14.40±0.20°, 14.95±0.20°, 20.16±0.20°, 20.55±0.20°, 22.95±0.20°, 23.91±0.20°, 24.63±0.20° and 26.73±0.20°.

According to an embodiment of the present disclosure, the crystal form A of sebacate has characteristic peaks in an X-ray powder diffraction pattern at the following 2θ angles: 4.57±0.20°, 9.27±0.20°, 11.20±0.20°, 14.40±0.20°, 14.95±0.20°, 15.26±0.20°, 18.25±0.20°, 20.16±0.20°, 20.95±0.20°, 22.95±0.20°, 23.91±0.20°, 24.63±0.20° and 26.73±0.20°.

According to an embodiment of the present disclosure, the 2θ diffraction angle, D-value and/or relative intensity of the X-ray powder diffraction pattern using Cu-Kα radiation by the crystal form A of sebacate are shown in Table 14 below:

TABLE 14

XRPD diffraction peak data for the crystal form A of sebacate

| No. | Position [°2θ] | D-spacing [A] | Relative intensity [%] |
|---|---|---|---|
| 1 | 4.57 | 19.35 | 97.87 |
| 2 | 9.27 | 9.54 | 55.12 |
| 3 | 11.20 | 7.90 | 54.07 |
| 4 | 13.69 | 6.47 | 18.27 |
| 5 | 14.00 | 6.33 | 31.14 |
| 6 | 14.40 | 6.15 | 58.17 |
| 7 | 14.95 | 5.93 | 43.62 |
| 8 | 15.26 | 5.81 | 21.80 |
| 9 | 16.67 | 5.32 | 15.61 |
| 10 | 17.65 | 5.03 | 13.02 |
| 11 | 18.25 | 4.86 | 20.48 |
| 12 | 20.16 | 4.41 | 58.54 |
| 13 | 20.55 | 4.32 | 46.27 |
| 14 | 20.95 | 4.24 | 30.95 |
| 15 | 21.24 | 4.18 | 17.42 |
| 16 | 22.95 | 3.88 | 34.16 |
| 17 | 23.91 | 3.72 | 32.85 |
| 18 | 24.63 | 3.61 | 100.00 |
| 19 | 25.83 | 3.45 | 11.55 |
| 20 | 26.73 | 3.34 | 91.03 |
| 21 | 27.04 | 3.30 | 18.72 |
| 22 | 28.16 | 3.17 | 11.60 |
| 23 | 29.54 | 3.02 | 12.21 |

According to an embodiment of the present disclosure, the crystal form A of sebacate has an X-ray powder diffraction pattern substantially as shown in FIG. 14.

According to an embodiment of the present disclosure, the crystal form A of sebacate has one or two of the following characteristics:

(1) the TGA curve of the crystal form A of sebacate having a weight loss of about 0.45% at 150.0±3° C.; and (2) the DSC curve of the crystal form A of sebacate having two endothermic peaks at 80.9±10° C. and 142.1±10° C.

According to an embodiment of the present disclosure, the crystal form A of sebacate has one or two of the following characteristics:

(1) the crystal form A of sebacate having a TGA curve substantially as shown in FIG. 32; and (2) the crystal form A of sebacate having a DSC curve substantially as shown in FIG. 32.

According to an embodiment of the present disclosure, the crystal form A of p-toluenesulfonate has characteristic peaks in an X-ray powder diffraction pattern using Cu-Kα radiation at the following 2θ angles: 6.04±0.20°, 8.59±0.20°, 14.27±0.20°, 17.14±0.20° and 25.29±0.20°.

According to an embodiment of the present disclosure, the crystal form A of p-toluenesulfonate has characteristic peaks in an X-ray powder diffraction pattern at the following 2θ angles: 6.04±0.20°, 8.59±0.20°, 14.27±0.20°, 17.14±0.20°, 20.41±0.20°, 23.68±0.20°, 25.29±0.20° and 27.65±0.20°.

According to an embodiment of the present disclosure, the crystal form A of p-toluenesulfonate has characteristic peaks in an X-ray powder diffraction pattern at the following 2θ angles: 6.04±0.20°, 8.59±0.20°, 12.28±0.20°, 14.27±0.20°, 16.02±0.20°, 17.14±0.20°, 20.41±0.20°, 22.01±0.20°, 23.68±0.20°, 25.29±0.20° and 27.65±0.20°.

According to an embodiment of the present disclosure, the 2θ diffraction angle, D-value and/or relative intensity of the X-ray powder diffraction pattern using Cu-Kα radiation by the crystal form A of p-toluenesulfonate are shown in Table 15 below:

TABLE 15

XRPD diffraction peak data for the crystal form A of p-toluenesulfonate

| No. | Position [°2θ] | D-spacing [A] | Relative intensity [%] |
|---|---|---|---|
| 1 | 6.04 | 14.63 | 100.00 |
| 2 | 8.59 | 10.29 | 27.86 |
| 3 | 12.28 | 7.21 | 6.88 |
| 4 | 14.27 | 6.21 | 27.98 |
| 5 | 16.02 | 5.53 | 9.15 |
| 6 | 17.14 | 5.17 | 28.73 |
| 7 | 20.41 | 4.35 | 17.13 |
| 8 | 22.01 | 4.04 | 5.44 |
| 9 | 23.68 | 3.76 | 14.00 |
| 10 | 25.29 | 3.52 | 23.23 |
| 11 | 27.65 | 3.23 | 18.13 |

According to an embodiment of the present disclosure, the crystal form A of p-toluenesulfonate has an X-ray powder diffraction pattern substantially as shown in FIG. 15.

According to an embodiment of the present disclosure, the crystal form A of p-toluenesulfonate has one or two of the following characteristics:

(1) the TGA curve of the crystal form A of p-toluenesulfonate having a weight loss of about 3.29% at 150.0±3° C.; and (2) the DSC curve of the crystal form A of p-toluenesulfonate having an endothermic peak at 210.8±10° C.; particularly, the DSC curve of the crystal form A of p-toluenesulfonate having an endothermic peak at 210.8±5° C.

More specifically, the DSC curve of the crystal form A of p-toluenesulfonate having an endothermic peak at 72.7±10° C., particularly, 72.7±5° C.

According to an embodiment of the present disclosure, the crystal form A of p-toluenesulfonate has one or two of the following characteristics:

(1) the crystal form A of p-toluenesulfonate having a TGA curve substantially as shown in FIG. 33; and (2) the crystal form A of p-toluenesulfonate having a DSC curve substantially as shown in FIG. 33.

According to an embodiment of the present disclosure, the crystal form A of benzenesulfonate has characteristic peaks in an X-ray powder diffraction pattern using Cu-Kα radiation at the following 2θ angles: 6.16±0.20°, 8.98±0.20°, 14.22±0.20°, 16.90±0.20°, 18.31±0.20°, 20.92±0.20°, 25.11±0.20° and 26.29±0.20°.

According to an embodiment of the present disclosure, the crystal form A of benzenesulfonate has characteristic peaks in an X-ray powder diffraction pattern at the following 2θ angles: 6.16±0.20°, 8.98±0.20°, 14.22±0.20°, 15.67±0.20°, 16.90±0.20°, 17.55±0.20°, 18.31±0.20°, 20.34±0.20°, 20.92±0.20°, 25.11±0.20°, 26.29±0.20° and 29.24±0.20°.

According to an embodiment of the present disclosure, the crystal form A of benzenesulfonate has characteristic peaks in an X-ray powder diffraction pattern at the following 2θ angles: 6.16±0.20°, 8.98±0.20°, 14.22±0.20°, 15.67±0.20°, 16.90±0.20°, 17.55±0.20°, 18.31±0.20°, 20.34±0.20°, 20.92±0.20°, 23.54±0.20°, 24.65±0.20°, 25.11±0.20°, 26.29±0.20° and 29.24±0.20°.

According to an embodiment of the present disclosure, the 2θ diffraction angle, D-value and/or relative intensity of the X-ray powder diffraction pattern using Cu-Kα radiation by the crystal form A of benzenesulfonate are shown in Table 16 below:

TABLE 16

XRPD diffraction peak data for the crystal form A of benzenesulfonate

| No. | Position [°2θ] | D-spacing [A] | Relative intensity [%] |
|---|---|---|---|
| 1 | 6.16 | 14.35 | 100.00 |
| 2 | 8.98 | 9.85 | 32.00 |
| 3 | 11.80 | 7.50 | 16.88 |
| 4 | 12.15 | 7.29 | 13.55 |
| 5 | 12.88 | 6.87 | 8.42 |
| 6 | 14.22 | 6.23 | 45.29 |
| 7 | 15.67 | 5.65 | 16.14 |
| 8 | 16.39 | 5.41 | 8.19 |
| 9 | 16.90 | 5.25 | 44.60 |
| 10 | 17.55 | 5.05 | 21.13 |
| 11 | 18.31 | 4.85 | 38.43 |
| 12 | 18.68 | 4.75 | 10.16 |
| 13 | 19.17 | 4.63 | 14.56 |
| 14 | 19.85 | 4.47 | 9.63 |
| 15 | 20.34 | 4.37 | 19.10 |
| 16 | 20.92 | 4.25 | 24.15 |
| 17 | 21.74 | 4.09 | 10.69 |
| 18 | 23.54 | 3.78 | 16.52 |
| 19 | 24.65 | 3.61 | 16.14 |
| 20 | 25.11 | 3.55 | 32.44 |
| 21 | 26.29 | 3.39 | 48.85 |
| 22 | 27.32 | 3.27 | 7.75 |
| 23 | 28.69 | 3.11 | 6.56 |
| 24 | 29.24 | 3.05 | 21.51 |
| 25 | 31.08 | 2.88 | 3.70 |
| 26 | 32.29 | 2.77 | 2.52 |
| 27 | 33.22 | 2.70 | 3.04 |
| 28 | 34.37 | 2.61 | 3.17 |
| 29 | 35.61 | 2.52 | 2.40 |

According to an embodiment of the present disclosure, the crystal form A of benzenesulfonate has an X-ray powder diffraction pattern substantially as shown in FIG. 16.

According to an embodiment of the present disclosure, the crystal form A of benzenesulfonate has one, two, three or four of the following characteristics:

(1) the TGA curve of the crystal form A of benzenesulfonate having a weight loss of about 1.87% at 150.0±3° C.;

(2) the DSC curve of the crystal form A of benzenesulfonate having a starting point of an endothermic peak at 184.7±3° C.;

(3) the DSC curve of the crystal form A of benzenesulfonate having an endothermic peak at 187.0±3° C.; and (4) the DVS curve of the crystal form A of benzenesulfonate having a vapor sorption of less than about 2%, such as less than about 1.8%, particularly less than about 1.46% at 0% RH to 80% RH.

According to an embodiment of the present disclosure, the crystal form A of benzenesulfonate has one, two or three of the following characteristics:

(1) the crystal form A of benzenesulfonate having a TGA curve substantially as shown in FIG. 34;

(2) the crystal form A of benzenesulfonate having a DSC curve substantially as shown in FIG. 34; and (3) the crystal form A of benzenesulfonate having a DVS curve substantially as shown in FIG. 39.

According to an embodiment of the present disclosure, the crystal form A of hydrobromide has characteristic peaks in an X-ray powder diffraction pattern using Cu-Kα radiation at the following 2θ angles: 9.54±0.20° and 24.63±0.20°.

According to an embodiment of the present disclosure, the 2θ diffraction angle, D-value and/or relative intensity of the X-ray powder diffraction pattern using Cu-Kα radiation by the crystal form A of hydrobromide are shown in Table 17 below:

TABLE 17

XRPD diffraction peak data for the crystal form A of hydrobromide

| No. | Position [°2θ] | D-spacing [A] | Relative intensity [%] |
|---|---|---|---|
| 1 | 9.54 | 9.27 | 64.83 |
| 2 | 24.63 | 3.61 | 100.00 |

According to an embodiment of the present disclosure, the crystal form A of hydrobromide has an X-ray powder diffraction pattern substantially as shown in FIG. 17.

According to an embodiment of the present disclosure, the crystal form A of hydrobromide has one or two of the following characteristics:

(1) the TGA curve of the crystal form A of hydrobromide having a weight loss of about 7.86% at 150.0±3° C.; and (2) the DSC curve of the crystal form A of hydrobromide having three endothermic peaks at 96.5±5° C., 107.3±5° C. and 141.8±5° C.

According to an embodiment of the present disclosure, the crystal form A of hydrobromide has one or two of the following characteristics:

(1) the crystal form A of hydrobromide having a TGA curve substantially as shown in FIG. 35; and (2) the crystal form A of hydrobromide having a DSC curve substantially as shown in FIG. 35.

According to an embodiment of the present disclosure, the crystal form B of hydrobromide has characteristic peaks in an X-ray powder diffraction pattern using Cu-Kα radiation at the following 2θ angles: 9.48±0.20°, 15.89±0.20° and 23.98±0.20°.

According to an embodiment of the present disclosure, the crystal form B of hydrobromide has characteristic peaks in an X-ray powder diffraction pattern at the following 2θ angles: 9.48±0.20°, 15.89±0.20°, 19.40±0.20°, 23.98±0.20°, 26.55±0.20° and 28.02±0.20°.

According to an embodiment of the present disclosure, the 2θ diffraction angle, D-value and/or relative intensity of the X-ray powder diffraction pattern using Cu-Kα radiation by the crystal form B of hydrobromide are shown in Table 18 below:

TABLE 18

XRPD diffraction peak data for the crystal form B of hydrobromide

| No. | Position [°2θ] | D-spacing [A] | Relative intensity [%] |
|---|---|---|---|
| 1 | 9.48 | 9.33 | 71.80 |
| 2 | 15.89 | 5.58 | 38.95 |
| 3 | 19.40 | 4.58 | 22.35 |
| 4 | 23.98 | 3.71 | 100.00 |
| 5 | 26.55 | 3.36 | 22.87 |
| 6 | 28.02 | 3.18 | 21.56 |

According to an embodiment of the present disclosure, the crystal form B of hydrobromide has an X-ray powder diffraction pattern substantially as shown in FIG. 18.

According to an embodiment of the present disclosure, the crystal form B of hydrobromide has one or two of the following characteristics:

(1) the TGA curve of the crystal form B of hydrobromide having a weight loss of about 4.95% at 150.0±3° C.; and (2) the DSC curve of the crystal form B of hydrobromide having three endothermic peaks at 81.6±10° C., 128.9±10° C. and 163.6±10° C.; particularly, the DSC curve of the crystal form B of hydrobromide having three endothermic peaks at 81.6±5° C., 128.9±5° C. and 163.6±5° C.

According to an embodiment of the present disclosure, the crystal form B of hydrobromide has one or two of the following characteristics:

(1) the crystal form B of hydrobromide having a TGA curve substantially as shown in FIG. 36; and (2) the crystal form B of hydrobromide having a DSC curve substantially as shown in FIG. 36.

The present disclosure further provides a preparation method for the salt of the compound of formula (I), which comprises the step of contacting the compound of formula (I) with an inorganic acid or an organic acid:

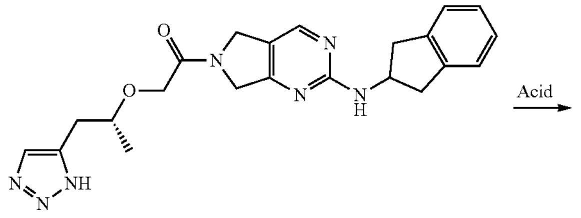

(I)

-continued

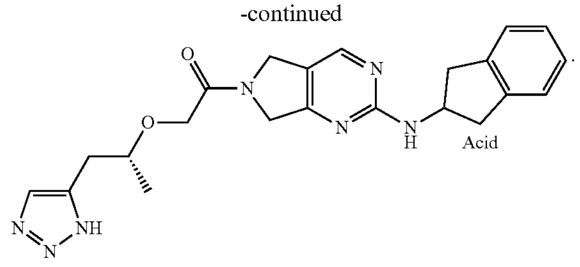

Salt of compound I

According to an embodiment of the present disclosure, the inorganic acid or the organic acid is independently selected from the definitions described above.

According to an embodiment of the present disclosure, the compound of formula (I) and the inorganic acid or the organic acid may be in a molar ratio of 1:(0.5-5), for example, 1:(0.5-2), and illustratively 1:0.5 or 1:1.

The present disclosure further provides a preparation method for the crystal form of the salt of the compound of formula (I), which comprises the following steps of: stirring the compound of formula (I) with the corresponding inorganic acid or organic acid in a solvent at room temperature, transferring the resulting clear sample to a condition with a temperature of 5° C. to −20° C. for further stirring, and transferring the clear sample to a condition with room temperature to evaporate the solvent.

According to an embodiment of the present disclosure, the inorganic acid or the organic acid is independently selected from the definitions described above.

According to an embodiment of the present disclosure, the compound of formula (I) and the inorganic acid or the organic acid may be in a molar ratio of 1:(0.5-5), for example, 1:(0.5-2), and illustratively 1:0.5 or 1:1.

The present disclosure further provides a pharmaceutical composition comprising the salt of the compound of formula (I), for example, a solid form thereof, such as a crystal form or amorphous form thereof.

According to an embodiment of the present disclosure, the pharmaceutical composition may further comprise a pharmaceutically acceptable auxiliary material, for example, a carrier or an excipient.

According to an embodiment of the present disclosure, in the pharmaceutical composition, the salt of the compound of formula (I) is present in a therapeutically effective amount.

The present disclosure further provides an use of the salt of the compound of formula (I), for example, a solid form thereof, such as a crystal form or amorphous form thereof, in the manufacture of a medicament. Preferably, the medicament is used for treating and/or preventing a ATX-related disease.

The present disclosure further provides a method of prevention and/or treatment of an Autotaxin (ATX)-related disease, which comprises administering to a patient in need thereof a therapeutically effective amount of the salt of the compound of formula (I) described above, for example, a solid form thereof, such as a crystal form or amorphous form thereof, or the pharmaceutical composition.

The present disclosure further provides a salt of a compound of formula (I), for example, a solid form thereof, such as a crystal form or amorphous form thereof, or the pharmaceutical composition, for use in the treatment and/or prevention of an Autotaxin (ATX)-related disease.

According to an embodiment of the present disclosure, the ATX-related disease comprises at least one selected from the following: cancer, metabolic diseases, renal diseases, hepatic diseases, fibrotic diseases, interstitial lung diseases, proliferative diseases, inflammatory diseases, pain, autoimmune diseases, respiratory diseases, cardiovascular diseases, neurodegenerative diseases, dermatological disorders and/or abnormal angiogenesis-related diseases.

According to an embodiment of the present disclosure, the ATX-related disease comprises at least one selected from the following: interstitial lung diseases, pulmonary fibrosis, hepatic fibrosis and renal fibrosis.

According to an embodiment of the present disclosure, the ATX-related disease comprises idiopathic pulmonary fibrosis.

According to an embodiment of the present disclosure, the ATX-related disease comprises type II diabetes and non-alcoholic steatohepatitis.

According to an embodiment of the present disclosure, the ATX-related disease comprises neuropathic pain and inflammatory pain.

According to an embodiment of the present disclosure, the ATX-related disease comprises osteoarthritis-related pain.

Where used as a medicament, the salt or the solid form thereof of the present disclosure may be administered in the form of a pharmaceutical composition. Those compositions may be prepared in a manner well known in the pharmaceutical arts and may be administered by a variety of routes depending on whether local or systemic treatment is desired and the area to be treated. The pharmaceutical composition can be administered topically (e.g., by transdermal, dermal, ocular and mucosal routes, including intranasal, vaginal and rectal delivery routes), pulmonarily (e.g., by inhalation or insufflation of powders or aerosols, including by nebulizer; by intratracheal and intranasal routes), orally or parenterally. The parenteral administration includes intravenous, intra-arterial, subcutaneous, intraperitoneal or intramuscular injection or infusion; or intracranial (e.g., intrathecal or intracerebroventricular) administration. The pharmaceutical composition may be administered parenterally in a single bolus form, or may be administered by, for example, continuous infusion pump. The pharmaceutical composition and formulation administered topically may include a transdermal patch, an ointment, a lotion, a cream, a gel, a drop, a suppository, a spray, a liquid and a powder. Conventional pharmaceutical carriers, water, powders or oily bases, thickeners and the like may be necessary or desirable.

In preparing the composition of the present disclosure, the active ingredient (the salt or the solid form thereof of the present disclosure) is typically mixed with an excipient, diluted by the excipient or contained in such a carrier, for example, in the form of a capsule, a sachet, paper or other containers.

When used as a diluent, the excipient may be a solid, semi-solid or liquid substance that serves as a vehicle, a carrier or a medium for the active ingredient. Thus, the composition may be in the form of a tablet, a pill, a powder, a lozenge, a sachet, a cachet, an elixir, a suspension, an emulsion, a solution, a syrup, an aerosol (solid or dissolved in a liquid vehicle); an ointment, soft and hard gelatin capsules, a suppository, a sterile injectable solution and a sterile packaged powder containing, for example, up to 10% by weight of the active ingredient.

Certain examples of suitable excipients include lactose, glucose, sucrose, sorbitol, mannitol, starch, acacia, calcium phosphate, alginate, tragacanth, gelatin, calcium silicate, microcrystalline cellulose, polyvinylpyrrolidone, cellulose, water, syrup and methylcellulose. The formulation may further contain a lubricant such as talc, magnesium stearate and mineral oil; a wetting agent; an emulsifier and a suspending agent; a preservative such as methyl benzoate and hydroxypropyl benzoate; a sweetening agent and a flavoring agent. The composition of the present disclosure may be formulated by the methods known in the art so as to provide immediate, sustained or delayed release of the active ingredient after administration to the patient.

The composition may be formulated in unit dosage forms containing about 5 mg to 1200 mg, typically about 50 mg to 800 mg, of the active ingredient per dose. The term "unit dosage form" refers to physically discrete single dosage units suitable for use in human patients and other mammals, each unit containing a predetermined amount of active substance mixed with a suitable pharmaceutical excipient that can produce the desired therapeutic effect by calculation.

The active compound may be effective in a wide range of doses and is generally administered in a pharmaceutically effective amount. However, it will be understood that the amount of the compound actually administered is usually determined by a physician, in the light of the relevant circumstances, including the disorder to be treated, the selected route of administration, the compound actually administered; the age, weight and response of an individual patient; the severity of patient's symptoms and the like.

For the preparation of solid compositions such as tablets, the main active ingredient is mixed with pharmaceutical excipients to form solid preformulation compositions containing a homogeneous mixture of the salt or the solid form thereof of the present disclosure. When those preformulation compositions are referred to be homogeneous, it is meant that the active ingredient is generally distributed evenly throughout the composition so that the composition may be readily divided into equally effective unit dosage forms such as tablets, pills and capsules. The solid preformulation is then divided into unit dosage forms of the above type containing, for example, about 0.1 mg to 1000 mg of the active ingredient of the present disclosure.

The tablets or pills of the present disclosure may be coated or compounded to obtain a dosage form affording the advantage of long-acting effect. For example, the tablets or pills contain an inner dosage component and an outer dosage component, the latter being in the form of an envelope of the former.

The two components may be separated by an enteric coating layer which serves to prevent the disintegration in the stomach to allow the inner component to pass through the duodenum entirely or to be delayed in release. A variety of substances may be used for such enteric coating layers or coatings, including various polymeric acids and mixtures of polymeric acids and such substances as shellac, cetyl alcohol and cellulose acetate.

Liquid forms in which the salt or the solid form thereof and the composition of the present disclosure may be incorporated for oral or injection administration include aqueous solutions, suitably flavored syrups, aqueous or oil suspensions; emulsions flavored with edible oils such as cottonseed oil, sesame oil, coconut oil or peanut oil; and elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described above. In certain embodiments, the composition is administered by the oral or intranasal or respiratory route for local or systemic effect. The composition may be nebulized by using inert gases. The nebulized solution may be inhaled directly from the nebulizing device or the nebulizing device may be attached to a face mask, tent or an intermittent positive pressure ventilator. The solution, suspension or powder compositions may be administered orally, or nasally by means of a device which delivers the formulation in a suitable manner.

The amount of the salt or the solid form thereof and the composition administered to a patient varies depending on the drug administered, the purpose of the administration such as for prophylaxis or therapy; the condition of the patient, the mode of administration and the like. In therapeutic applications, the composition may be administered to a patient suffering from a disease in an amount sufficient to cure or at least partially arrest the symptoms of the disease and its complications. The effective dosage should be determined based on the state of the disease being treated and the judgment of the attending clinician, which depends on factors such as the severity of the disease, and the age, weight and general condition of the patient and the like.

The composition administered to the patient may be in the form of the pharmaceutical composition as described above. These compositions may be sterilized by conventional sterilization techniques or by filter sterilization. The aqueous solutions may be packaged for use as is, or lyophilized, and the lyophilized formulation is mixed with a sterile aqueous carrier prior to administration. The compound formulation usually has a pH of 3-11, more preferably 5-9, and most preferably 7-8. It will be understood that the use of certain excipients, carriers or stabilizers as described above may result in the formation of a pharmaceutical salt.

The therapeutic dosage of the salt or the solid form thereof of the present disclosure may depends, for example, on the particular use of the treatment, the manner in which the compound is administered, the health and condition of the patient, and the judgment of the prescribing physician.

The proportion or concentration of the compound of the present disclosure in the pharmaceutical composition may vary depending on a variety of factors including the dosage, chemical properties (e.g., hydrophobicity), and the route of administration. For example, the compound of the present disclosure may be provided for parenteral administration by a physiological buffered aqueous solution containing about 0.1-10% w/v of the compound. Certain typical dosage ranges from about 1 g/kg body weight/day to about 1 g/kg body weight/day. In certain embodiments, the dosage ranges from about 0.01 mg/kg body weight/day to about 100 mg/kg body weight/day. The dosage is likely to depend on such variables as the type and degree of progression of the disease or disorder, the general health condition of the particular patient, the relative biological potency of the compound selected, the excipient formulation and its route of administration. Effective dosage can be extrapolated from dose-response curves derived from in vitro or animal model test systems.

Definitions and Explanations of Terms

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions and the compound structures in such combinations and incorporations should fall within the scope of the present specification.

Unless otherwise stated, a numerical range set forth in the description and claims shall be construed as at least including each specific integer within the range. For example, two or more represent 2, 3, 4, 5, 6, 7, 8, 9, 10 or more. when certain numerical ranges are defined or understood as "numbers", it shall be construed as including both endpoints of the range, each integer within the range, and each decimal within the range. For example, "numbers of 0-10" shall be construed as including not only each of integers 0, 1, 2, 3, 4, 5, 6, 7, 8, 9 and 10, but also at least the sums of each integer and 0.1, 0.2, 0.3, 0.4, 0.5, 0.6, 0.7, 0.8 or 0.9.

When "about" numerical value is recited in the specification and claims, it shall be construed as including the numerical value itself, as well as numerical values within a range around the numerical value that is acceptable in the art, for example, numerical values within the range of ±15% of the numerical value, numerical values within the range of 10% of the numerical value and numerical values within the range of ±5% of the numerical value. For example, about 10 represents that it includes a value within the range of 10±1.5, i.e., within the range of 8.5 to 11.5; a value within the range of 10±1.0, i.e., within the range of 9.0 to 11.0; and a value within the range of 10±0.5, i.e., within the range of 9.5 to 10.5.

The term "patient" refers to any animal including mammals, preferably mice, rats, other rodents, rabbits, dogs, cats, pigs, cattle, sheep, horses or primates, and most preferably humans.

The term "therapeutically effective amount" refers to the amount of the active compound or drug that causes a biological or medical response that researchers, veterinarians, physicians or other clinicians are looking for in tissues, systems, animals, individuals or humans, including one or more of the following effects: (1) disease prevention: for example, the prevention of a disease, disorder or condition in an individual who is susceptible to the disease, disorder or condition but has not yet experienced or exhibited the pathology or symptoms of the disease; (2) disease inhibition: for example, the inhibition of a disease, disorder or condition in an individual who is experiencing or exhibiting the pathology or symptoms of the disease, disorder or condition. (i.e., the prevention of the further development of the pathology and/or symptoms); and (3) disease alleviation: for example, the alleviation of a disease, disorder or condition in an individual who is experiencing or exhibiting the pathology or symptoms of the disease, disorder or condition (i.e., the reverse of the pathology and/or symptoms).

The term "pharmaceutically acceptable" means that a formula component or an active ingredient does not unduly adversely affect a general therapeutic target's health.

The term "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present disclosure and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose, cellulose acetate and the like), gelatin, talc, solid lubricants (e.g., stearic acid and magnesium stearate), calcium sulfate, vegetable oil (e.g., soybean oil, sesame oil, peanut oil, olive oil and the like), polyols (e.g., propylene glycol, glycerol, mannitol, sorbitol and the like), emulsifiers, wetting agents (e.g., sodium lauryl sulfate), colorants, flavoring agents, stabilizers, antioxidants, preservatives, pyrogen-free water, etc.

Advantageous Effects

The salts of the compound of formula (I) and the crystal forms thereof of the present disclosure have a good solubility, stability and hygroscopicity. For example, the crystal form A of benzenesulfonate of the compound of formula (I) has the following advantages that: (1) it has weak hygroscopicity and no polymorphic transition occurred after DVS test, which is convenient for druggable CMC control, thus providing a material basis for preparation research and development; (2) it has uniform granularity of less than 50 m under PLM, which ensures that impurities in the reaction process can be effectively removed in the crystallization process, thus improving production efficiency and reducing production cost; (3) it has significantly improved solubility and is suitable for drug development and exerting clinical advantages; and (4) it has better solid-state stability.

Therefore, the salts and the crystal forms thereof provided by the present disclosure are more suitable for pharmaceutical use. Moreover, the their preparation methods are simple and convenient, and are suitable for large-scale production.

DETAILED DESCRIPTION

Figure 1:
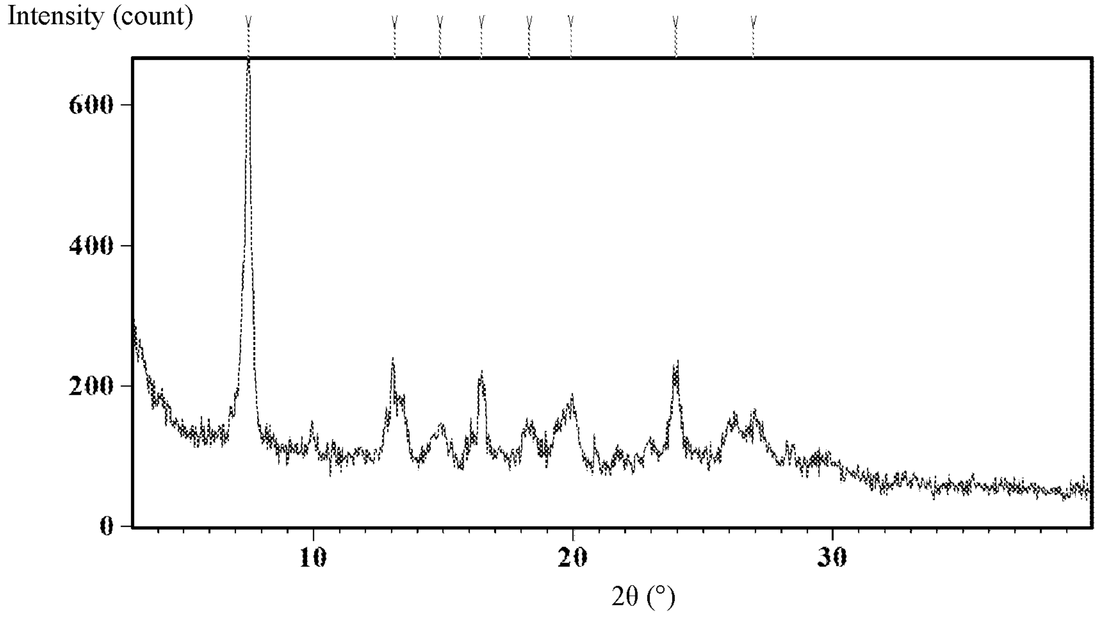
FIG. 1 is an XRPD pattern (instrument 2) of the crystal form A of hydrochloride of the compound of formula (I)
Figure 2:
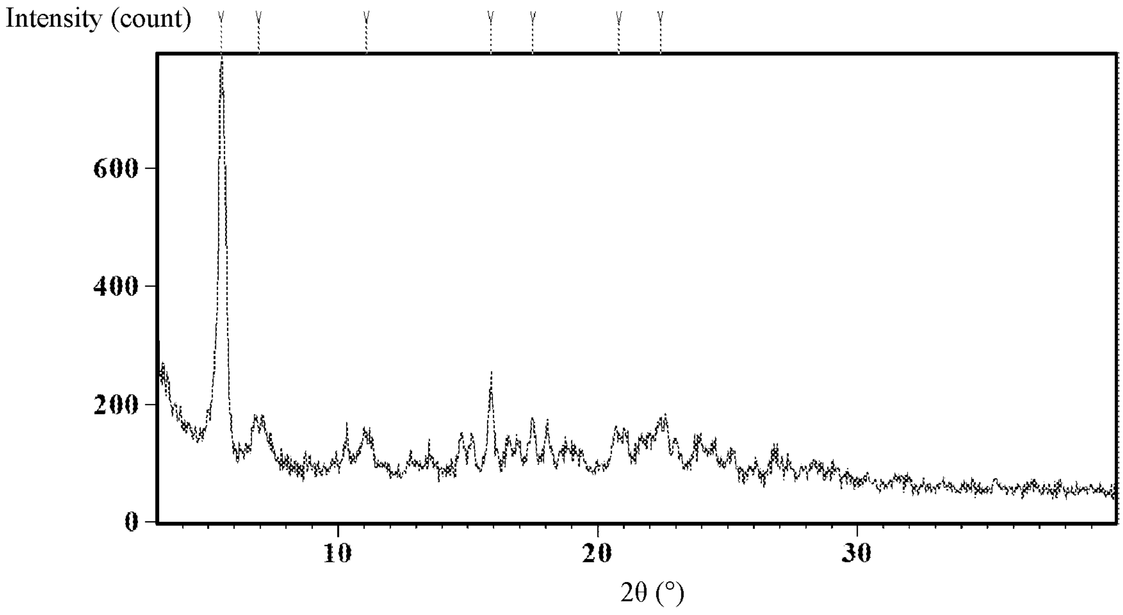
FIG. 2 is an XRPD pattern (instrument 2) of the crystal form A of sulfate of the compound of formula (I)
Figure 3:
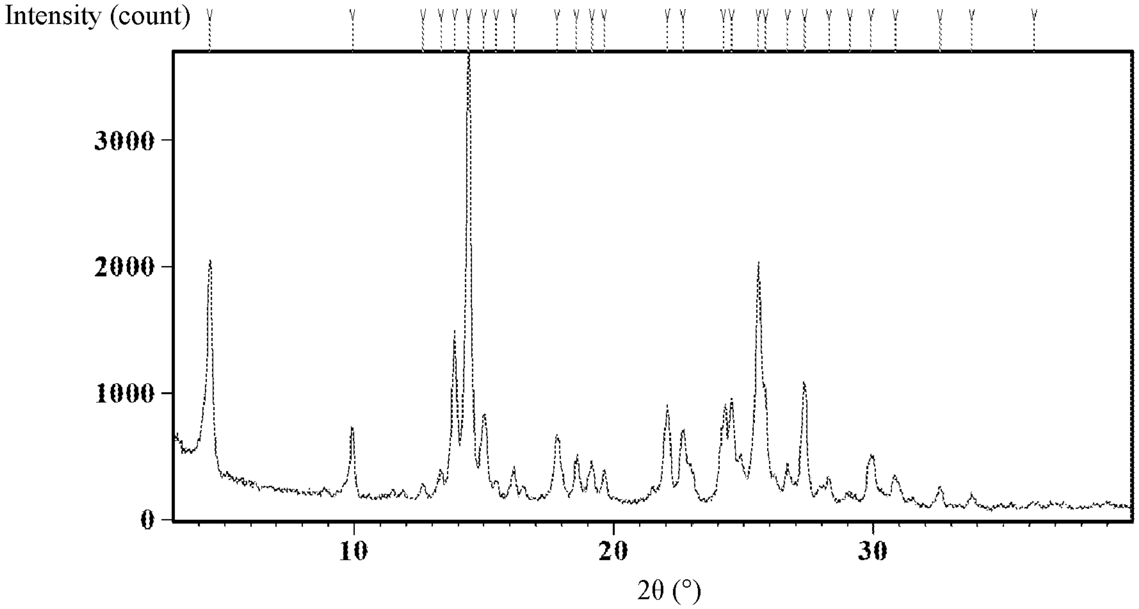
FIG. 3 is an XRPD pattern (instrument 3) of the crystal form A of maleate of the compound of formula (I)
Figure 4:
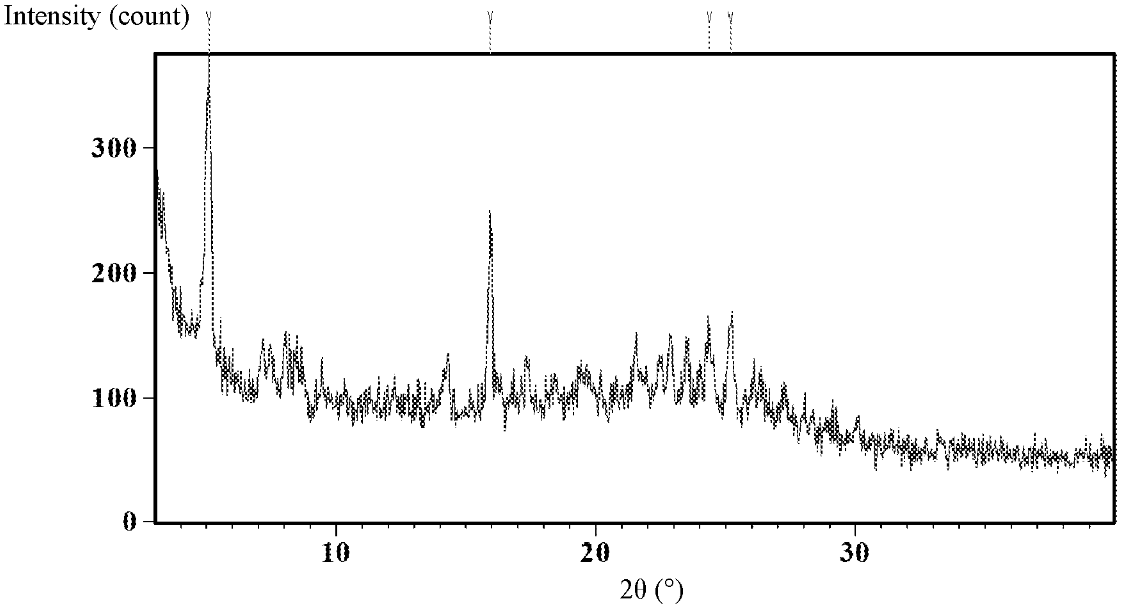
FIG. 4 is an XRPD pattern (instrument 2) of the crystal form A of phosphate of the compound of formula (I)
Figure 5:
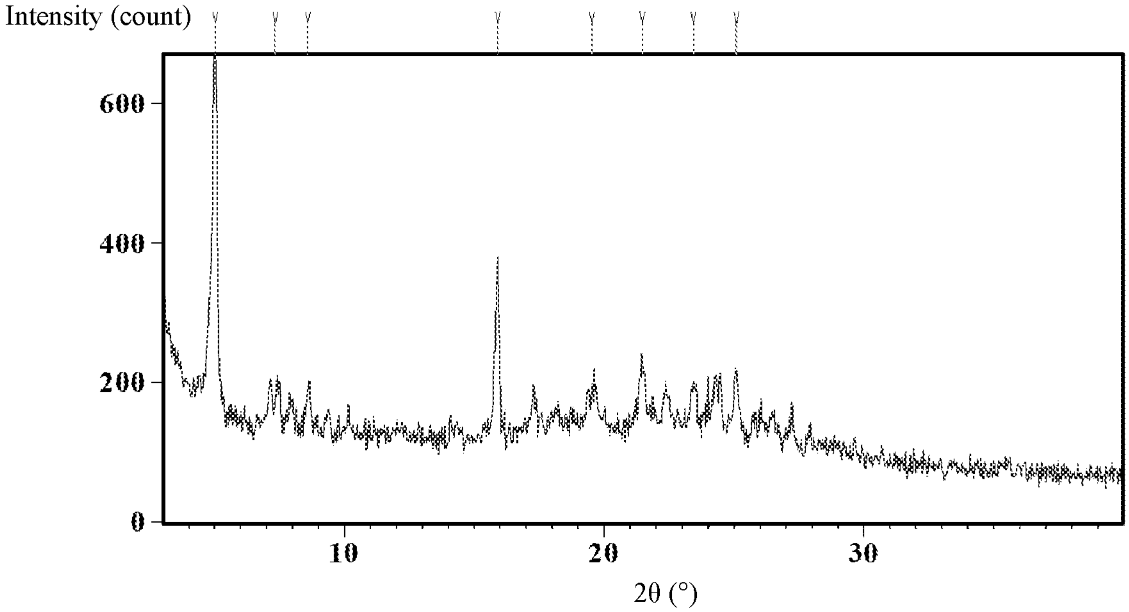
FIG. 5 is an XRPD pattern (instrument 2) of the crystal form A of tartrate of the compound of formula (I)
Figure 6:
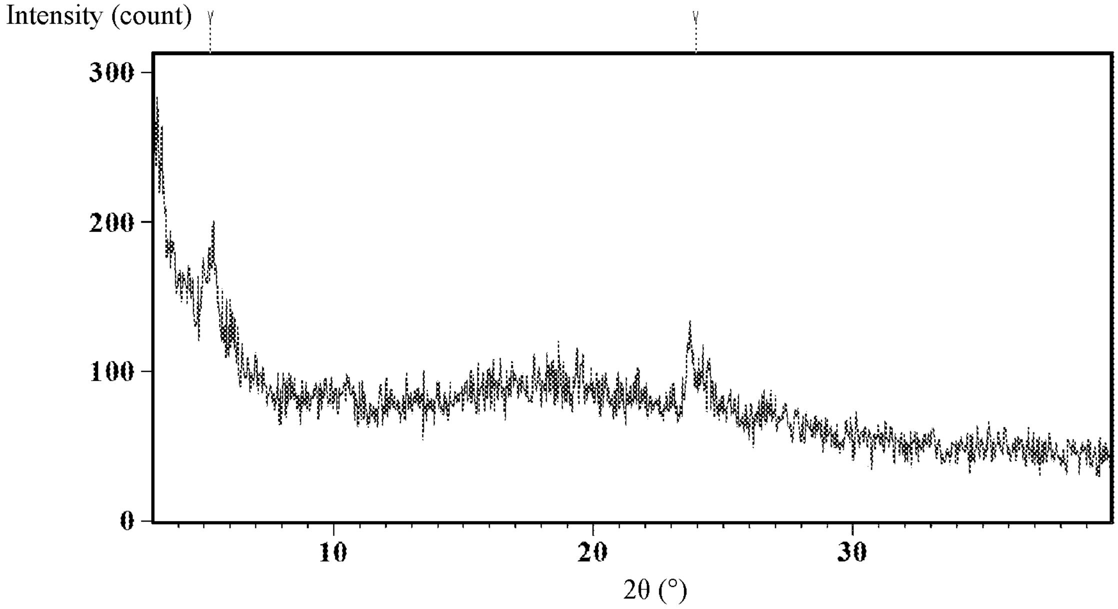
FIG. 6 is an XRPD pattern (instrument 2) of the crystal form B of tartrate of the compound of formula (I)
Figure 7:
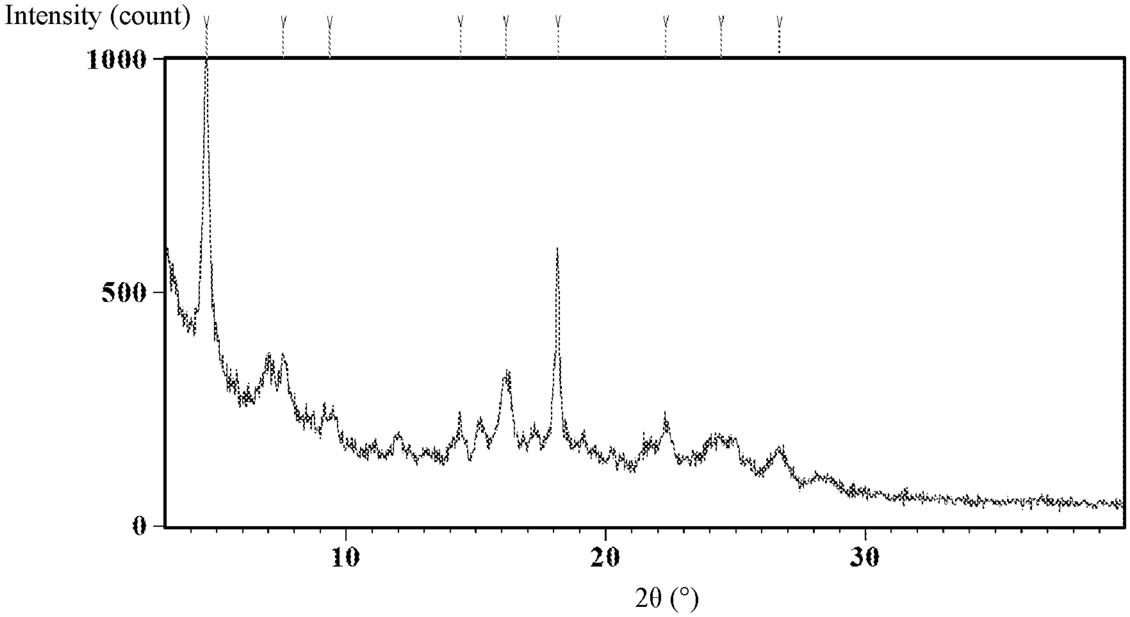
FIG. 7 is an XRPD pattern (instrument 3) of the crystal form C of tartrate of the compound of formula (I)
Figure 8:
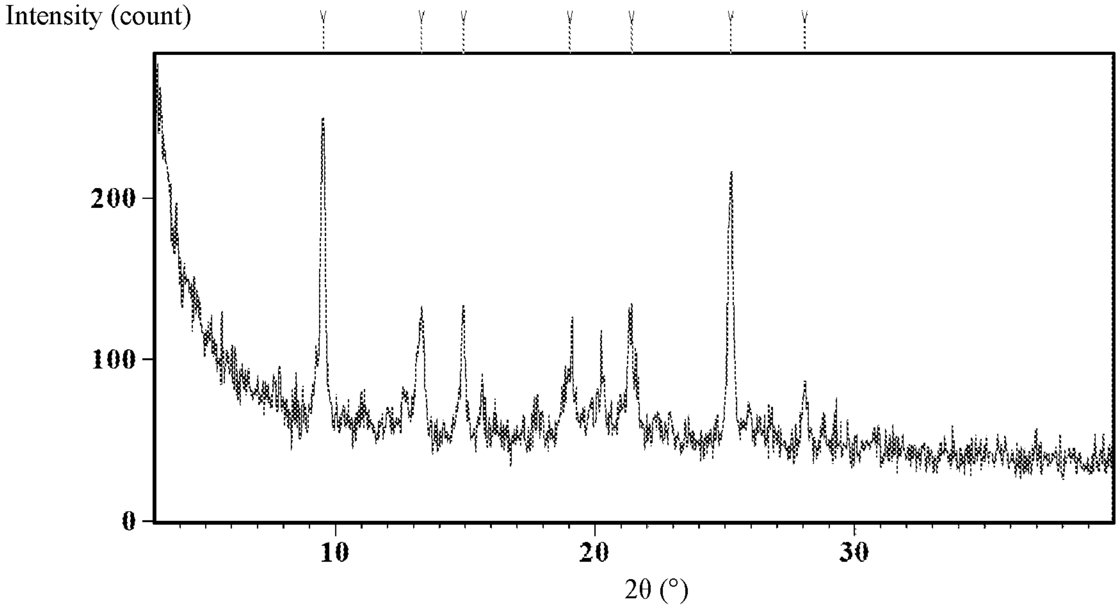
FIG. 8 is an XRPD pattern (instrument 2) of the crystal form A of fumarate of the compound of formula (I)
Figure 9:
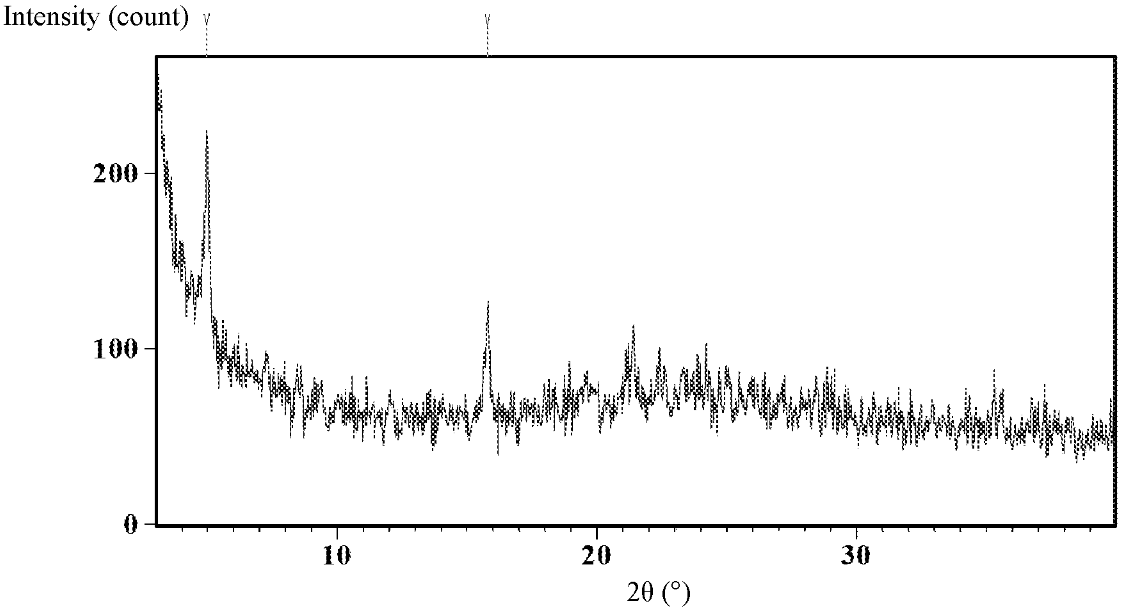
FIG. 9 is an XRPD pattern (instrument 2) of the crystal form A of citrate of the compound of formula (I)
Figure 10:
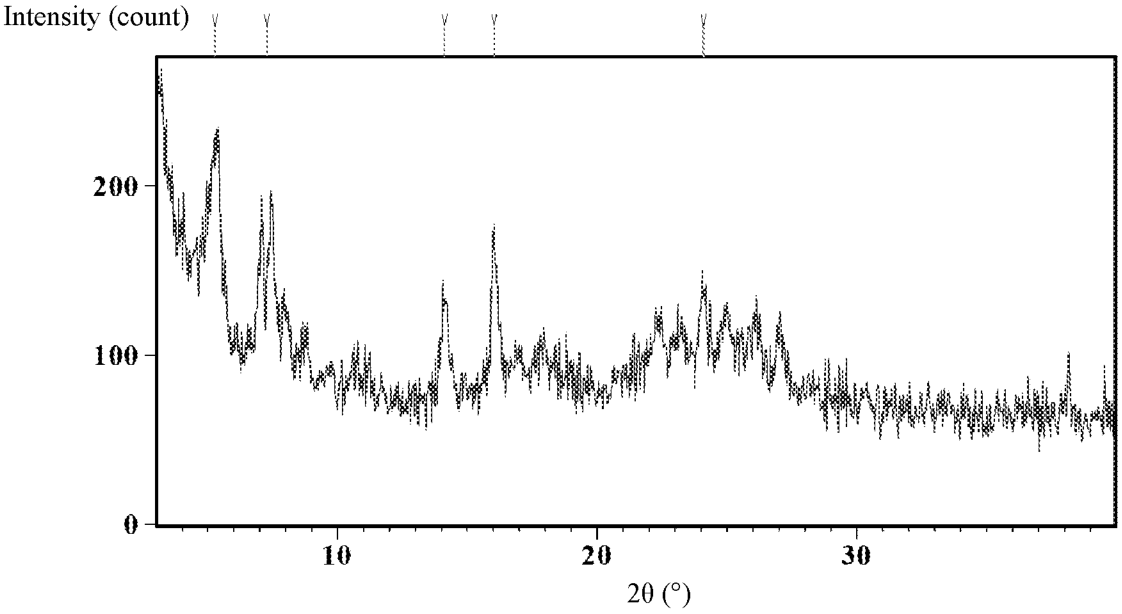
FIG. 10 is an XRPD pattern (instrument 2) of the crystal form A of glycolate of the compound of formula (I)
Figure 11:
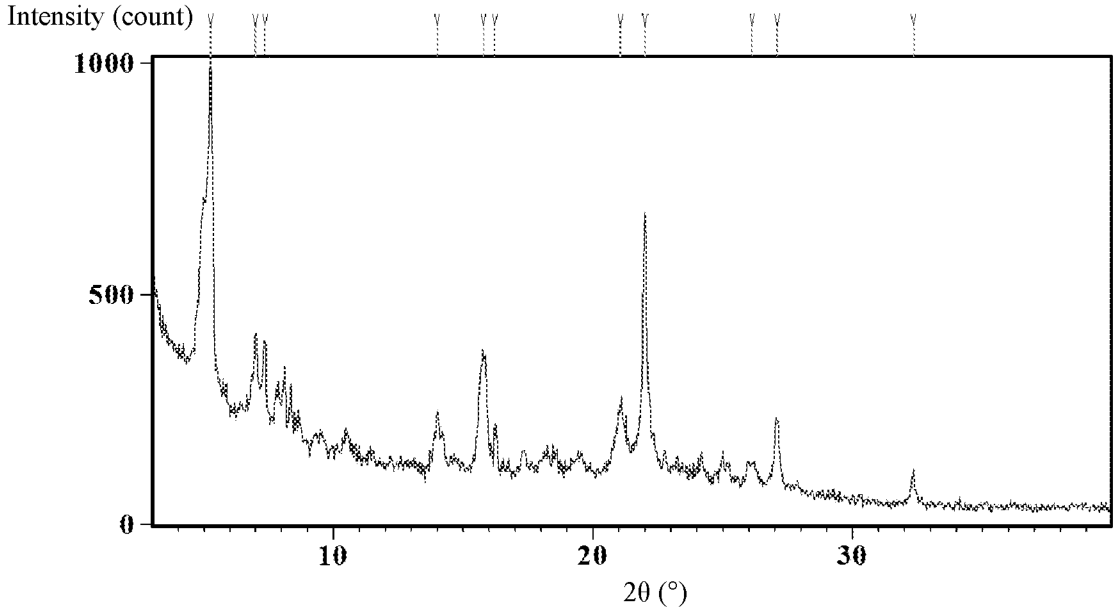
FIG. 11 is an XRPD pattern (instrument 3) of the crystal form A of succinate of the compound of formula (I)
Figure 12:
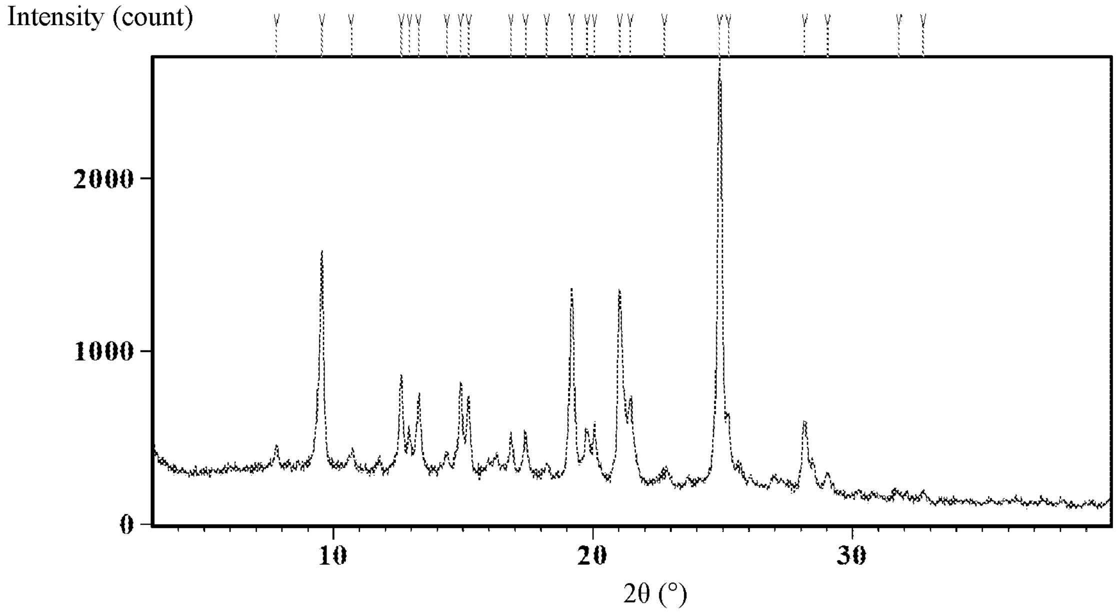
FIG. 12 is an XRPD pattern (instrument 1) of the crystal form B of succinate of the compound of formula (I)
Figure 13:
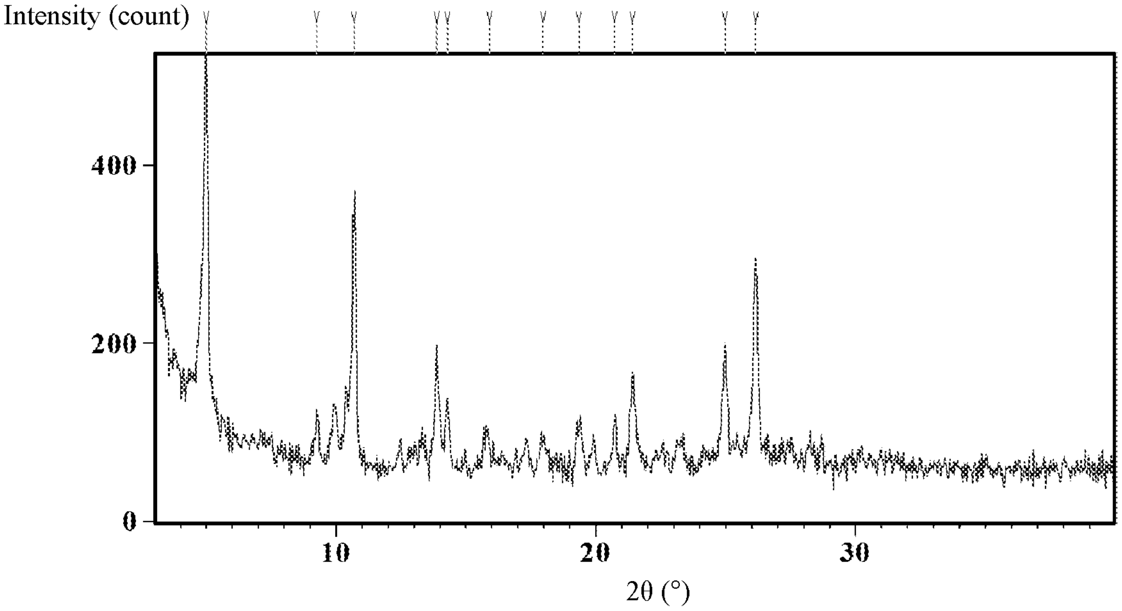
FIG. 13 is an XRPD pattern (instrument 2) of the crystal form B of adipate of the compound of formula (I)
Figure 14:
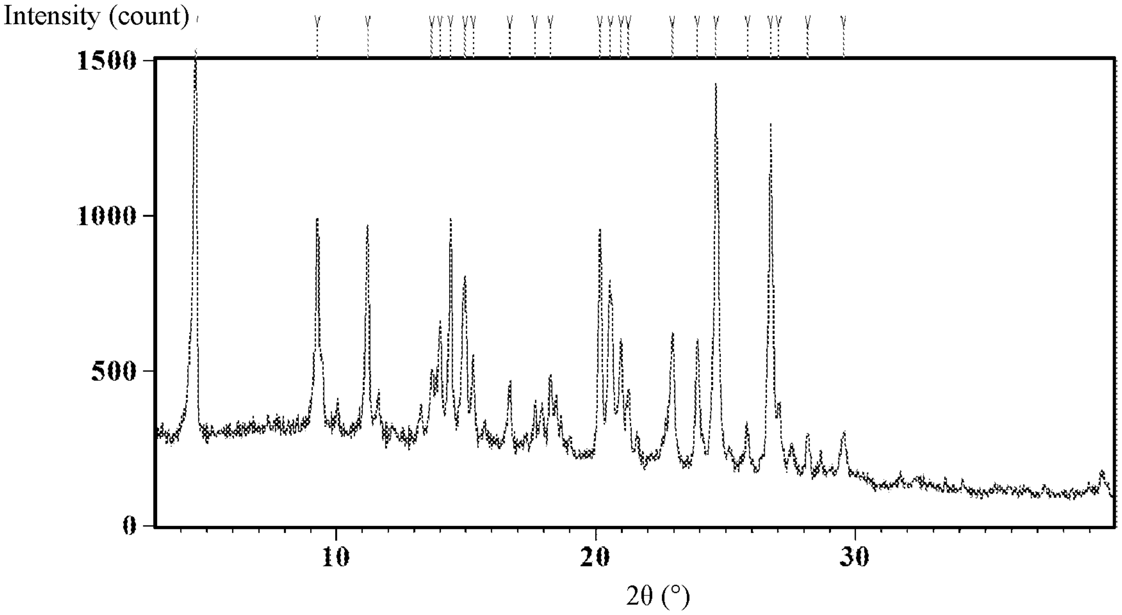
FIG. 14 is an XRPD pattern (instrument 1) of the crystal form A of sebacate of the compound of formula (I)
Figure 15:
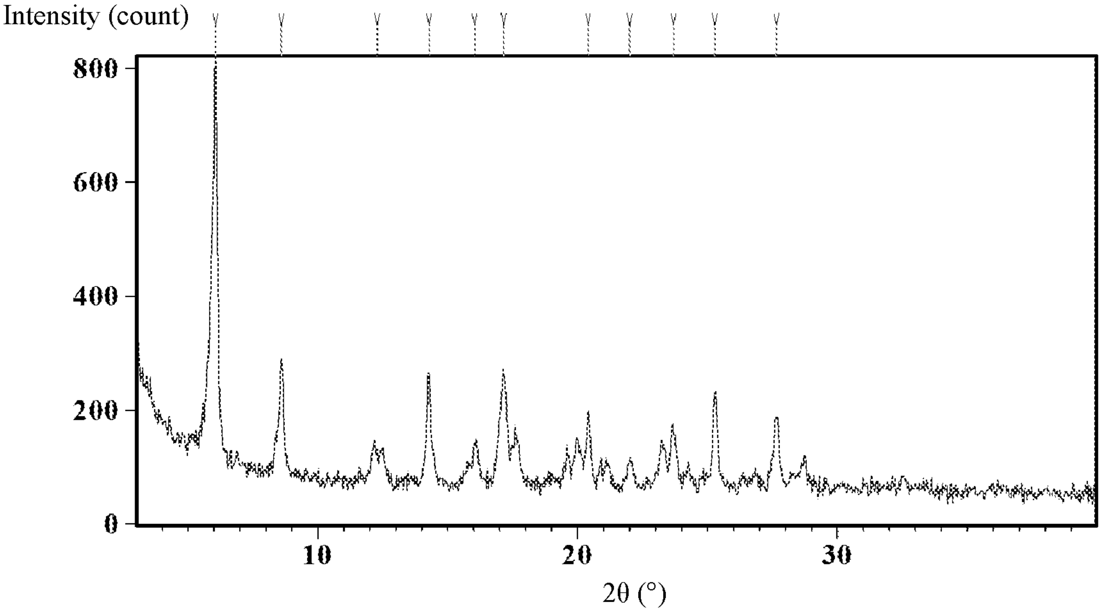
FIG. 15 is an XRPD pattern (instrument 2) of the crystal form A of p-toluenesulfonate of the compound of formula (I)
Figure 16:
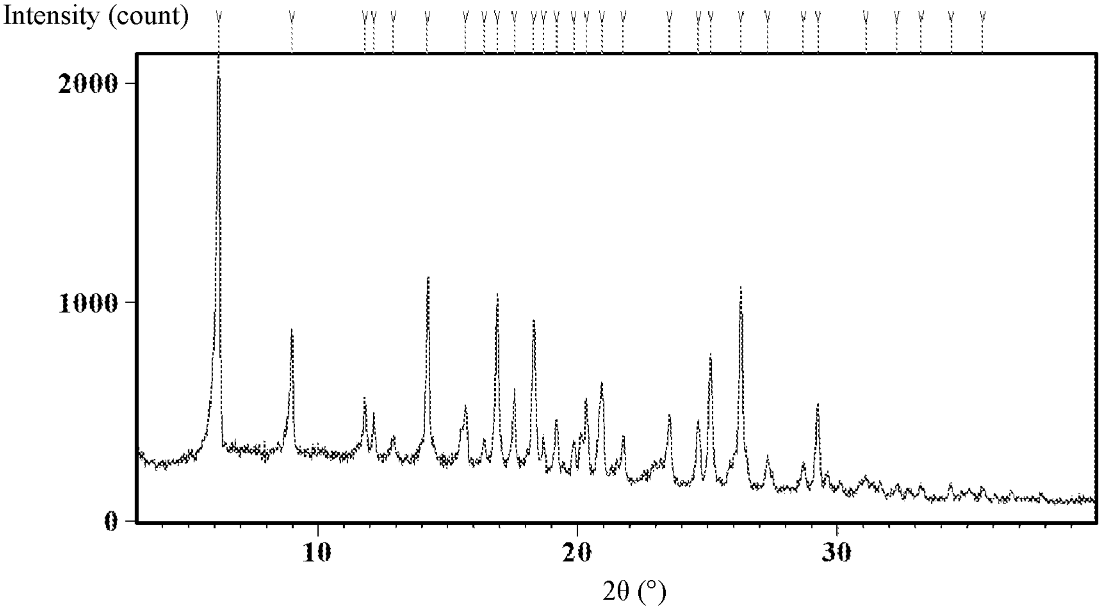
FIG. 16 is an XRPD pattern (instrument 1) of the crystal form A of benzenesulfonate of the compound of formula (I)
Figure 17:
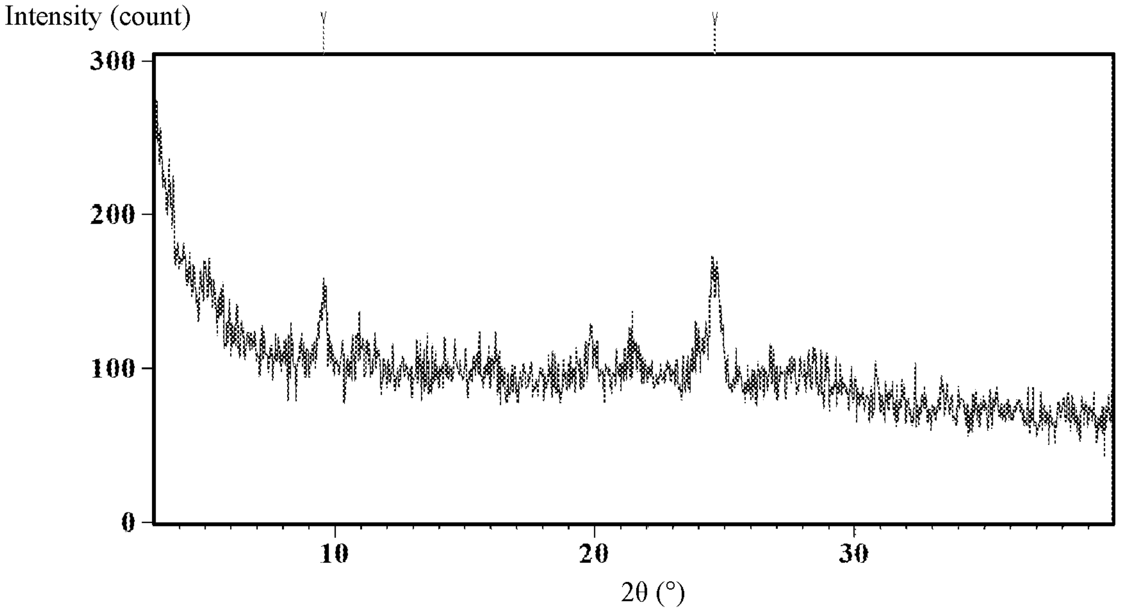
FIG. 17 is an XRPD pattern (instrument 2) of the crystal form A of hydrobromide of the compound of formula (I)
Figure 18:
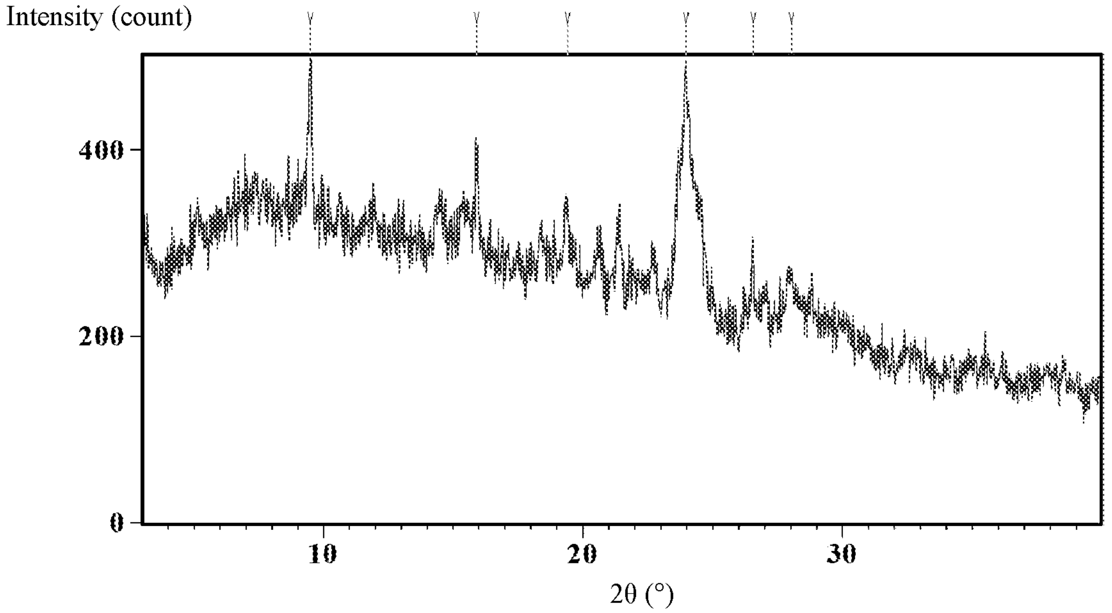
FIG. 18 is an XRPD pattern (instrument 1) of the crystal form B of hydrobromide of the compound of formula (I)

The salt form of the compound of formula (I) and the crystal form thereof as well as the preparation method and use therefor disclosed herein will be described in detail with reference to the following examples. The following examples are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared using known methods.

Detection Instrument and Method for Crystal Form

1. X-Ray Powder Diffraction (XRPD)

The XRPD patterns are acquired on an X-ray powder diffraction analyzer manufactured by PANalytacal, and the scanning parameters are shown in the Table 19-1 below:

TABLE 19-1

| Parameter | Instrument 1 | Instrument 2 | Instrument 3 |
|---|---|---|---|
| Model | Empyrean | X' Pert3 | X' Pert3 |
| X-ray | Cu, Kα, Kα1 (Å): 1.540598, Kα2 (Å): 1.544426 Kα2/Kα1 intensity ratio: 0.50 | Cu, Kα, Kα1 (Å): 1.540598, Kα2 (Å): 1.544426 Kα2/Kα1 intensity ratio: 0.50 | Cu, Kα. Kα1 (Å): 1.540598, Kα2 (Å): 1.544426 Kα2/Kα1 intensity ratio: 0.50 |
| X-ray light tube settings | 45 kV, 40 mA | 45 kV, 40 mA | 45 kV, 40 mA |
| Divergence slit | Automatic | 1/8° | 1/8° |
| Scanning mode | Continuous | Continuous | Continuous |
| Scanning range (°2Theta) | 3-40 | 3-40 | 3-40 |
| Scanning time of each step (s) | 17.8 | 46.7 | 46.7 |
| Scanning step length (°2Theta) | 0.0167 | 0.0263 | 0.0263 |
| Test time | ~5 min 30 s | ~5 min | ~5 min |

2. Thermogravimetric Analysis (TGA) and Differential Scanning Calorimetry (DSC)

TGA patterns and DSC patterns are acquired on a TA Q5000/5500 thermogravimetric analyzer and a TA 2500 differential scanning calorimeter, respectively, and the test parameters are listed in Table 19-2 below.

TABLE 19-2

| Parameter | TGA | DSC |
|---|---|---|
| Method | Linear heating | Linear heating |
| Sample pan | Aluminum pan, open | Aluminum pan, gland/ non-gland |
| Temperature range | Room temperature-setting endpoint temperature | 25° C.-setting endpoint temperature |
| Scanning rate (° C./min) | 10 | 10 |
| Protective gas | Nitrogen | Nitrogen |

3. Liquid-State Nuclear Magnetic Resonance (Solution NMR):

The liquid-state nuclear magnetic resonance patterns are acquired on a Bruker 400M nuclear magnetic resonance spectrometer with DMSO-d6 as solvent.

4. High Performance Liquid Chromatograph (HPLC):

In the tests, the purity, solubility and stability are tested by an Agilent 1260 high-performance liquid chromatograph, and the analysis conditions are shown in Table 19-3 below:

TABLE 19-3

| Liquid chromatograph | Agilent 1260 | |
|---|---|---|
| Chromatography column | YMC Triart C18 150 × 4.6 mm, 3 μm | |
| Mobile phase | A: 0.1% FA in $H_2O$<br>B: ACN | |
| Elution gradient | Time (min) | % B |
| | 0.0 | 25 |
| | 15.0 | 50 |
| | 15.1 | 90 |
| | 18.0 | 90 |
| | 18.1 | 25 |
| | 22.0 | 25 |
| Run time | 22.0 min | |
| Flow rate of mobile phase | 1.0 mL/min | |
| Injection volume | 5 μL | |
| Detection wavelength | UV at 254 nm | |
| Column temperature | 30° C. | |
| Injector temperature | RT | |
| Diluent | ACN | |

5. Dynamic Vapor Sorption (DVS):

Dynamic vapor sorption (DVS) curves are acquired on a DVS Intrinsic in SMS (Surface Measurement System). The relative humidity at 25° C. is corrected with the deliquescence points of LiCl, $Mg(NO_3)_2$ and KCl. The DVS test parameters are listed in Table 19-4 below:

TABLE 19-4

| Parameter | Set value |
|---|---|
| Temperature | 25° C. |
| Sample amount | 10-20 mg |
| Protective gas and flow | $N_2$, 200 mL/min |
| dm/dt | 0.002%/min |
| Minimum dm/dt equilibration time | 10 min |
| Maximum equilibrium of time | 180 min |
| RH range | 0% RH-95% RH |
| RH gradient | 10% (0% RH-90% RH, 90% RH-0% RH)<br>5% (90% RH-95% RH, 95% RH-90% RH) |

6. Polarizing Microscope (PLM)

The polarizing microscope data are acquired by an Axio Lab. A1 upright microscope at room temperature.

7. High Performance Liquid Chromatography/Ion Chromatography (HPLC/IC):

In the tests, the purity, dynamic solubility and stability are tested by an Agilent 1260 high-performance liquid chromatograph, a molar ratio of salt-forming ions is tested by an ion chromatography, and the analysis conditions are shown in Tables 19-5 and 19-6 below:

TABLE 19-5

| High performance liquid chromatography test conditions | | | | |
|---|---|---|---|---|
| Hue spectrometer | Agilent 1260 | | | |
| Chromatography column | YMC Triart C18 150 × 4.6 mm, 3 μm | | | |
| Mobile phase | A: 0.1% FA in $H_2O$<br>B: ACN | | | |
| | Purity | | Solubility | |
| Elution gradient | Time (min) | % B | Time (min) | % B |
| | 0.0 | 25 | 0.0 | 35 |
| | 15.0 | 50 | 5.0 | 90 |
| | 15.1 | 90 | 6.0 | 90 |
| | 18.0 | 90 | 6.1 | 35 |
| | 18.1 | 25 | 8.0 | 35 |
| | 22.0 | 25 | — | — |
| Run time | 22.0 min | | 8.0 min | |
| Flow rate of mobile phase | 1.0 mL/min | | | |
| Injection volume | 5 μL | | | |
| Detection wavelength | UV at 254 nm | | | |
| Column temperature | 30° C. | | | |
| Injector temperature | RT | | | |
| Diluent | ACN | | ACN/$H_2O$ = 1:1 (v/v) | |

TABLE 19-6

| Ion chromatography test conditions | |
|---|---|
| Ion chromatography instrument | ThermoFisher ICS-1100 |
| Chromatography column | IonPac AS18 Analytical Column, 250*4 mm |
| Mobile phase | 25 mM NaOH |
| Injection volume | 25 μL |
| Flow rate | 1.0 mL/min |
| Temperature | 35° C. |
| Column temperature | 35° C. |
| Current | 80 mA |
| Run time | Chloride ion 7.0 min, sulfate ion 11.0 min, bromide ion 15.0 min, and phosphate ion 40.0 min |

Example 1: Preparation of the Compound of Formula (I)

(R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (target compound I)

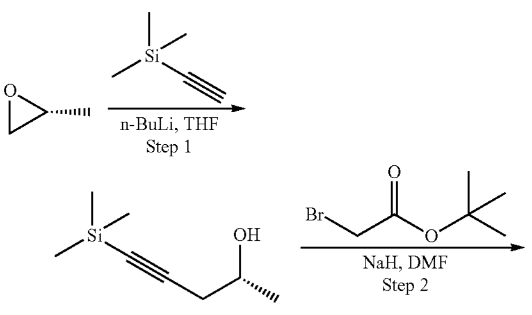

5A

-continued

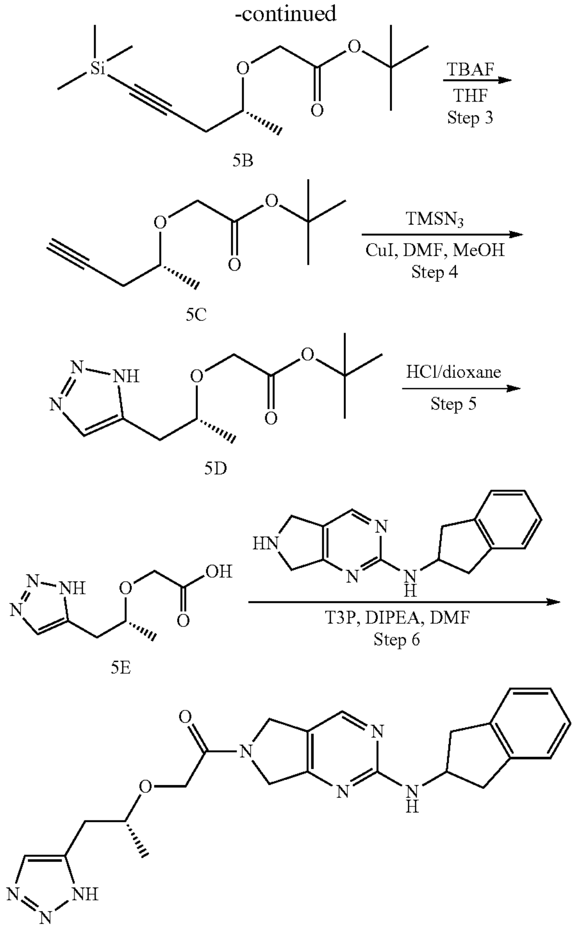

I

Step 1: Synthesis of (R)-5-(trimethylsilyl)pent-4-yn-2-ol (5A)

5A

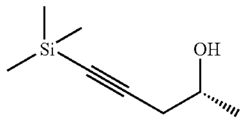

Trimethylsilylacetylene (51.7 g) and diethyl ether (600 mL) were added in a three-necked flask, cooled to −78° C. under nitrogen atmosphere, and added slowly dropwise with n-butyllithium (2.5 M, 217 mL). After the addition was completed, the reaction liquid was reacted for 1 h with −78° C. maintained, added with a solution of boron trifluoride in tetrahydrofuran (50%, 30 mL), and then added slowly dropwise with (R)-propylene oxide (30 g). After the addition was completed, the reaction liquid was stirred for 1 h with the temperature maintained, and added with a saturated aqueous sodium bicarbonate solution (300 mL) to quench the reaction. After the reaction liquid was warmed to room temperature, the liquid separation was conducted, the organic phase was dried, stirred with silica gel, and separated and purified with silica gel column (petroleum ether:

ethyl acetate (V/V)=10:1) to obtain a pale yellow liquid compound (R)-5-(trimethylsilyl)pent-4-yn-2-ol (5A) as a product (34 g, yield: 42.1%).

Step 2: Synthesis of tert-butyl (R)-2-((5-(trimethylsilyl)pent-4-yn-2-yl)oxy)acetate (5B)

5B

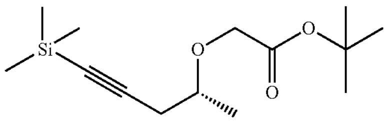

The starting material (R)-5-(trimethylsilyl)pent-4-yn-2-ol (34 g, 218 mmol) was added into 340 mL of dry tetrahydrofuran. The mixture was cooled to 0° C., added with 60% NaH (10.44 g, 261 mmol), and stirred for 30 min. The mixture was added with the starting material tert-butyl 2-bromoacetate (46.7 g, 239 mmol) at 0° C., naturally warmed to room temperature, and stirred for 16 h. Methanol (20 mL) was added to the reaction liquid at 0° C., and the mixture was stirred with silica gel, concentrated, and separated and purified by silica gel column (petroleum ether: ethyl acetate (V/V)=10:1) to obtain a pale yellow liquid compound tert-butyl (R)-2-((5-(trimethylsilyl)pent-4-yn-2-yl)oxy)acetate (5B) (50 g, yield: 85%).

Step 3: Synthesis of tert-butyl (R)-2-(pent-4-yn-2-yloxy)acetate (5C)

5C

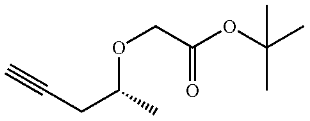

The starting material tert-butyl (R)-2-((5-(trimethylsilyl)pent-4-yn-2-yl)oxy)acetate (50 g, 185 mmol) was added into 500 mL of tetrahydrofuran at room temperature, and then the mixture was added with tetrabutylammonium fluoride (53.2 g, 203 mmol), and reacted at room temperature for 15 h. The reaction liquid was stirred with silica gel and concentrated, and the residue was separated and purified by silica gel column (petroleum ether:ethyl acetate (V/V)=10:1) to obtain the title yellow liquid compound tert-butyl (R)-2-(pent-4-yn-2-yloxy)acetate (27 g, 73.7%).

Step 4: Synthesis of tert-butyl (R)-2-((1-(1H-1,2,3-triazol-5-yl)propan-2-yl)oxy)acetate (5D)

5D

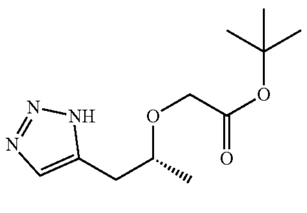

The starting material tert-butyl (R)-2-(pent-4-yn-2-yloxy) acetate (27 g, 136 mmol) was added into 150 mL of DMF and 20 mL of methanol at room temperature, and the mixture was added with azidotrimethylsilane (23.53 g, 204 mmol) and copper(I) iodide (2.08 g, 10.89 mmol) under nitrogen atmosphere. The reaction liquid was heated to 90° C. and stirred for 15 h. The reaction liquid was cooled to 40° C., concentrated to dryness, diluted with dichloromethane and stirred with silica gel, and concentrated. The residue was separated and purified by silica gel column (petroleum ether:ethyl acetate (V/V)=1:1) to obtain a yellow oily compound tert-butyl (R)-2-((1-(1H-1,2,3-triazol-5-yl)propan-2-yl)oxy)acetate (14 g, 42.6%).

Step 5: Synthesis of (R)-2-((1-(1H-1,2,3-triazol-5-yl)propan-2-yl)oxy)acetic acid (5E)

5E

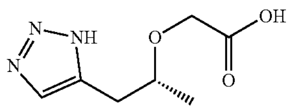

The starting material tert-butyl (R)-2-((1-(1H-1,2,3-triazol-5-yl)propan-2-yl)oxy)acetate (14 g, 58 mmol) was added hydrogen chloride in 1,4-dioxane (4 mol/L, 70 mL) at room temperature, and the mixture was stirred at room temperature for 16 h and filtered. The resulting solid was washed with methyl tert-butyl ether and dried to obtain a white solid (R)-2-((1-(1H-1,2,3-triazol-5-yl)propan-2-yl) oxy)acetic acid (9.2 g, 86%).

Step 6: Synthesis of (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (target compound I)

I

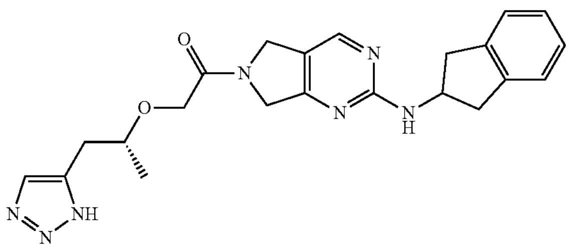

The starting material (R)-2-((1-(1H-1,2,3-triazol-5-yl) propan-2-yl)oxy)acetic acid (9.41 g, 42.5 mmol) and N-(2,3-dihydro-1H-inden-2-yl)-6,7-dihydro-5H-pyrrolo[3,4-d] pyrimidin-2-amine (9.2 g, 28.3 mmol) were added into 1000 mL of DMF at room temperature. The mixture was added with T3P (50% DMF solution) (27 g, 42.5 mmol) and diisopropylethylamine (21.95 g, 170 mmol) at 0° C., naturally warmed to room temperature, and stirred for 16 h. The reaction liquid was filtered, and the filtrate was added with water (3 mL), and concentrated to dryness. The residue was separated and purified by silica gel column (dichloromethane:methanol (V/V)=10:1) to obtain 12 g of crude product, slurried with 120 mL of isopropyl acetate for 10 h, filtered and dried to obtain (R)-2-((1-(1H-1,2,3-triazol-5-yl)propan- 2-yl)oxy)-1-(2-((2,3-dihydro-1H-inden-2-yl)amino)-5,7-dihydro-6H-pyrrolo[3,4-d]pyrimidin-6-yl)ethan-1-one (7.8 g, HPLC purity: 98.63%, ee value >99%, yield: 65.7%).

$^1$H NMR (400 MHz, DMSO-d6) δ 8.30 (d, 1H), 7.64 (b, 1H), 7.57 (t, 1H), 7.22-7.20 (m, 2H), 7.16-7.12 (m, 2H), 4.65-4.59 (m, 3H), 4.52 (s, 1H), 4.42 (s, 1H), 4.25-4.17 (m, 2H), 3.87-3.81 (m, 1H), 3.27-3.21 (m, 2H), 2.90-2.85 (m, 4H), 1.19 (t, 3H).

LC-MS, M/Z (ESI): 420.4 (M+1).

Example 2: Preparation of Salt of the Compound of Formula (I) and Crystal Form Thereof About 15 mg of the starting material free base compound of formula (I) was stirred with an equimolar ratio of the corresponding inorganic or organic acid in 0.5 mL of solvent at room temperature for 3 days. The clear sample was transferred to a condition with a temperature of 5° C. and stirred; if there was still no solid precipitated, the sample was suspended and stirred at −20° C., and then transferred to a condition with room temperature for evaporating. The sample was centrifuged to obtain the salt of the compound of formula (I), wherein the salt was present in crystal form.

The used inorganic acid or organic acid, solvent and the obtained 14 salts and 18 crystal forms are shown Table 20 below.

TABLE 20

Inorganic acid or organic acid, solvents and the resulting salt of the compound of formula (I) and the crystal form of the salt used

| Nos. | Inorganic acid or organic acid | Solvent | Salt of the compound of formula (I) | Crystal form of the salt of the compound of formula (I) |
|---|---|---|---|---|
| 1 | Hydrochloric acid | Acetone or ethyl acetate | hydrochloride | Crystal form A of hydrochloride |
| 2 | Sulfuric acid | Ethanol or acetone or ethyl acetate | Sulfate | Crystal form A of sulfate |
| 3 | Maleic acid | Ethyl acetate or acetonitrile | Maleate | Crystal form A of maleate |
| 4 | Phosphoric acid | Ethanol or acetone | Phosphate | Crystal form A of phosphate |
| 5 | L-tartaric acid | Ethanol | Tartrate | Crystal form A of tartrate |
| 6 | L-tartaric acid | Ethyl acetate | Tartrate | Crystal form B of tartrate |
| 7 | L-tartaric acid | Acetonitrile | Tartrate | Crystal form C of tartrate |
| 8 | Fumaric acid | Ethanol or acetone or ethyl acetate or acetonitrile | Fumarate | Crystal form A of fumarate |
| 9 | Citric acid | Ethanol or acetone | Citrate | Crystal form A of citrate |
| 10 | Glycolic acid | Acetone or acetonitrile | Glycolate | Crystal form A of glycolate |
| 11 | Succinic acid | Ethanol or acetone | Succinate | Crystal form A of succinate |
| 12 | Succinic acid | Ethyl acetate or acetonitrile | Succinate | Crystal form B of succinate |
| 13 | Adipic acid | Acetonitrile | Adipate | Crystal form B of adipate |
| 14 | Sebacic acid | Ethyl acetate | Sebacate | Crystal form A of sebacate |
| 15 | p-Toluenesulfonic acid | Ethanol or acetone or ethyl acetate or acetonitrile | p-toluenesulfonate | Crystal form A of p-toluenesulfonate |
| 16 | Benzenesulfonic acid | Acetone or acetonitrile | Benzenesulfonate | Crystal form A of benzenesulfonate |
| 17 | Hydrobromic acid | Acetone | Hydrobromide | Crystal form A of hydrobromide |
| 18 | Hydrobromic acid | Acetonitrile | Hydrobromide | Crystal form B of hydrobromide |

Example 3: Evaluation of Crystal Form of Salt of the Compound of Formula (I)

According to the characterization results (higher crystallinity, smaller TGA weight loss, less and sharp DSC endothermic peak) of each salt form and the common use and safety grade of acid, the crystal form A of hydrochloride, the crystal form A of fumarate and the crystal form A of benzenesulfonate were selected for the next evaluation. XRPD, TGA, DSC, NMR or HPLC/IC characterization of each sample prepared was summarized in Table 21-1 below:

TABLE 21-1

Summary of characterization of the crystal form of the salt of the compound of formula (I)

| Salt form | TGA weight loss (%, 150° C.) | DSC endothermic peak (° C., peak temperature) | Molar ratio (acid/base) |
|---|---|---|---|
| Crystal form A of hydrochloride | 4.7 | 171.5 | 1.1 |
| Crystal form A of fumarate | 1.7 | 210.7 | 1.0 |
| Crystal form A of benzenesulfonate | 1.7 | 188.4 | 1.0 |

Salt form evaluation was performed using 3 salt forms prepared repeatedly, and non-salt and non-solvate crystal form A of the compound of formula (I) (also referred to as free base crystal form A) was selected for comparison, and evaluation items included hygroscopicity, polarizing microscope (PLM) image, dynamic solubility and solid stability.

In the above evaluation, the 2θ diffraction angle, D-value and/or relative intensity of the X-ray powder diffraction pattern using Cu-Kα radiation by the free base crystal form A are shown in Table 21-2 below:

TABLE 21-2

XRPD diffraction peak data for free base crystal form A

| No. | Position [°2θ] | D-spacing [A] | Relative intensity [%] |
|---|---|---|---|
| 1 | 8.05 | 10.98 | 98.24 |
| 2 | 8.30 | 10.65 | 72.21 |
| 3 | 10.77 | 8.21 | 6.26 |
| 4 | 12.95 | 6.84 | 5.30 |
| 5 | 14.11 | 6.28 | 56.08 |
| 6 | 16.18 | 5.48 | 95.94 |
| 7 | 16.65 | 5.33 | 31.47 |
| 8 | 17.35 | 5.11 | 5.54 |
| 9 | 18.19 | 4.88 | 10.77 |
| 10 | 18.91 | 4.69 | 13.34 |

TABLE 21-2-continued

| XRPD diffraction peak data for free base crystal form A | | | |
|---|---|---|---|
| No. | Position [°2θ] | D-spacing [A] | Relative intensity [%] |
| 11 | 19.19 | 4.62 | 16.46 |
| 12 | 20.93 | 4.24 | 4.90 |
| 13 | 21.53 | 4.13 | 8.01 |
| 14 | 21.85 | 4.07 | 23.12 |
| 15 | 22.31 | 3.98 | 9.50 |
| 16 | 22.73 | 3.91 | 100.00 |
| 17 | 24.38 | 3.65 | 5.74 |
| 18 | 25.16 | 3.54 | 90.33 |
| 19 | 26.23 | 3.40 | 28.43 |
| 20 | 27.39 | 3.26 | 3.84 |
| 21 | 28.44 | 3.14 | 2.64 |
| 22 | 28.99 | 3.08 | 8.12 |
| 23 | 29.20 | 3.06 | 8.98 |
| 24 | 29.91 | 2.99 | 13.34 |
| 25 | 32.77 | 2.73 | 1.53 |
| 26 | 36.68 | 2.45 | 1.55 |

Figure 40:
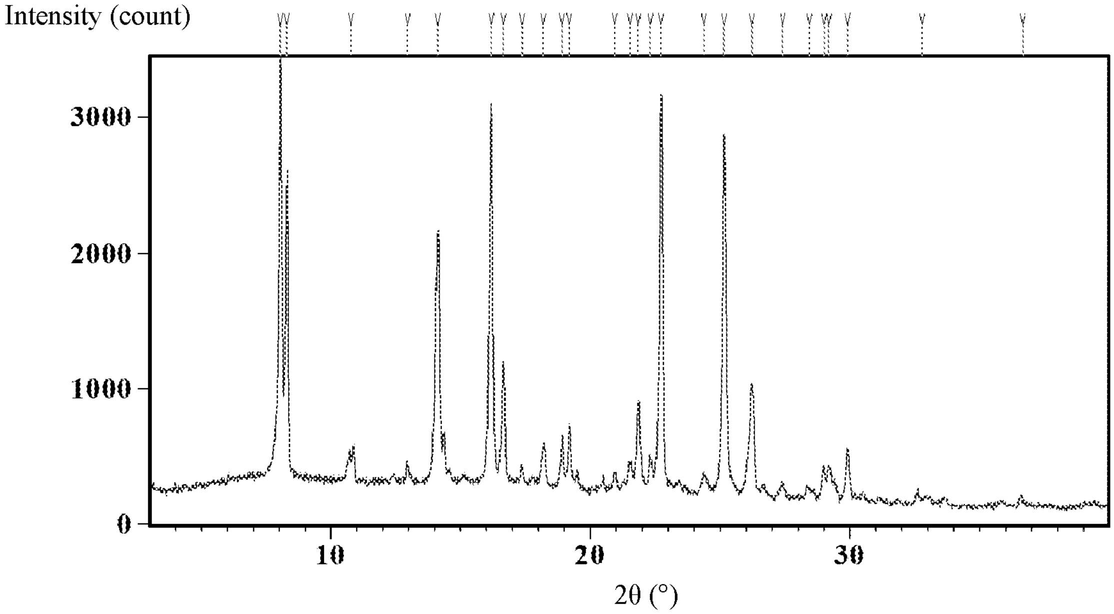
FIG. 40 is an XRPD pattern (instrument 1) of the free base crystal form A of the compound of formula (I)
Figure 41:
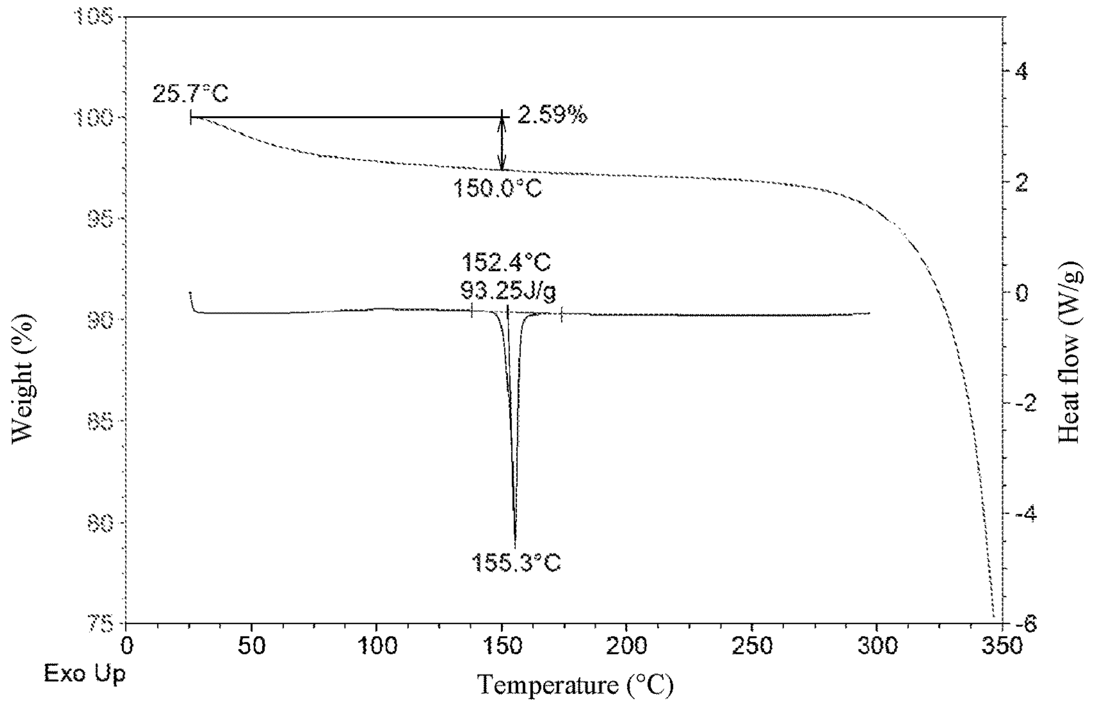
FIG. 41 is a TGA/DSC pattern of the free base crystal form A of the compound of formula (I)
Figure 42:
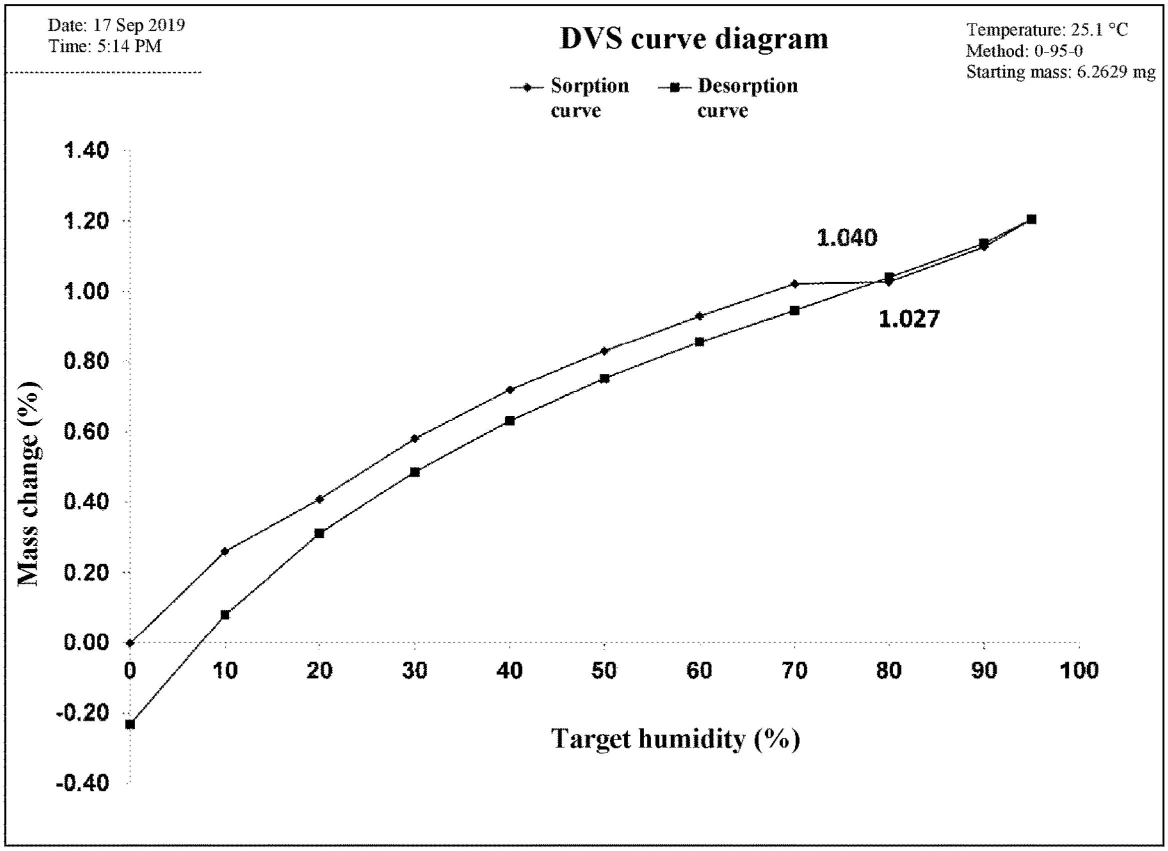
FIG. 42 is a DVS pattern of the free base crystal form A of the compound of formula (I)

The free base crystal form A had an X-ray powder diffraction pattern substantially as shown in FIG. 40, had TGA and DSC curves substantially as shown in FIG. 41, and had DVS curves substantially as shown in FIG. 42.

3.1 Hygroscopicity

Hygroscopicity of the crystal form A of hydrochloride, the crystal form A of fumarate, the crystal form A of benzenesulfonate and the free base crystal form A prepared repeatedly was evaluated using a dynamic vapor sorption (DVS) instrument. Starting at 0% relative humidity (0% RH), the test acquired the percentage change of mass of the sample when humidity changed (0% RH to 95% RH to 0% RH) at a constant temperature of 25° C. The DVS evaluation results were summarized in Table 21-3 below, and the results show that the crystal form A of hydrochloride had hygroscopicity and changed crystal form after DVS test, and other samples had slight hygroscopicity and no polymorphic transition occurred after DVS test.

TABLE 21-3

| Evaluation results of hygroscopicity | | | | |
|---|---|---|---|---|
| Salt form | Vapor sorption (25° C./80% RH) | Hygroscopicity | After DVS test Whether the crystal form is changed | Risk evaluation |
| Crystal form A of hydrochloride | 3.85% | Moderately hygroscopic | Yes* | Significantly increased vapor sorption at high humidity |
| Crystal form A of fumarate | 0.60% | Slightly hygroscopic | No | None |
| Crystal form A of benzenesulfonate | 1.45% | Slightly hygroscopic | No | None |
| Free base crystal form A | 1.03% | Slightly hygroscopic | No | None |

*transformed into a new crystal form 3.2 Polarizing Microscope (PLM) Image

Polarizing microscope (PLM) image characterization was performed on the crystal form A of hydrochloride, the crystal form A of fumarate, the crystal form A of benzenesulfonate and the free base crystal form A prepared repeatedly, wherein each sample had a particle size of less than 50 μm.

3.3 Dynamic Solubility

The dynamic solubility of the crystal form A of hydrochloride, the crystal form A of fumarate, the crystal form A of benzenesulfonate and the free base crystal form A prepared repeatedly was evaluated in water and three biological vehicles. The dynamic solubility (1 h, 4 h and 24 h) of each sample in the four solvent systems of water, SGF, FaSSIF and FeSSIF 1 was determined at a feed concentration of 5 mg/mL (20 mg of material in 4 mL of solvent) by rotary mixing (25 rpm) at 37° C. After centrifugation of the samples at each time point (0.45 μm PTFE filter head), the filtrate was determined for HPLC concentration and pH, and the centrifuged solid samples were tested for XRPD. The solubility test results were summarized in Table 21-4 below, and the results show that the solubility of the crystal form A of hydrochloride and the crystal form A of benzenesulfonate in each system was significantly improved compared with that of the free base crystal form A.

TABLE 21-4

Summary of dynamic solubility test results

| Starting material | Solvent | 1 h S | 1 h pH | 1 h Crystal form change | 4 h S | 4 h pH | 4 h Crystal form change | 24 h S | 24 h pH | 24 h Crystal form change |
|---|---|---|---|---|---|---|---|---|---|---|
| Crystal | $H_2O$ | 2.0 | 2.3 | NA | 2.2 | 2.2 | NA | 2.2 | 2.3 | NA |
| form A of | SGF | 2.9 | 1.8 | NA | 3.8 | 1.8 | NA | 4.7 | 1.9 | NA |
| hydrochloride | FaSSIF | 0.5 | 5.7 | NA | 0.5 | 5.5 | NA | 0.5 | 5.2 | NA |
| | FeSSIF | 0.5 | 4.9 | NA | 0.7 | 4.9 | NA | 1.3 | 4.9 | NA |
| Crystal | $H_2O$ | 0.3 | 3.6 | No | 0.4 | 3.7 | No | 0.1 | 3.6 | No |
| form A of | SGF | 0.6 | 1.9 | No | 0.7 | 1.9 | No | 0.8 | 1.9 | No |
| fumarate | FaSSIF | 0.5 | 4.9 | NA | 0.5 | 4.4 | NA | 0.3 | 4.2 | NA |
| | FeSSIF | 1.3 | 4.8 | NA | 1.3 | 4.9 | NA | 1.3 | 4.8 | NA |
| Benzenesulfonate | $H_2O$ | 1.5 | 2.5 | NA | 1.7 | 2.5 | NA | 1.5 | 2.5 | NA |
| Crystal | SGF | 3.2 | 1.9 | No | >3.3 | 1.9 | Clear | >3.3 | 1.9 | Clear |
| form | FaSSIF | 0.5 | 6.0 | NA | 0.5 | 6.0 | NA | 0.5 | 6.0 | NA |
| | FeSSIF | 0.8 | 5.0 | NA | 1.0 | 5.0 | NA | 1.2 | 5.0 | NA |
| Free base | $H_2O$ | 0.1 | 8.4 | No | 0.1 | 8.4 | No | 0.1 | 8.6 | No |
| crystal | SGF | 0.9 | 1.9 | No | 0.9 | 1.9 | No | 0.9 | 2.0 | No |
| form A | FaSSIF | 0.1 | 6.5 | No | 0.1 | 6.6 | No | 0.1 | 6.6 | No |
| | FeSSIF | 0.2 | 5.1 | No | 0.2 | 5.1 | No | 0.2 | 5.1 | No |

3.4 Solid Stability

The crystal form A of hydrochloride, the crystal form A of fumarate, the crystal form A of benzenesulfonate and the free base crystal form A prepared repeatedly were placed at 25° C./60% RH and 40° C./75% RH for 1 week, and then the physical and chemical stability of the samples were tested by XRPD and HPLC. The stability evaluation results were summarized in Table 21-5 below, and the results show that the crystal form A of hydrochloride had decreased HPLC purity and decreased XRPD crystallinity after being placed at 40° C./75% RH for 1 week. No significant purity decrease or crystal form transformation occurred in any of the other samples after being placed under 2 conditions for 1 week.

TABLE 21-5

Summary of evaluation of solid stability

| Starting sample | Condition | Time point | Purity (area %) | Purity/ initial purity (%) | Crystal form change |
|---|---|---|---|---|---|
| Crystal | Starting | — | 97.16 | — | — |
| form A of | 25° C./60% RH | 1 week | 96.68 | 99.5 | No |
| hydrochloride | 40° C./75% RH | 1 week | 77.67 | 79.9 | No* |
| Crystal | Starting | — | 99.22 | — | — |
| form A of | 25° C./60% RH | 1 week | 99.28 | 100.1 | No |
| fumarate | 40° C./75% RH | 1 week | 99.33 | 100.1 | No |
| Crystal | Starting | — | 99.34 | — | — |
| form A of | 25° C./60% RH | 1 week | 99.35 | 100.0 | No |
| benzenesulfonate | 40° C./75% RH | 1 week | 99.20 | 99.9 | No |
| Free base | Starting | — | 98.63 | — | — |
| crystal | 25° C./60% RH | 1 week | 98.67 | 100.0 | No |
| form A | 40° C./75% RH | 1 week | 98.60 | 100.0 | No |

*decrease in crystallinity

Further tests show that the crystal form A of benzenesulfonate had excellent stability after being stored for 6 months under the following conditions, with unchanged crystal form:

Condition 1: packaging:polyethylene bag+aluminum foil bag, inspection conditions: 40° C.±2° C./75% RH±5% RH (the aluminum foil bag is made of light-proof materials and can be protected from light; and the polyethylene bag and the aluminum foil bag are sealed when being packaged);

Condition 2: packaging:polyethylene bag+aluminum foil bag, and a desiccant placed between the outer bag and the inner bag, inspection conditions: 25° C.±2° C./60% RH±10% RH (the aluminum foil bag is made of light-proof materials and can be protected from light; and the polyethylene bag and the aluminum foil bag are sealed when being packaged);

Condition 3: packaging:polyethylene bag+aluminum foil bag, and a desiccant placed between the outer bag and the inner bag, inspection conditions: 2° C. to 8° C. (the aluminum foil bag is made of light-proof materials and can be protected from light; and the polyethylene bag and the aluminum foil bag are sealed when being packaged).

3.5 Conclusion

Three salt forms and the free base crystal form A were selected for salt form evaluation. The DVS results showed that the crystal form A of hydrochloride had hygroscopicity and changed crystal form after DVS test, and other samples had slight hygroscopicity and no polymorphic transition occurred after DVS test. The PLM results show that each sample had a particle size of less than 50 μm. The dynamic solubility results show that the solubility of the crystal form A of hydrochloride and the crystal form A of benzenesulfonate in each system was significantly improved compared with that of the free base crystal form A. The solid stability evaluation shows that the crystal form A of hydrochloride had decreased HPLC purity and decreased XRPD crystallinity after being placed at 40° C./75% RH for 1 week, and no significant purity decrease or crystal form transformation occurred in any of the other samples after being placed under 2 conditions for 1 week. Moreover, the crystal form A of benzenesulfonate remained stable crystal form for 6 months under the above conditions.

Example 4: Polymorph Evaluation of Benzenesulfonate of the Compound of Formula (I)

Figure 19:
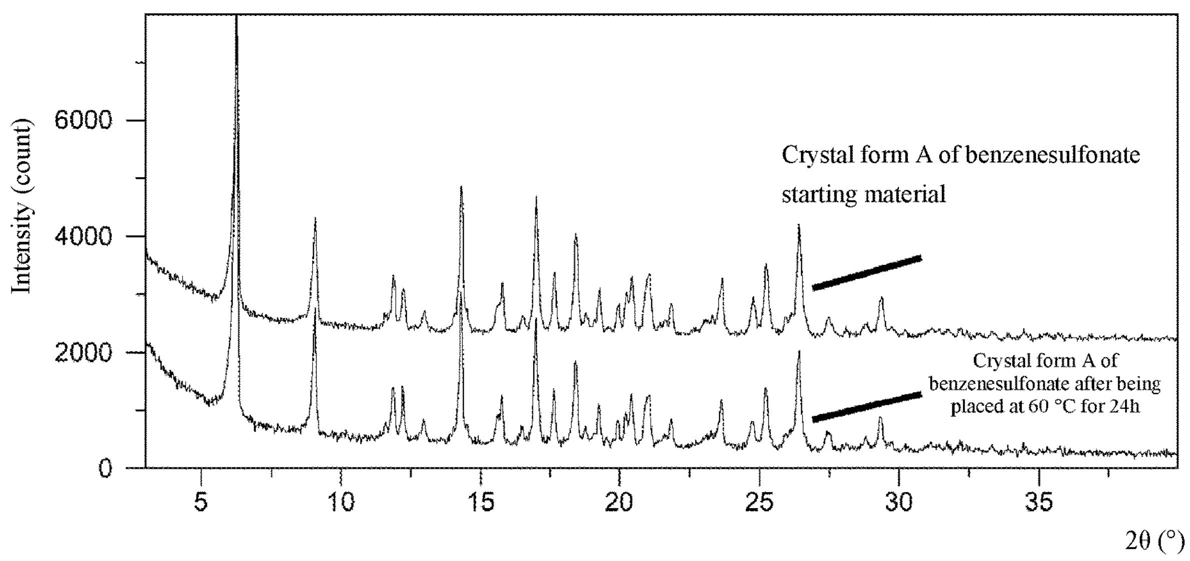
FIG. 19 is an overlay of XRPD patterns (instrument 2) of a sample for evaluating the stability of crystal form A of benzenesulfonate of the compound of formula (I)
Figure 20:
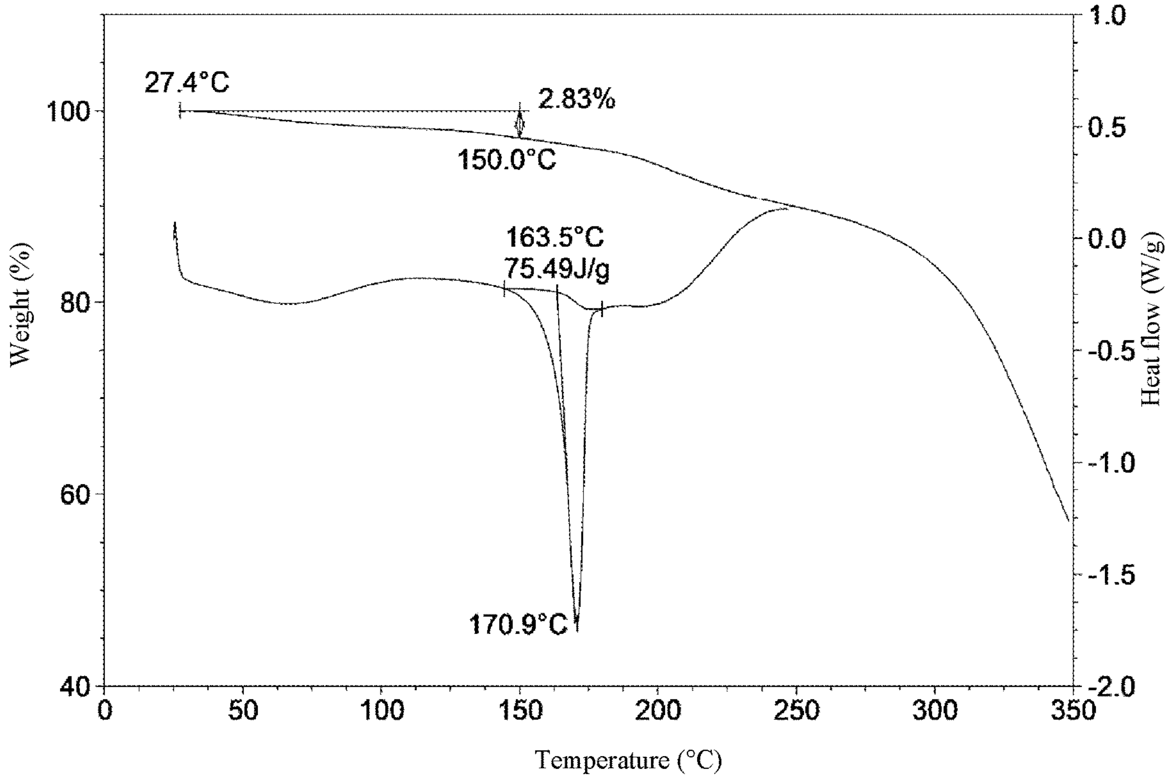
FIG. 20 is a TGA/DSC pattern of the crystal form A of hydrochloride of the compound of formula (I)
Figure 21:
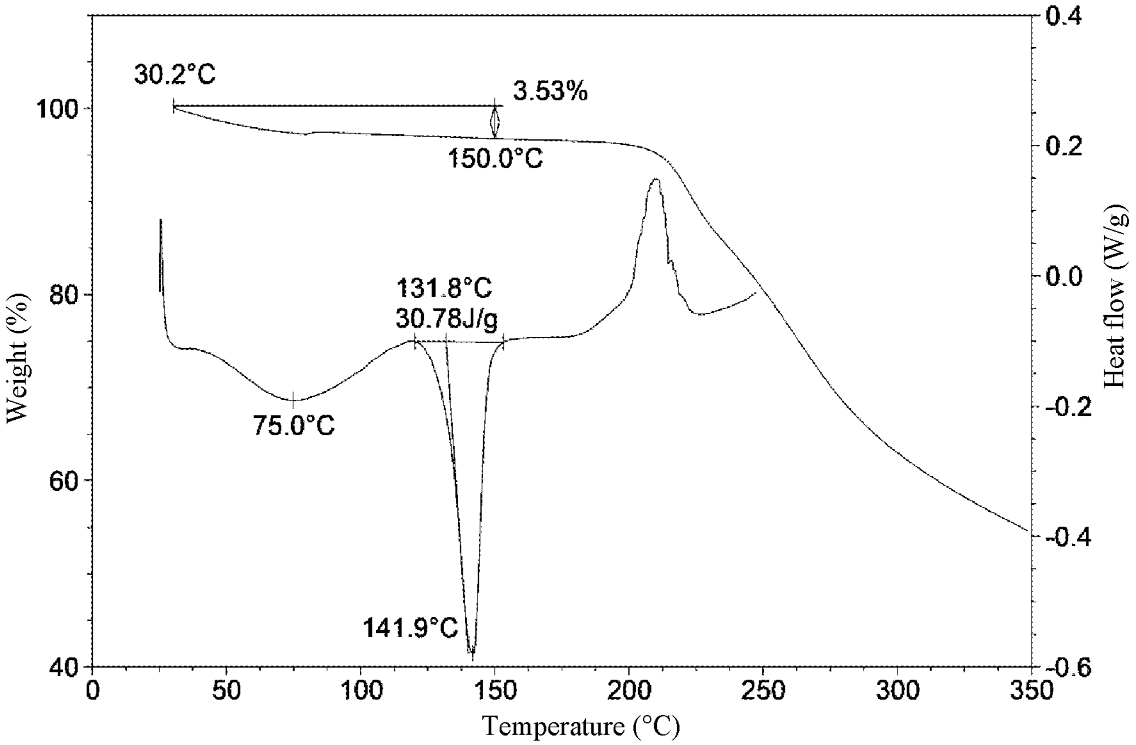
FIG. 21 is a TGA/DSC pattern of the crystal form A of sulfate of the compound of formula (I)
Figure 22:
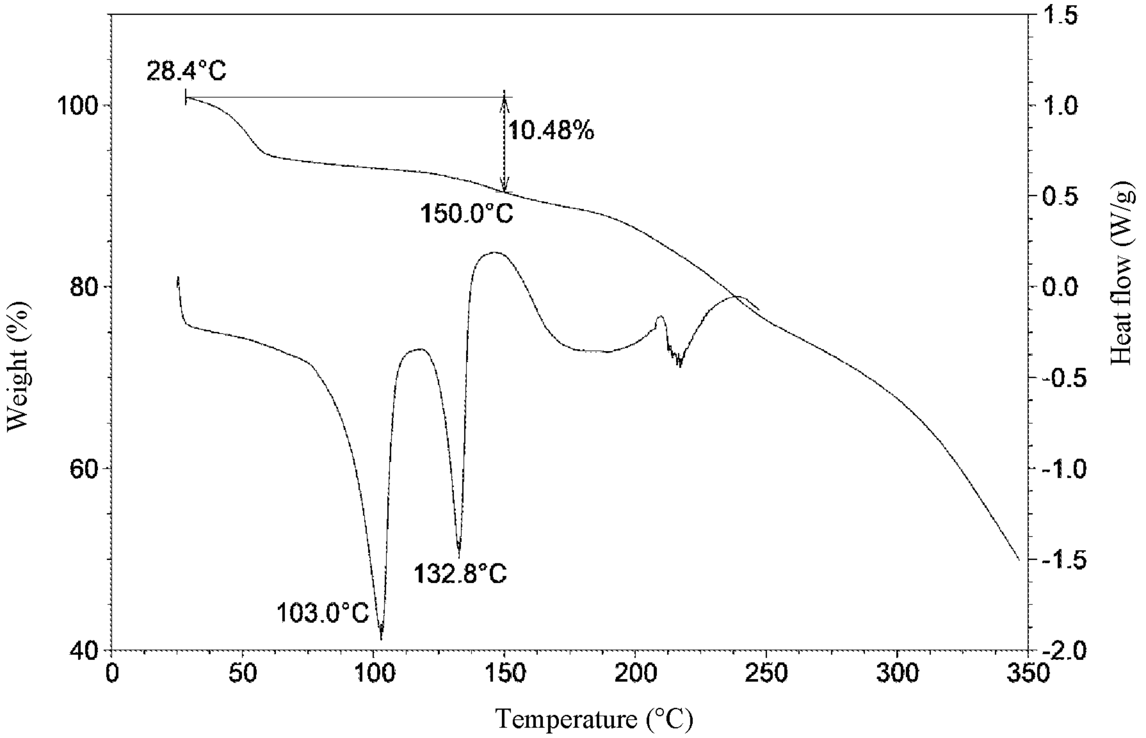
FIG. 22 is a TGA/DSC pattern of the crystal form A of maleate of the compound of formula (I)
Figure 23:
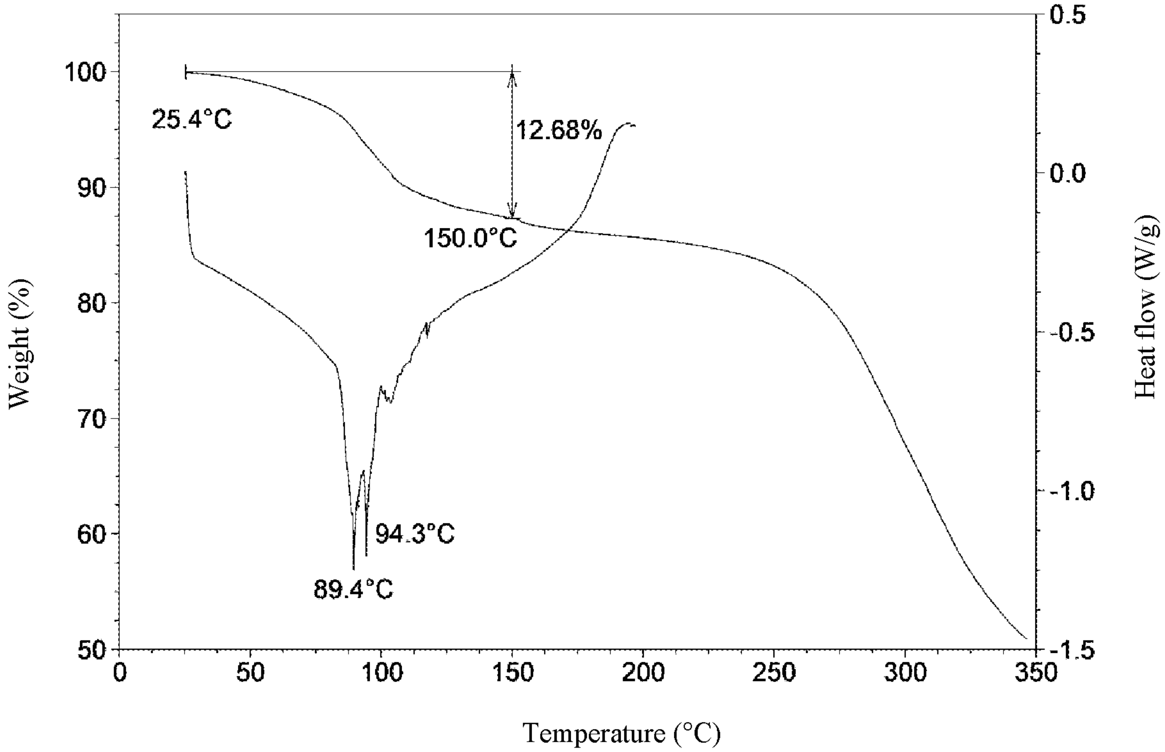
FIG. 23 is a TGA/DSC pattern of the crystal form A of phosphate of the compound of formula (I)
Figure 24:
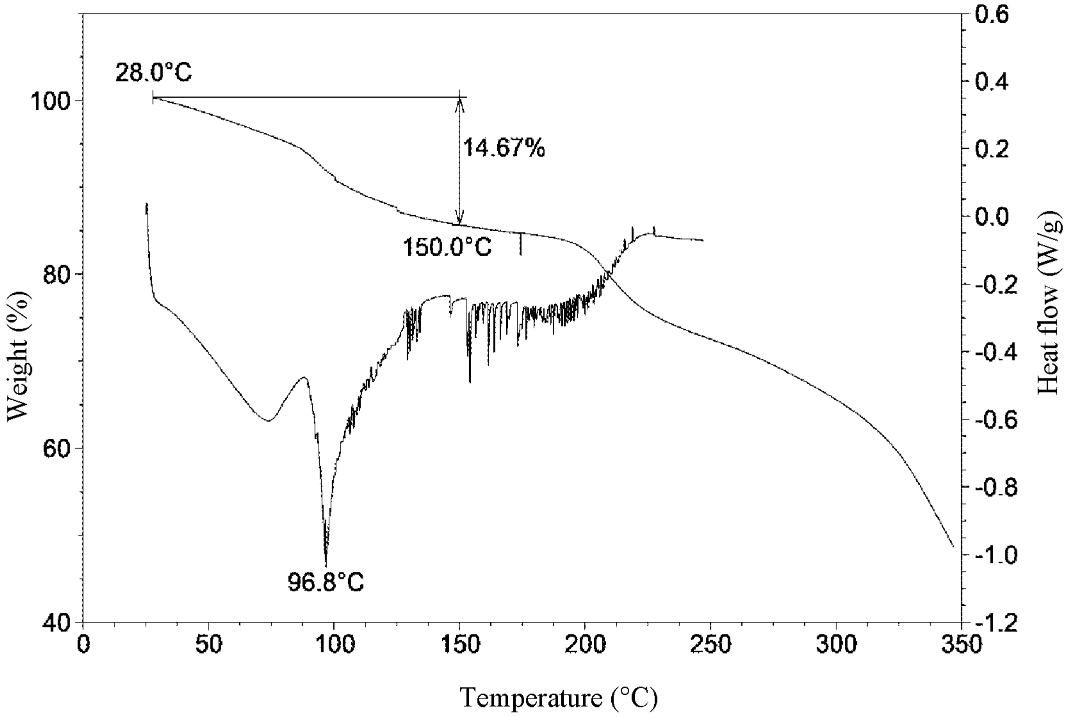
FIG. 24 is a TGA/DSC pattern of the crystal form A of tartrate of the compound of formula (I)
Figure 25:
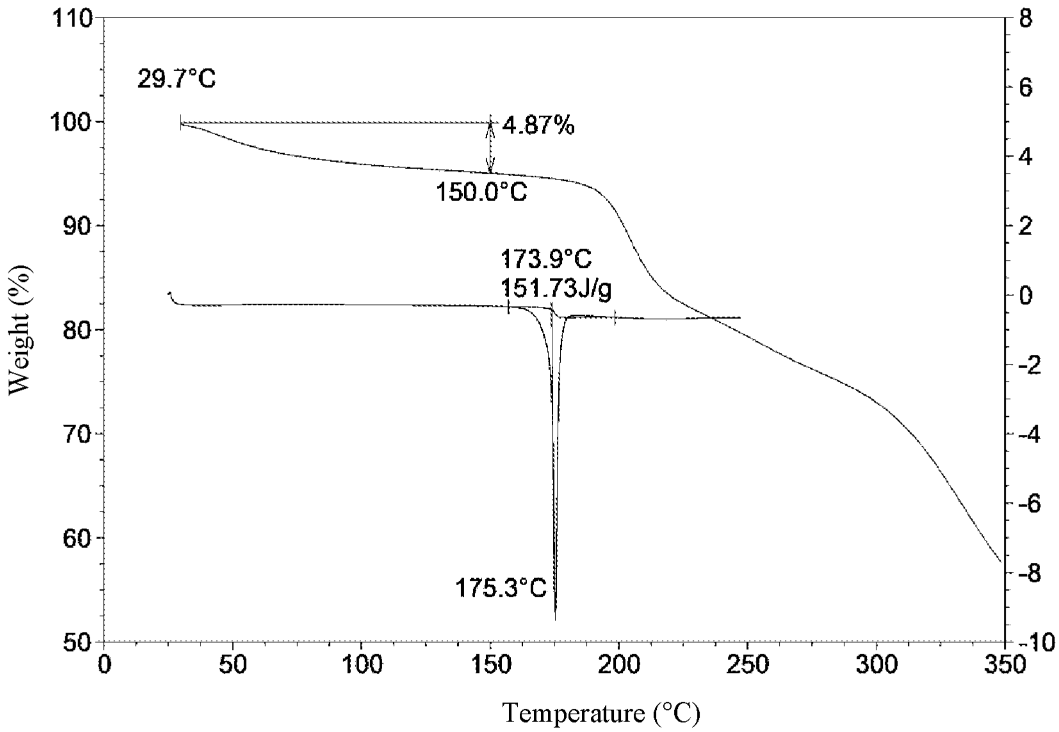
FIG. 25 is a TGA/DSC pattern of the crystal form B of tartrate of the compound of formula (I)
Figure 26:
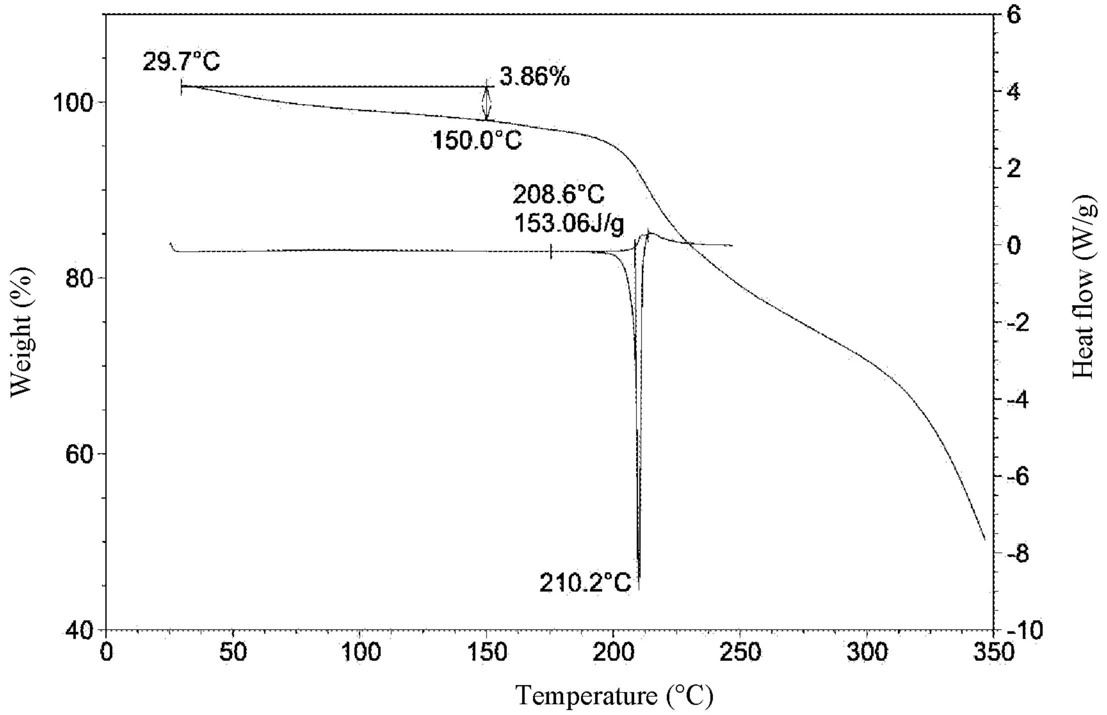
FIG. 26 is a TGA/DSC pattern of the crystal form A of fumarate of the compound of formula (I)
Figure 27:
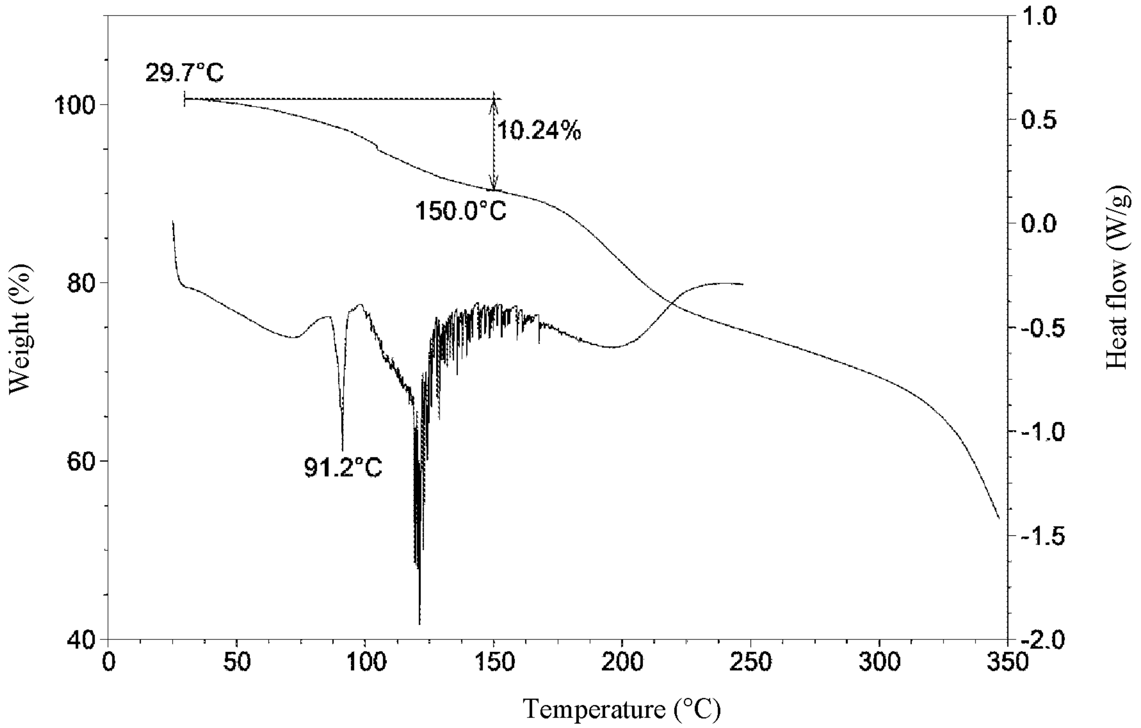
FIG. 27 is a TGA/DSC pattern of the crystal form A of citrate of the compound of formula (I)
Figure 28:
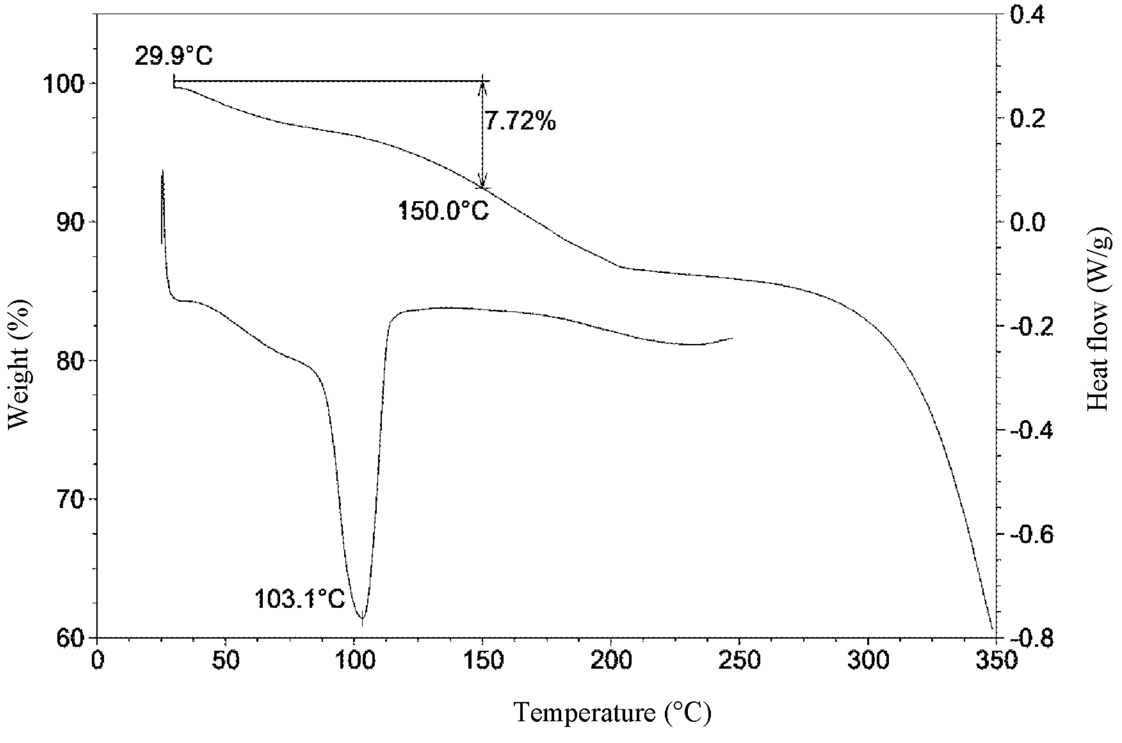
FIG. 28 is a TGA/DSC pattern of the crystal form A of glycolate of the compound of formula (I)
Figure 29:
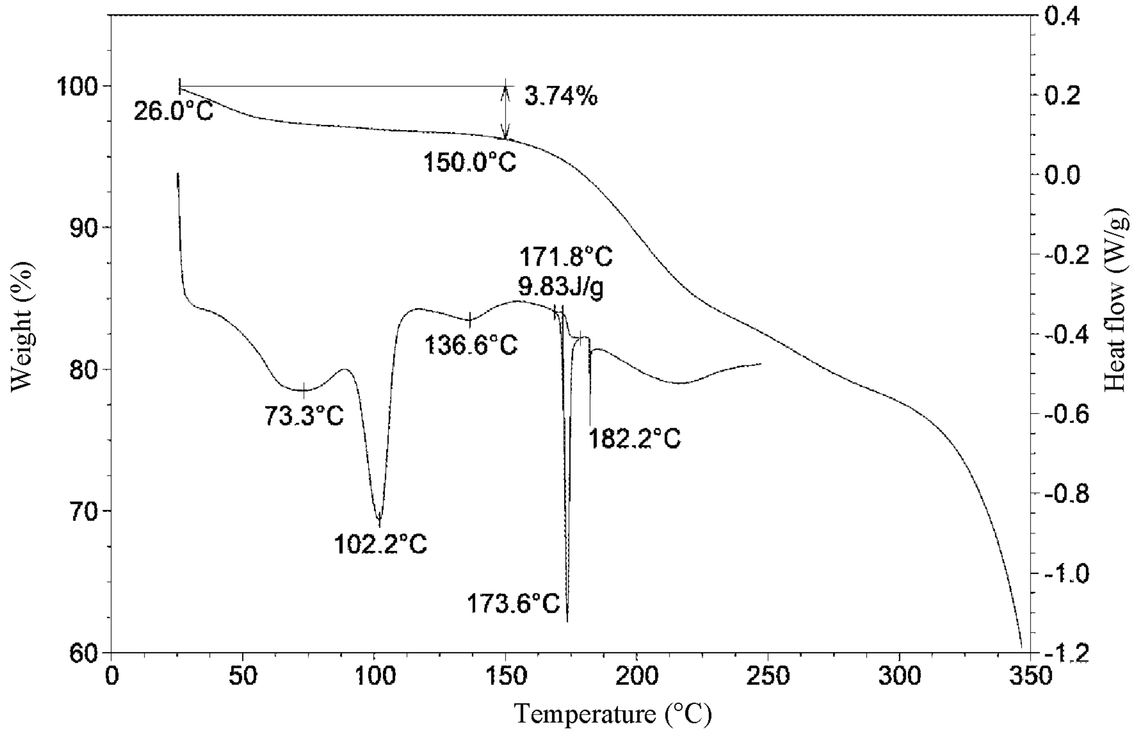
FIG. 29 is a TGA/DSC pattern of the crystal form A of succinate of the compound of formula (I)
Figure 30:
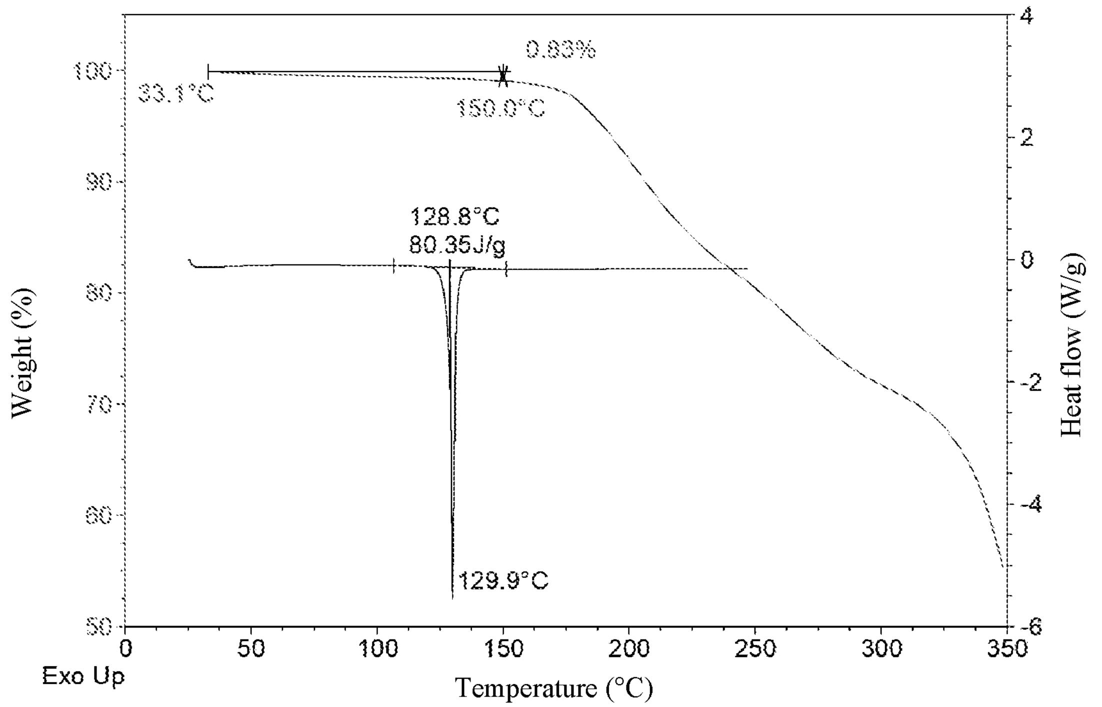
FIG. 30 is a TGA/DSC pattern of the crystal form B of succinate of the compound of formula (I)
Figure 31:
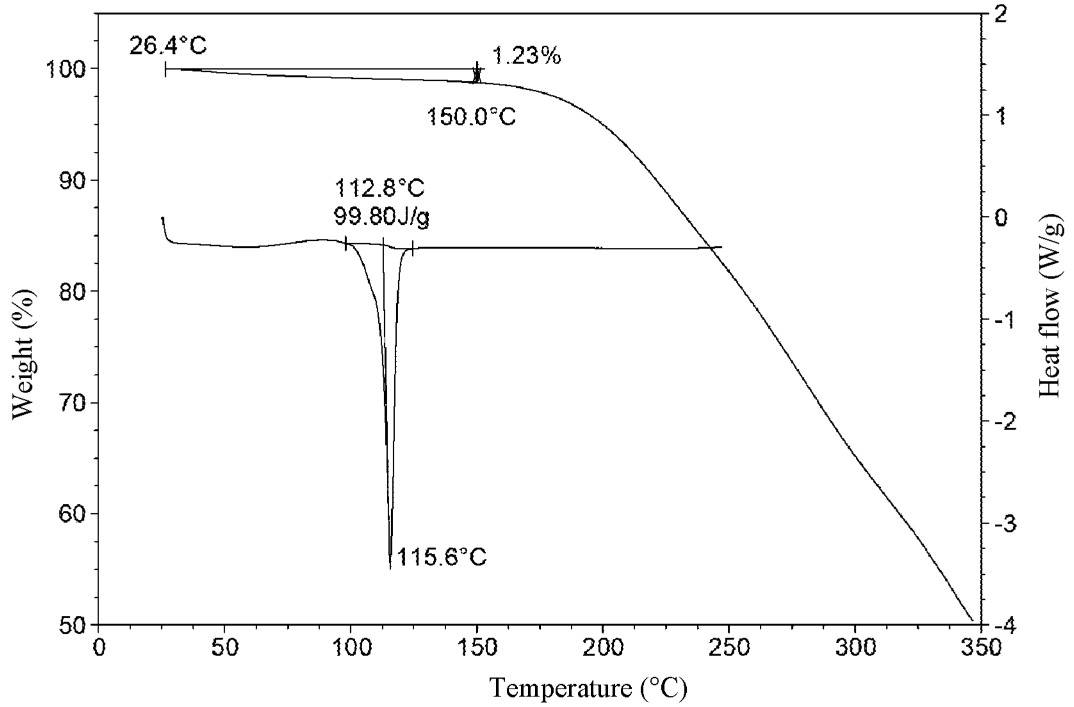
FIG. 31 is a TGA/DSC pattern of the crystal form B of adipate of the compound of formula (I)
Figure 32:
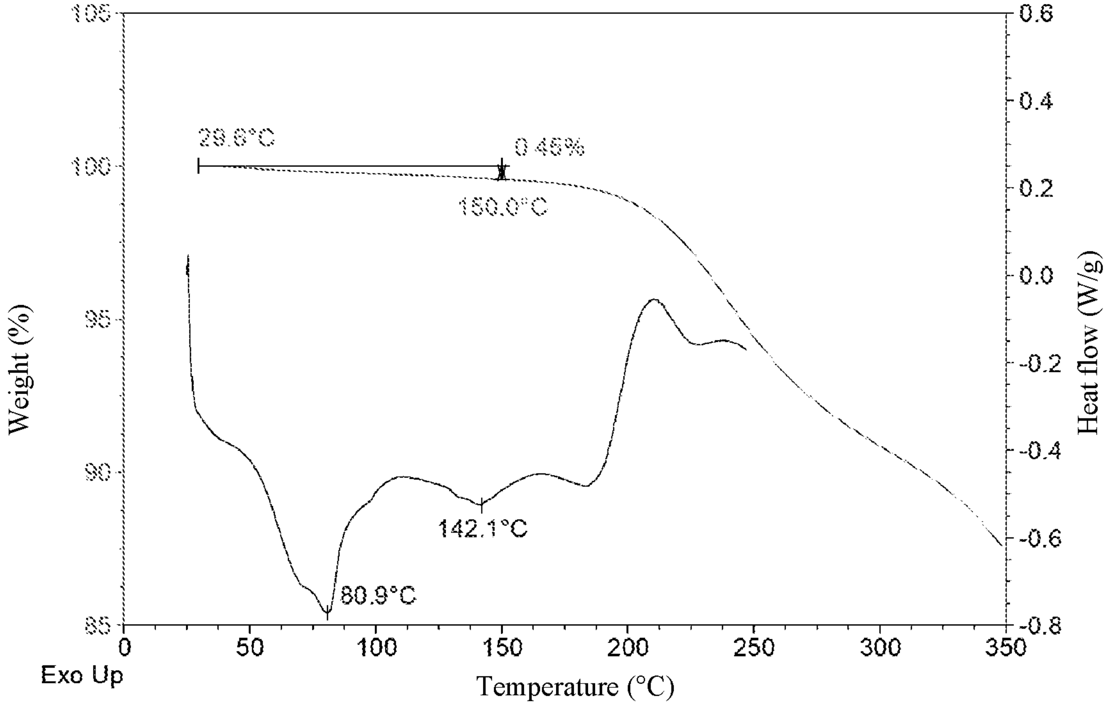
FIG. 32 is a TGA/DSC pattern of the crystal form A of sebacate of the compound of formula (I)
Figure 33:
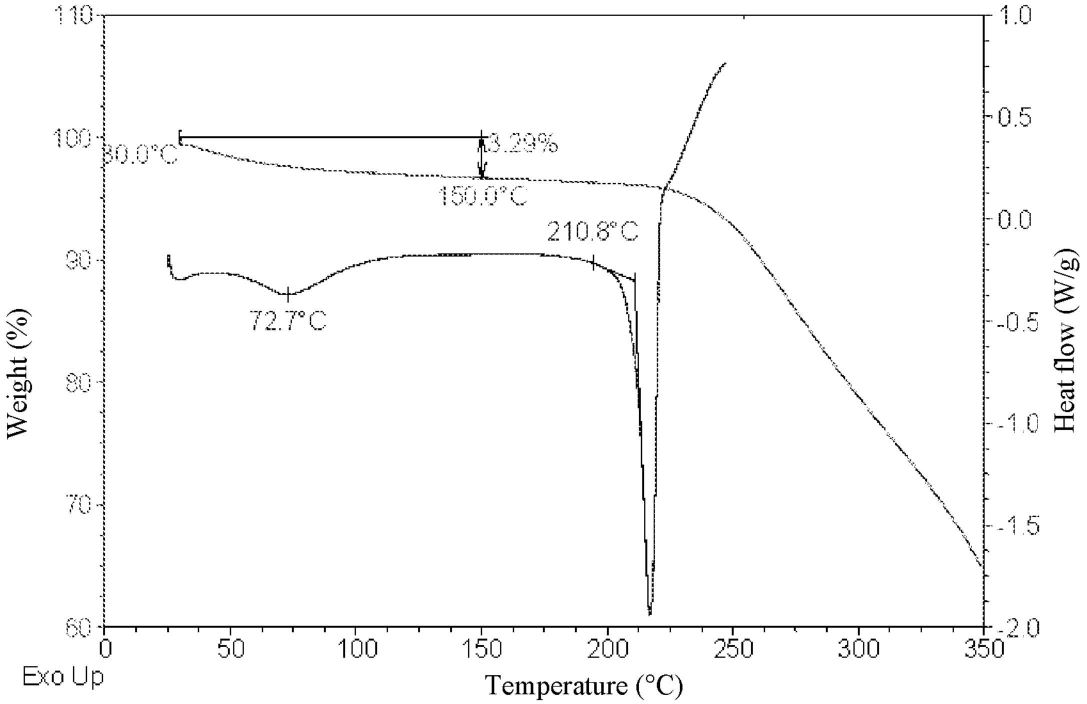
FIG. 33 is a TGA/DSC pattern of the crystal form A of p-toluenesulfonate of the compound of formula (I)
Figure 34:
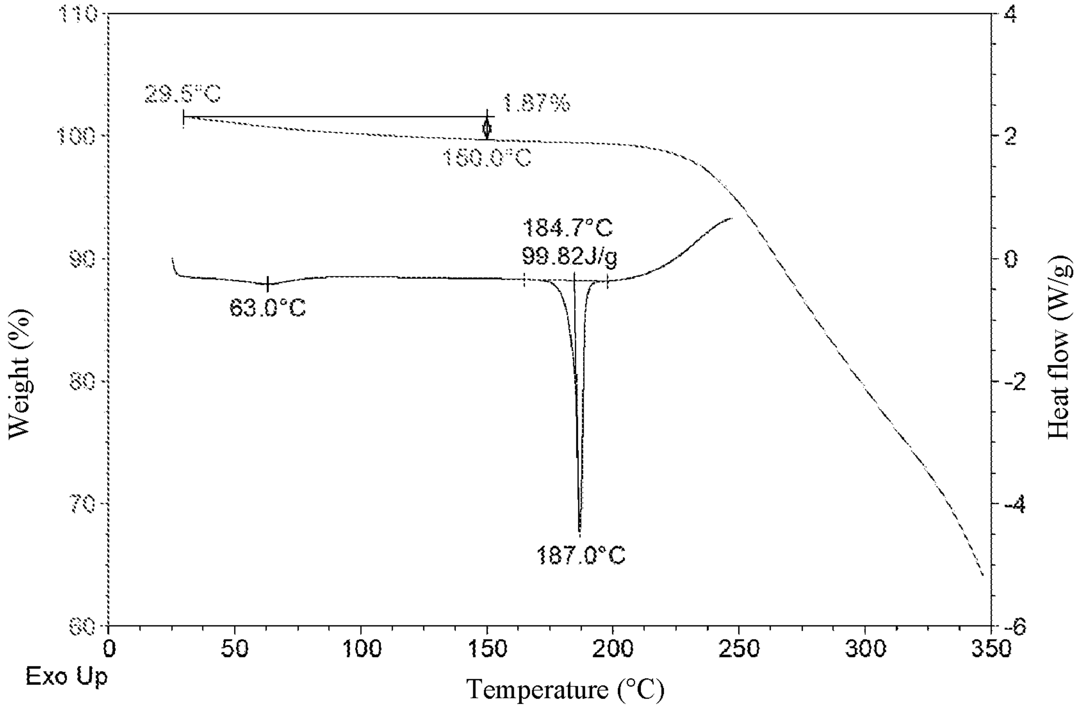
FIG. 34 is a TGA/DSC pattern of the crystal form A of benzenesulfonate of the compound of formula (I)
Figure 35:
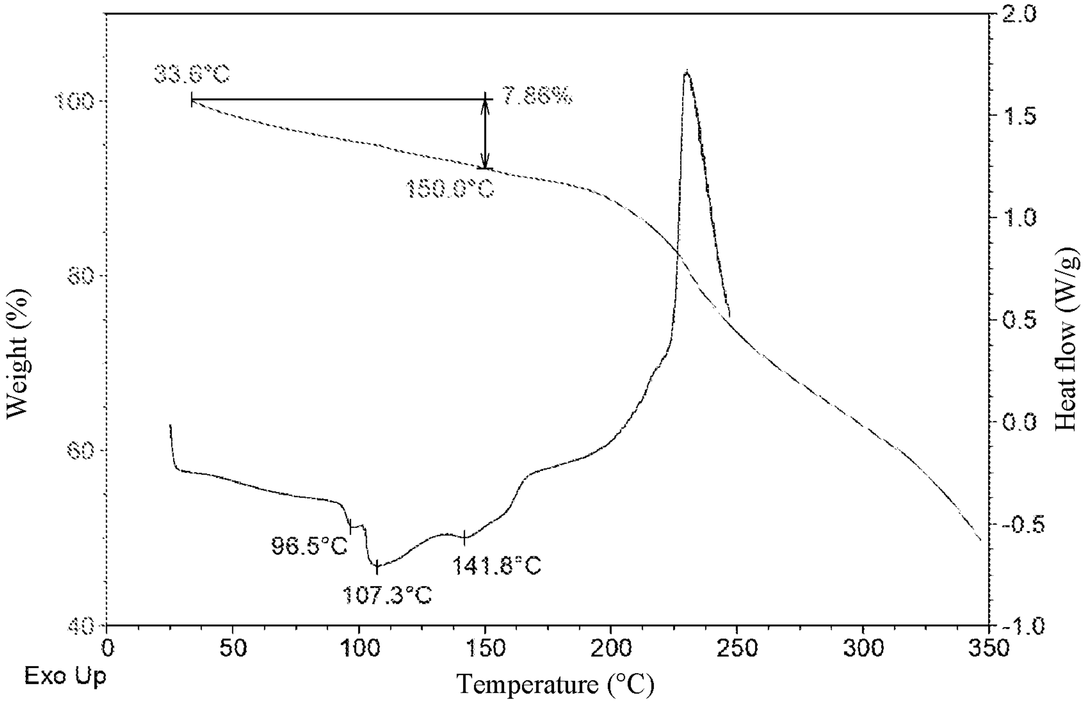
FIG. 35 is a TGA/DSC pattern of the crystal form A of hydrobromide of the compound of formula (I)
Figure 36:
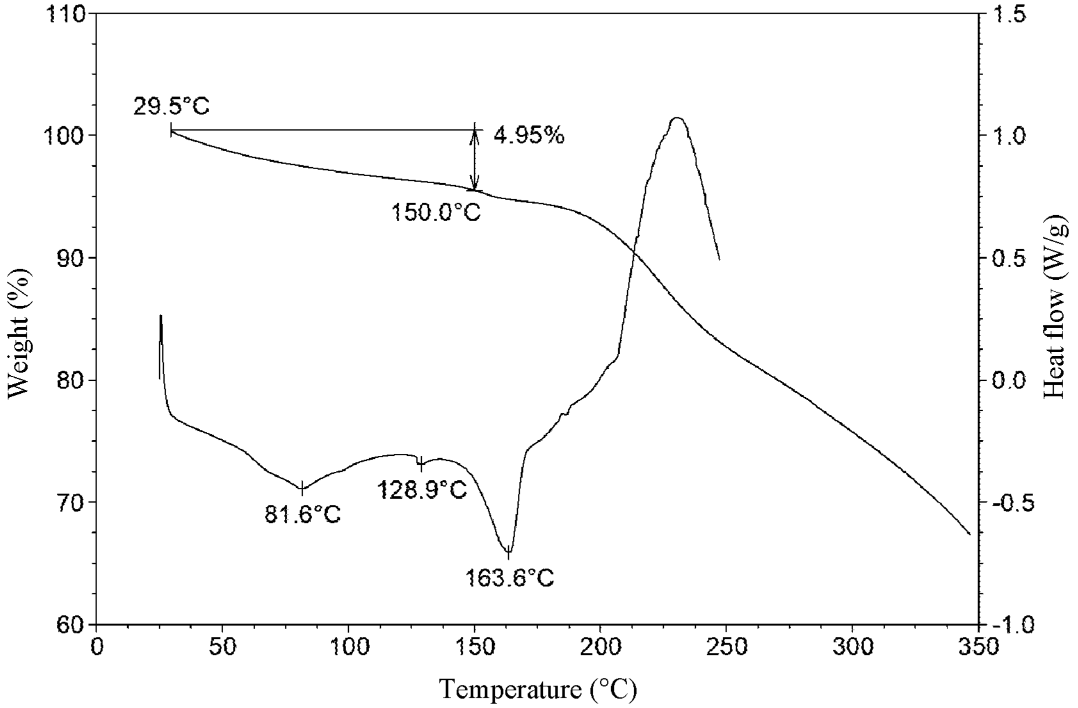
FIG. 36 is a TGA/DSC pattern of the crystal form B of hydrobromide of the compound of formula (I)
Figure 37:
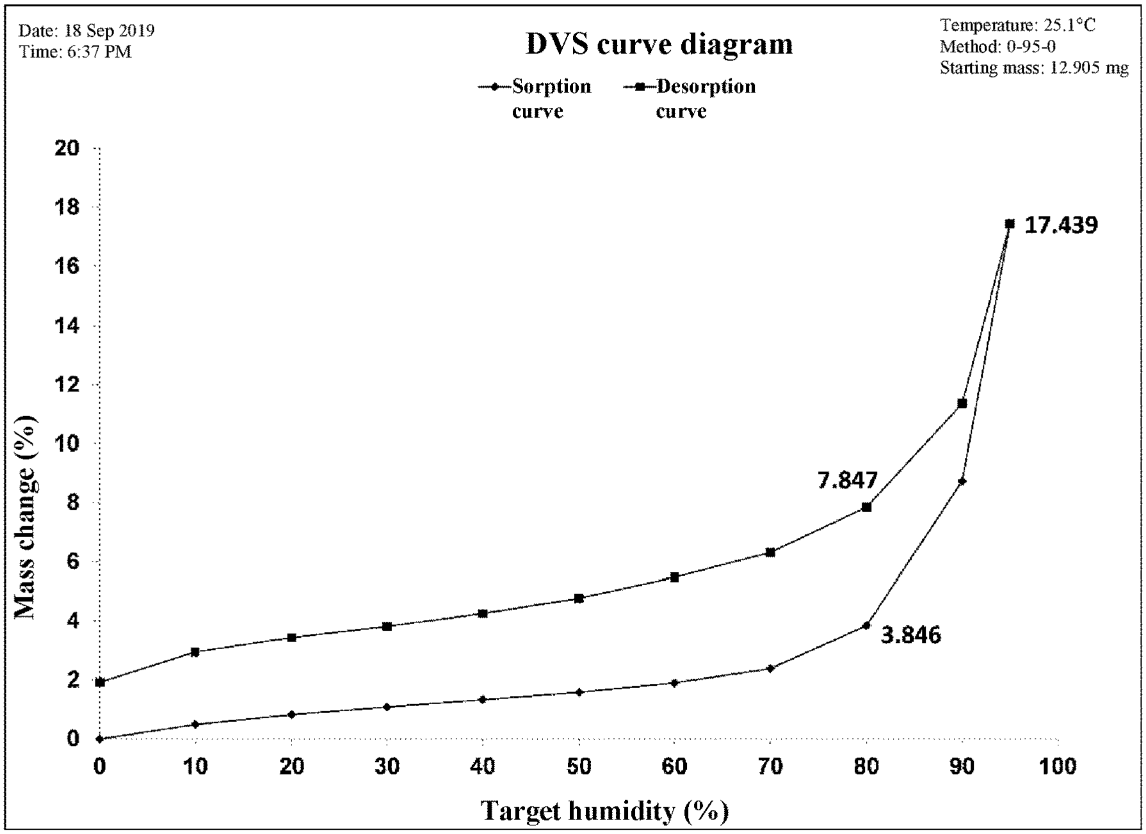
FIG. 37 is a DVS pattern of the crystal form A of hydrochloride of the compound of formula (I)
Figure 38:
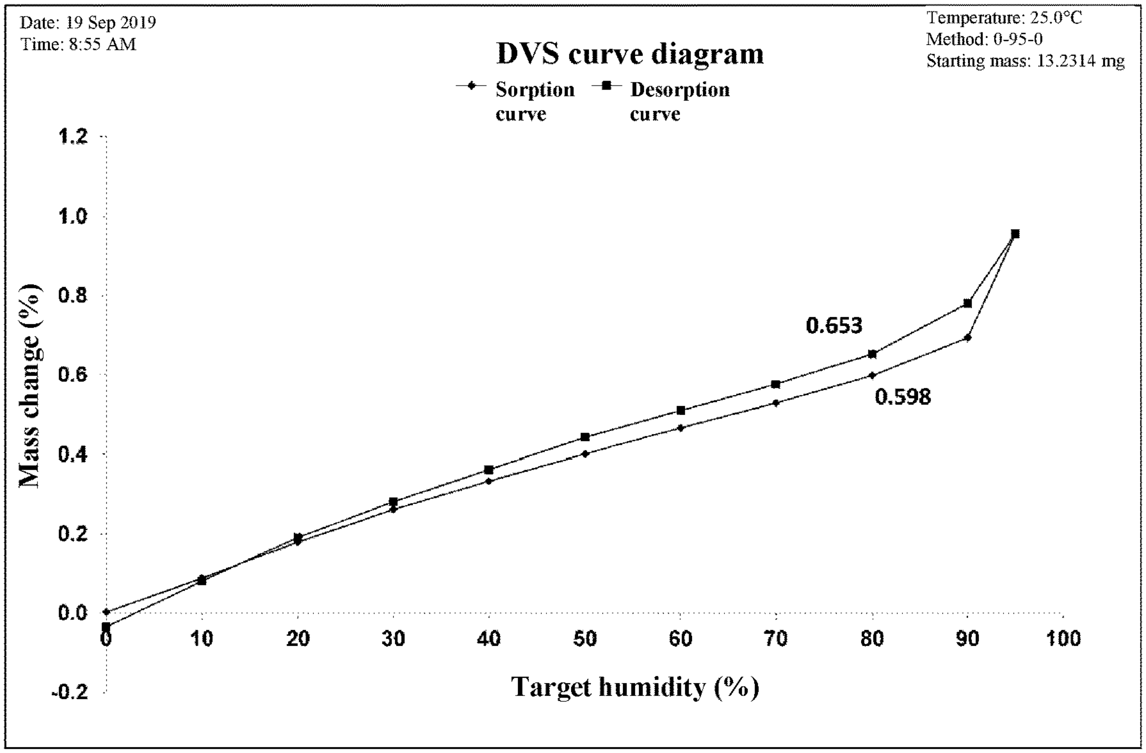
FIG. 38 is a DVS pattern of the crystal form A of fumarate of the compound of formula (I)
Figure 39:
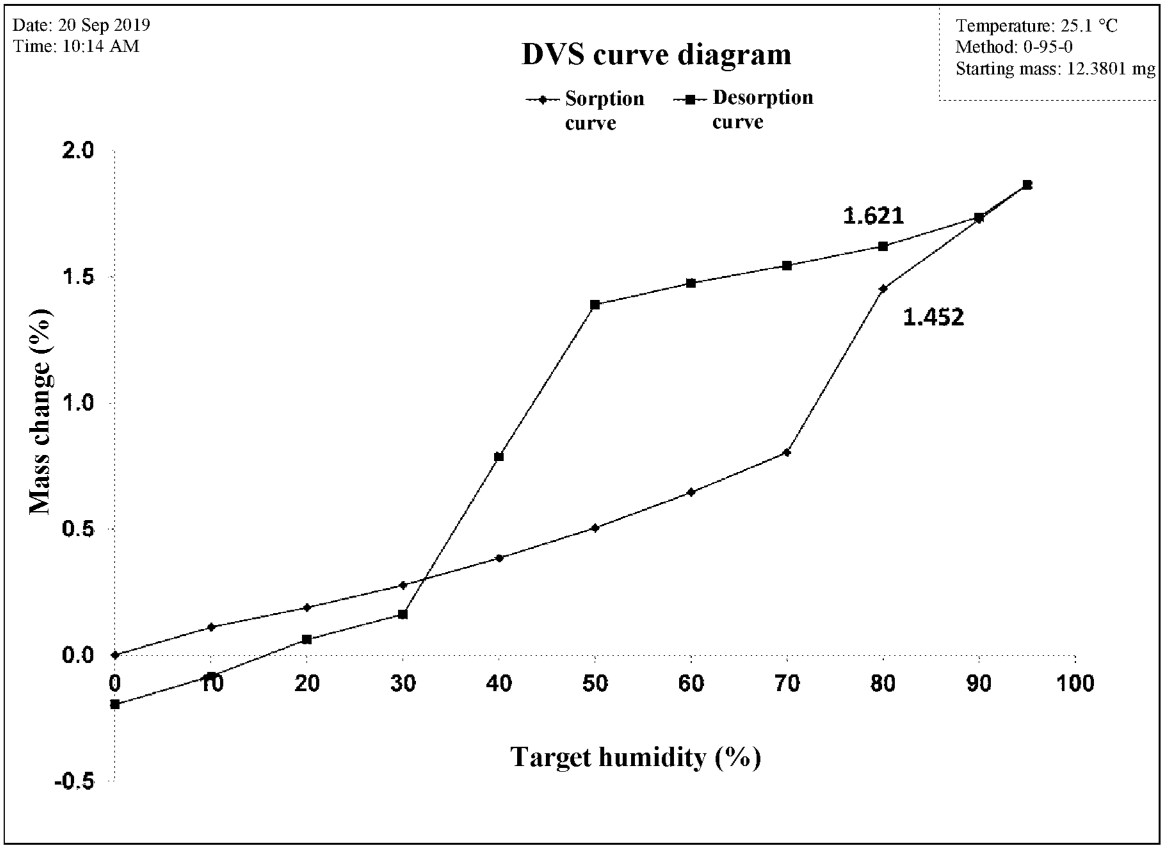
FIG. 39 is a DVS pattern of the crystal form A of benzenesulfonate of the compound of formula (I)

The crystal form A of benzenesulfonate of the compound of formula (I) was used as a starting sample, and 100 polymorph screening tests under different conditions were set. The screening method comprises the following steps: adding an anti-solvent, slowly volatilizing, slowly cooling, suspending and stirring (room temperature and 50° C.), circularly heating and cooling, gas-solid permeation, gas-liquid diffusion, inducing and grinding a high polymer. From the X-ray powder diffraction (XRPD) results of the isolated solid, only one polymorph of benzenesulfonate, i.e., the starting form A, was found. A partial evaluation was completed in the salt form screening stage, so only solid stability evaluation at 60° C. for 24 h was performed. The results were summarized in Table 22-1, and the XRPD results are shown in FIG. 19, showing that the crystal form A of benzenesulfonate of compound A did not show a significant purity decrease or crystal form transformation at 60° C. after 24 h.

TABLE 22-1

Summary of solid stability evaluation of the crystal form A of benzenesulfonate of the compound of formula (I)

| Starting sample | Condition | Time point | Purity (area %) | Purity/ initial purity (%) | Crystal form change |
|---|---|---|---|---|---|
| Crystal form A of benzenesulfonate | Starting | — | 98.18 | — | — |
| | 60° C. | 24 h | 98.23 | 100.0 | No |

The compound of formula (I) used in the following Test Examples is the compound of formula (I) prepared in Example 1 above, and the control compound used has the following structure:

Control compound

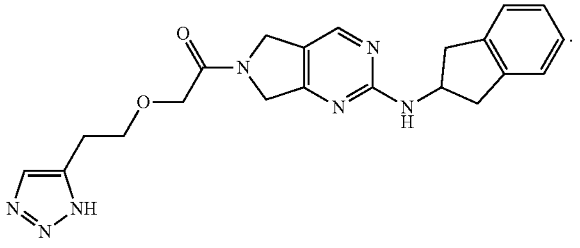

The control compound is synthesized with reference to Patent Application No. WO2014110000A1, and has a HPLC purity of 99.88%.

Test Example 1: Autotaxin (ATX) Enzymatic Activity Inhibition Assay

The inhibitory activity of the compound against the Autotaxin enzyme was detected using the Autotaxin Inhibitor Screening Assay Kit (Cayman, 700580). The compound to be tested was first prepared into 10 mM stock solution in DMSO solvent, and then serially diluted into 8 concentrations of compound with DMSO. Subsequently, 8 concentrations of compound were diluted to 19× compound working solution (with DMSO content of 1.9%) with an Autotaxin Assay buffer (1×) provided in the kit. Autotaxin Assay Reagent (10×) was taken out and diluted 10-fold with Autotaxin Assay Buffer (1×). The Autotaxin Substrate was taken out, and added with 1.2 mL of Autotaxin Assay Buffer (1×) for dissolving. The mixture was mixed well and then let stand at room temperature. In a 96-well plate, 150 μL of Autotaxin Assay Buffer (1×), 10 μL of diluted 19× compound working solution, 10 μL of Autotaxin Assay Reagent (1×), 20 μL of dissolved Autotaxin Substrate were added into wells at each concentration, and then the mixture was mixed well, incubated at 37° C. on a constant-temperature shaking shaker, and incubated in the dark for 30 min. The 96-well plate was taken out and placed on a microplate reader to read OD405; the results of the experiment were inputted to GraphPad Prism software and the $IC_{50}$ for each compound was calculated by fitting data.

TABLE 16-1

Results of the inhibitory activity of test compound against ATX enzymatic activity

| Test compound | $IC_{50}$ (nM) |
|---|---|
| Control compound | 2.60 |
| Compound of formula (I) | 1.59 |

The experimental results show that the compound of formula (I) has good inhibitory activity against ATX enzyme and can effectively inhibit ATX enzymatic activity.

Test Example 2: Stability Assay of Human Liver Microsome

The stability of human liver microsome was detected by in vitro co-incubation of compounds with human liver microsomes. Test compounds were first prepared as 10 mM stock solutions in DMSO solvent, followed by dilution of the compounds to 0.5 mM using acetonitrile. Human liver microsomes (Corning) were diluted with PBS to form a microsome/buffer solution, and 0.5 mM compound was diluted with this solution to form a working solution with a compound concentration of 1.5 μM and a human liver microsome concentration of 0.75 mg/mL. The deep-well plate was taken, L of the working solution was added to each well, then 15 μL of pre-warmed 6 mM NADPH solution was added to the plate to start the reaction, and the plate was incubated at 37° C. Reactions were terminated by adding 135 μL of acetonitrile to the corresponding wells at 0, 5, 15, 30, and 45 min of incubation. After the reaction was terminated with acetonitrile at the last 45 min time point, the deep-well plate was vortexed for 10 min (600 rpm/min) and then centrifuged for 15 min. The supernatant was taken after centrifugation, and added with purified water at a ratio of 1:1 for LC-MS/MS detection to obtain the ratio of peak area of compound to peak area of internal standard at each time point. The peak area ratios of the compounds at 5, 15, 30, and 45 min were compared with the peak area ratio thereof at 0 min, and the remaining percentage of compounds at each time point was calculated. $T_{1/2}$ was calculated using Excel.

TABLE 16-2

Results of stability assay of human liver microsome

| Compound | Remaining percentage of compound after 30 min of incubation (%) | $T_{1/2}$ (min) |
|---|---|---|
| Control compound | 41.2 | 24.1 |
| Compound of formula (I) | 63.7 | 53.6 |

Compared with the control compound, the compound of formula (I) according to the present disclosure shows more excellent liver metabolic stability, slower metabolization in a human body and higher exposure. Moreover, the compound of formula (I) of the present disclosure has $T_{1/2}$ of the liver microsome stability better than that of the control compound, and even can be more than 2 times that of the control compound, so that the clinical administration dose and the administration frequency can be reduced, the toxic and side effects of clinical administration can be reduced, and the clinical compliance can be improved.

Test Example 3: Inhibitory Effect of the Compound on hERG Detected by Automated Electrophysiological Patch Clamp QPatch Inhibitory effect of the compound on hERG was detected using automated electrophysiological patch clamp QPatch. The cells used in this assay were CHO cell lines (supplied by Sophion Bioscience, Denmark) transfected with hERG cDNA and stably expressing hERG channel at cell passage number of P24. The cells were cultured in a medium containing the following components (all purchased from Invitrogen): ham's F12 medium, 10% (v/v) inactivated fetal bovine serum, 100 μg/mL hygromycin B and 100 μg/mL Geneticin. CHO hERG cells were grown in a culture dish containing the above culture solution and cultured in an incubator containing 5% $CO_2$ at 37° C.

Extracellular buffer (2 mM $CaCl_2$, 1 mM $MgCl_2$, 4 mM KCl, 145 mM NaCl, 10 mM Glucose, 10 mM HEPES, pH: about 7.4, osmotic pressure: about 305 mOsm) and intracellular buffer (5.374 mM $CaCl_2$, 1.75 mM $MgCl_2$, 120 mM KCl, 10 mM HEPES, 5 mM EGTA, 4 mM Na-ATP, pH: about 7.25, osmotic pressure: about 295 mOsm) were prepared.

The compounds to be tested were prepared as 10 mM stock solutions in DMSO solvent, and compounds were diluted to 3, 1, 0.3, 0.1 mM in DMSO, and then diluted to 30, 10, 3, 1, 0.3 and 0.1 μM using extracellular buffer, except that the final concentration of DMSO in 30 μM compound was 0.3%, and the final concentration of DMSO in other concentrations of compound solutions was 0.1%. CHO hERG cells were digested and resuspended, and then introduced into an automated QPatch system (Sophion, Denmark) for testing according to the following preset program.

After the membrane-rupture whole-cell configuration was achieved at the initial stage, the whole-cell current was recorded at room temperature (about 25° C.), the cells were recorded for at least 120 s to stabilize, and stable cells were selected for assay. Throughout the assay, the cells were clamped at a voltage of −80 mV, depolarized to +20 mV to activate the hERG potassium channel, and clamped to −50 mV after 2.5 s to eliminate inactivation and generate an outward tail current. The tail current peak value was used as the magnitude of the hERG current. The voltage pattern described above was applied to the cells every 15 s for electrophysiological assay. The extracellular buffer containing 0.1% dimethylsulfoxide (solvent) was added to the cells, a baseline was established, and the current was allowed to stabilize for 3 min. The cells were kept in the test environment after the compound solution was added until the effect of the compound reached steady state or 4 minutes limit. In the test experiments of different concentration gradients of the compound, the compound was added to the clamped cells from low concentration to high concentration. After the compound test was completed, the cells were washed with the extracellular buffer until the current returned to a steady state.

The assay data were analyzed by Qpatch analysis software supplied by Sophion, Excel, Graphpad Prism and the like.

TABLE 16-3

Results of inhibitory effect of the compound on hERG

| Compound | hERG $IC_{50}$ (μM) | hERG $IC_{50}$/ATX $IC_{50}$ |
|---|---|---|
| Control compound | 6.69 | 6.69/2.60 = 2.6 |
| Compound of formula (I) | 9.48 | 9.48/1.59 = 6.0 |

Compared with the control compound, the compound of formula (I) according to the present disclosure shows weaker inhibition activity against hERG. According to the $IC_{50}$ value of inhibition of the compound against ATX enzymatic activity, the compound of formula (I) shows a better safety window on hERG inhibition, and has significant cardiac safety advantage.

Test Example 4: Thermodynamic Solubility Assay

Phosphate buffered saline (PBS) at pH 7.4, FeSSIF solution at pH 5.8 (containing 10 mM sodium taurocholate, 2 mM lecithin, 81.65 mM sodium hydroxide, 125.5 mM sodium chloride, 0.8 mM sodium oleate, 5 mM glycerol monooleate and 55.02 mM maleic acid), and FaSSGF solution at pH 1.6 (1 L solution containing 80 μM sodium taurocholate, 20 μM lecithin, 0.1 g pepsin and 34.2 mM sodium chloride) were prepared.

The compounds were weighed out accurately, added to the prepared phosphate buffered saline at pH 7.4, FeSSIF solution at pH 5.8 and FaSSGF solution at pH 1.6 to prepare a solution at a concentration of 4 mg/mL, and the prepared solution was shaken at 1000 rpm for 1 h, and then incubated overnight at room temperature. The incubated solution was centrifuged at 12000 rpm for 10 min to remove undissolved particles, and the supernatant was transferred to a new centrifuge tube. After the supernatant was diluted properly, the supernatant was added with an acetonitrile solution containing an internal standard, and quantified by adopting a standard curve prepared by the same matrix.

TABLE 16-4

Results of thermodynamic solubility assay

| | Solubility (mg/mL) | | |
|---|---|---|---|
| Test compound | FaSSGF (pH 1.6) | FeSSIF (pH 5.8) | PBS (pH 7.4) |
| Control compound | 66.5 | 18.3 | 6.3 |
| Compound of formula (I) | 1037 | 260 | 107 |

The experimental results show that the control compound has relatively poor solubility, and the gastrointestinal absorption is expected to be relatively poor, so that the control compound is not beneficial to be developed into oral drugs. Compared with the control compound, the compound of formula (I) according to the present disclosure has significantly improved thermodynamic solubility under simulated gastric fluid, simulated intestinal fluid and neutral conditions, so that the absorption degree of the compound in the intestinal tract of a human body is expected to be greatly improved, the exposure amount of oral administration is higher, the clinical administration dosage can be reduced, and the clinical compliance is improved.

Test Example 5: Pharmacokinetic Assay

In vivo pharmacokinetic assay in rats was performed, wherein the used rats were 6 male SD rats weighing 180-240 g and fasted overnight. 3 rats were taken and orally intragastrically administered with 10 mg/kg of the compound, and blood was collected before administration and at 15 min, 30 min and 1 h, 2 h, 4 h, 8 h, 24 h after administration. Another 3 rats were taken and intravenously injected with 1 mg/kg of the compound, and blood was collected before administration and at 5 min, 15 min, 30 min and 1 h, 2 h, 4 h, 8 h, 24 h after administration. Blood samples were centrifuged at 8000 rpm for 6 min at 4° C., and plasma was collected and stored at −20° C. The plasma at each time point was taken and added with 3-5 times of acetonitrile solution containing the internal standard for mixing, and the mixed solution was subjected to vortex mixing for 1 min, and centrifuging at 4° C. for 10 min at 13000 rpm. The supernatant was taken and added with 3 times of water for mixing. A proper amount of the mixed solution was taken for LC-MS/MS analysis. The major pharmacokinetic parameters were analyzed using WinNonlin 7.0 software and a non-compartmental model.

In vivo pharmacokinetic assay in mice was performed, wherein the used mice were 18 male ICR mice weighing 20-25 g and fasted overnight. 9 mice were taken and orally intragastrically administered with 10 mg/kg of the compound, 3 mice were taken at each blood collection time point, and a total of 9 mice were subjected to alternate blood collection; other 9 mice were taken and intravenously injected with 1 mg/kg of the compound, 3 mice were taken at each blood collection time point, and a total of 9 mice were subjected to alternate blood collection. The rest of the procedure was performed in the same manner as in the pharmacokinetic assay in rats.

TABLE 16-5

Results of in vivo pharmacokinetic assay in mice

| | In vivo pharmacokinetic parameters in mice | | | | | | | |
|---|---|---|---|---|---|---|---|---|
| | Intravenous injection (1 mg/kg) | | | | Oral intragastric administration (10 mg/kg) | | | |
| Test compound | CL (L/h/kg) | Vz (L/kg) | AUC0-t (h*ng/mL) | $T_{1/2}$ (h) | Cmax (ng/mL) | Tmax (hr) | AUC0-t (h*ng/mL) | $T_{1/2}$ (h) |
| Control compound | 3.45 | 1.67 | 290 | 0.34 | 2042 | 0.25 | 2902 | 0.83 |
| Compound of formula (I) | 1.60 | 0.88 | 626 | 0.38 | 6357 | 0.25 | 6368 | 0.87 |

TABLE 16-6

Results of in vivo pharmacokinetic assay in rats

| | In vivo pharmacokinetic parameters in rats | | | | | | | |
|---|---|---|---|---|---|---|---|---|
| | Intravenous injection (1 mg/kg) | | | | Oral intragastric administration (10 mg/kg) | | | |
| Test compound | CL (L/h/kg) | Vz (L/kg) | AUC0-t (h*ng/mL) | $T_{1/2}$ (h) | Cmax (ng/mL) | Tmax (hr) | AUC0-t (h*ng/mL) | $T_{1/2}$ (h) |
| Control compound | 1.76 | 1.12 | 580 | 0.45 | 2591 | 0.42 | 4874 | 1.31 |
| Compound of formula (I) | 0.28 | 0.21 | 3648 | 0.50 | 15844 | 0.33 | 20675 | 2.56 |

The experimental results show that the compound of formula (I) according to the present disclosure shows superior pharmacokinetic properties compared with the control compound. In particular, the compound of formula (I) according to the present disclosure has a lower clearance (CL) in rats, which is about ⅙ of that of the control compound, indicating that the compound of formula (I) is stable in vivo and that the $C_{max}$ and $AUC_{0-t}$ of oral administration can reach 6.1 times and 4.2 times of the control compound, respectively.

Test Example 6: Inhibition Assay of ATX Enzymatic Activity in Human Plasma

Whole blood from healthy volunteers was collected and anticoagulated with heparin. The blood collection tubes were centrifuged at 3000 rpm for 10 min, and plasma was taken and stored at −80° C. for later use.

The compounds were serially diluted with DMSO according to the standard concentration requirements, and then 3 μL of the compound was taken and added to a 96-well plate. 147 μL of PBS was added to each well containing 3 μL of the compound, and the mixed solution was mixed well, and then 50 μL of the mixed solution was taken out and added to a new 96-well plate. The human plasma was taken out of −80° C. refrigerator and thawed by rapid shaking in a 37° C. water bath, and 50 μL of human plasma was added to a 96-well plate containing 50 μL of diluted compounds (the final system was 1% DMSO). The group containing no compound was set as the positive group. The 96-well plate was shaken and mixed well, and incubated at 37° C. for 3 h; a blank group was also set, and the plasma of the blank group was stored at −80° C.; and the function of the blank group was to determine the baseline concentration of endogenous LPA.

After the incubation, the blank group was thawed on ice and transferred to the incubation plate. Excess acetonitrile containing the internal standard LPA17:0 was added to the incubation plate to precipitate plasma proteins. After vortex centrifugation, the supernatant was taken and diluted. The peak areas of LPA18:2 and internal standard LPA17:0 were detected by LC-MSMS mass spectrometry.

The peak area ratio of LPA18:2 to internal standard LPA17:0 was calculated, and the generation inhibition rate of LPA18:2 was calculated according to the following formula:

Inhibition rate (%)=100−(different concentrations of compound group−blank group)/(positive group−blank group)×100

According to the inhibition rate of different concentrations of the compound, the $IC_{50}$ values of the compound were calculated for inhibition of ATX enzymatic activity in human plasma.

TABLE 16-7

Results of the inhibitory activity of test compound against ATX enzymatic activity in human plasma

| Test compound | $IC_{50}$ (nM) |
|---|---|
| Control compound | 13.0 |
| Compound of formula (I) | 4.7 |

The experimental results show that the compound of formula (I) has good inhibitory activity against ATX enzyme in human plasma, can effectively inhibit ATX enzymatic activity, and is significantly superior to the control compound.

Test Example 7: Bleomycin-Induced IPF Model in Rats

The bleomycin-induced IPF model (idiopathic pulmonary fibrosis model) was performed at a dose of 5 U/kg using male BN rats weighing 180-240 g. Animals were randomly grouped after the modeling into a solvent control group, a GLPG-1690 group (a clinical III-stage compound from Galapagos), a control compound group and a compound of formula (I). The oral intragastric administration was performed twice a day on the second day after the modeling. The administration group was given a dose of 30 mg/kg at one time, and the vehicle control group was given blank vehicle for 21 consecutive days.

During dosing, body weights were weighed every three days. On the 21st day of administration, bronchoalveolar lavage was performed 2 h after the first administration, the inflammatory cells in the lavage fluid were counted, and the relevant biomarkers in the lavage fluid supernatant were detected; after lavage, the left lung of the rat was harvested for fixation, and Masson's trichrome staining was used for pathological scoring of fibrosis and the remaining lung lobes were cryopreserved. The bronchoalveolar lavage fluid supernatant and freshly cryopreserved lung tissue of compound 3 group were taken, and the TGF-β1 protein content and total protein amount were detected by ELISA method, and the amount of TGF-β1 per mg of total protein was calculated.

Figure 43:
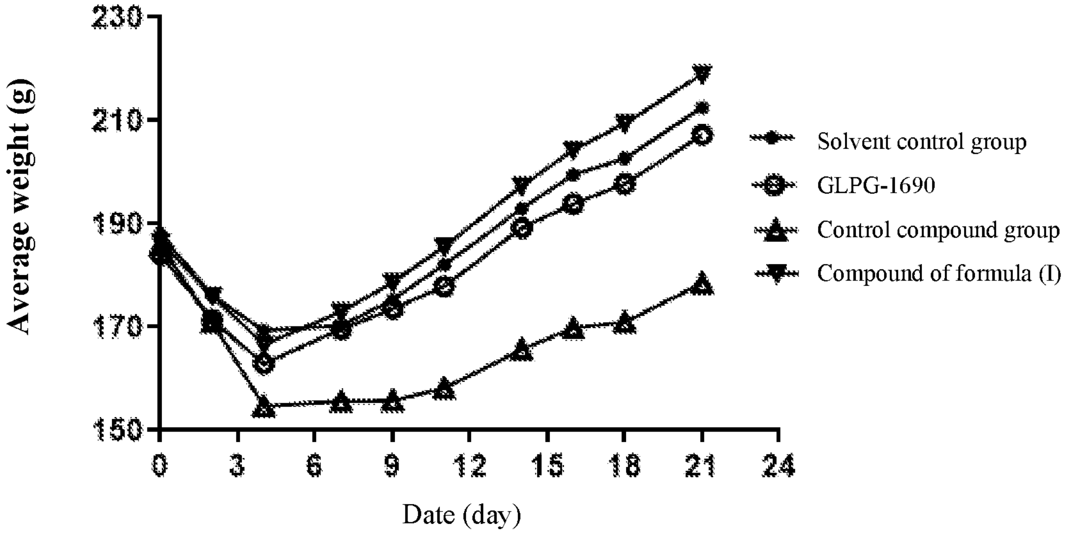
FIG. 43 is a graph showing the change in body weight of animals after administration according to Test Example 7 of the present disclosure.
Figure 44:
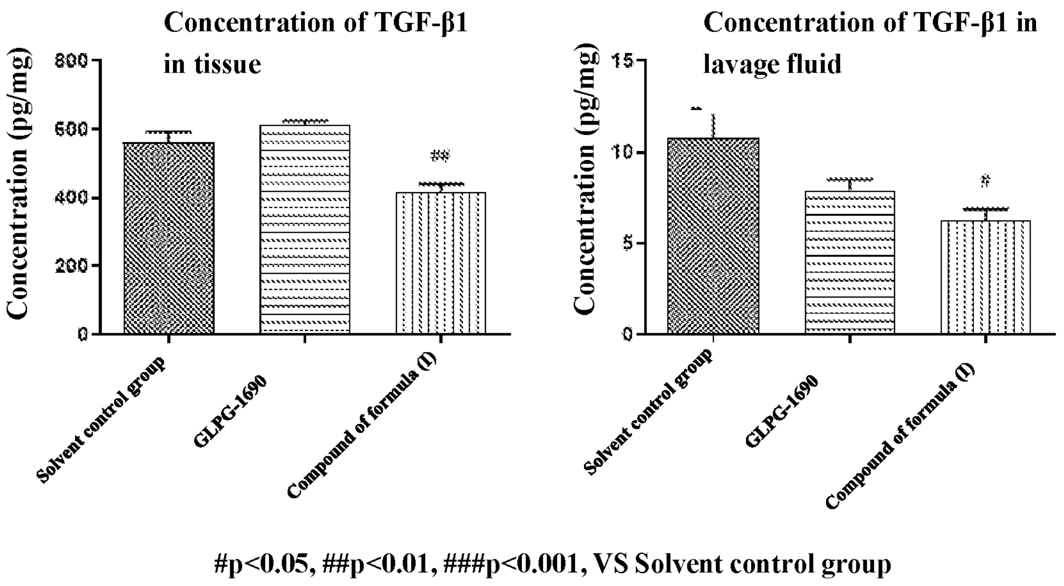
FIG. 44 is a graph showing the change in the TGF-β1 content in lung tissue and bronchoalveolar lavage fluid after administration according to Test Example 7 of the present disclosure.

The experimental results show that the weight loss of the animals of the compound of formula (I) is significantly less than that of the control compound group, and the safety of the compound of formula (1) is better (the results are shown in FIG. 43); the content of TGF-β1 in the bronchoalveolar lavage fluid supernatant and freshly cryopreserved lung tissue of the compound of formula (I) is significantly lower than that of the vehicle control group, and the compound of formula (I) has significant anti-fibrosis effects (results are shown in FIG. 44).

Test Example 8: Pharmacokinetic Assay (Crystal Form)

In vivo pharmacokinetic assay in mice was performed, wherein the used mice were 9 male ICR mice weighing 20-25 g and fasted overnight. 9 mice were taken and orally intragastrically administered with 10 mg/kg of the compound. Blood was collected before administration and at 15 min, 30 min and 1 h, 2 h, 4 h, 8 h, 12 h, 24 h after administration, with 9 mice alternately and 3 mice at each blood collection time point. Blood samples were centrifuged at 8000 rpm for 6 min at 4° C., and plasma was collected and stored at −20° C. The plasma at each time point was taken and added with 3-5 times of acetonitrile solution containing the internal standard for mixing, and the mixed solution was subjected to vortex mixing for 1 min, and centrifuging at 4° C. for 10 min at 13000 rpm. The supernatant was taken and added with 3 times of water for mixing. A proper amount of the mixed solution was taken for LC-MS/MS analysis. The major pharmacokinetic parameters were analyzed using WinNonlin 7.0 software and a non-compartmental model.

TABLE 16-8

Results of in vivo pharmacokinetic assay in mice

| | Oral intragastric administration (10 mg/kg) | | | |
|---|---|---|---|---|
| Test compound | Cmax (ng/mL) | Tmax (hr) | AUC0-t (h*ng/mL) | $T_{1/2}$ (h) |
| Control compound | 2042 | 0.25 | 2902 | 0.83 |
| Crystal form A of benzenesulfonate | 6600 | 0.5 | 7430 | 1.19 |

The experimental results show that the crystal form A of benzenesulfonate of the compound of formula (I) according to the present disclosure shows superior pharmacokinetic properties compared with the control compound.

The embodiments of the present disclosure have been described above. However, the present disclosure is not limited the above embodiments. Any modification, equivalent, improvement and the like made without departing from the spirit and principle of the present disclosure shall fall within the protection scope of the present disclosure.

The invention claimed is:

1. A crystal form of a salt of a compound of formula (I), (I)

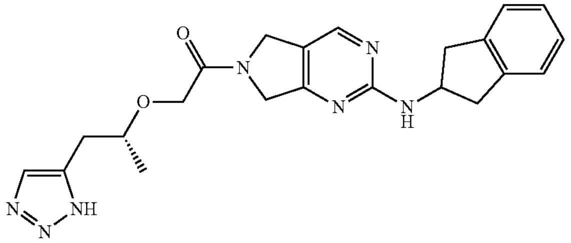

(R)-2-((1-(1H-1,2,3-triazol-5-yl)propan-2-yl)oxy)-1-(2-((2,3-dihydro-1 H-inden-2-yl)amino)-5,7-dihydro-6H-pyrrolo[3,4-d]pyrimidin-6-yl)ethan-1-one wherein the crystal form is a crystal form A of hydrochloride of the compound of formula (I), wherein the crystal form A of hydrochloride has characteristic peaks in an X-ray powder diffraction pattern using Cu-Kα radiation at the following 2θ angles: 7.48±0.20°, 13.13±0.20°, 16.47±0.20° and 23.94±0.20°;

wherein the crystal form is a crystal form A of sulfate of the compound of formula (I), wherein the crystal form A of sulfate has characteristic peaks in an X-ray powder diffraction pattern using Cu-Kα radiation at the following 2θ angles: 5.49±0.20°, 15.88±0.20°, 17.48±0.20° and 22.40±0.20°;

wherein the crystal form is a crystal form A of maleate of the compound of formula (I), wherein the crystal form A of maleate has characteristic peaks in an X-ray powder diffraction pattern using Cu-Kα radiation at the following 2θ angles: 4.43±0.20°, 13.86±0.20°, 14.41±0.20°, 15.00±0.20°, 22.07±0.20°, 22.65±0.20°, 25.58±0.20° and 27.34±0.20°;

wherein the crystal form is a crystal form A of phosphate of the compound of formula (I), wherein the crystal form A of phosphate has characteristic peaks in an X-ray powder diffraction pattern using Cu-Kα radiation at the following 2θ angles: 5.08±0.20°, 15.93±0.20°, 24.37±0.20° and 25.19±0.20°;

wherein the crystal form is a crystal form A of tartrate of the compound of formula (I), wherein the crystal form A of tartrate has characteristic peaks in an X-ray powder diffraction pattern using Cu-Kα radiation at the following 2θ angles: 5.00±0.20° and 15.88±0.20°;

wherein the crystal form is a crystal form B of tartrate of the compound of formula (I), wherein the crystal form B of tartrate has characteristic peaks in an X-ray powder diffraction pattern using Cu-Kα radiation at the following 2θ angles: 5.24±0.20° and 23.94±0.20°;

wherein the crystal form is a crystal form C of tartrate of the compound of formula (I), wherein the crystal form C of tartrate has characteristic peaks in an X-ray powder diffraction pattern using Cu-Kα radiation at the following 2θ angles: 4.60±0.20°, 16.15±0.20° and 18.13±0.20°;

wherein the crystal form is a crystal form A of fumarate of the compound of formula (I), wherein the crystal form A of fumarate has characteristic peaks in an X-ray powder diffraction pattern using Cu-Kα radiation at the following 2θ angles: 9.52±0.20°, 13.29±0.20°, 14.92±0.20° and 25.23±0.20°;

wherein the crystal form is a crystal form A of citrate of the compound of formula (I), wherein the crystal form A of citrate has characteristic peaks in an X-ray powder diffraction pattern using Cu-Kα radiation at the following 2θ angles: 4.96±0.20° and 15.76±0.20°;

wherein the crystal form is a crystal form A of glycolate of the compound of formula (I), wherein the crystal form A of glycolate has characteristic peaks in an X-ray powder diffraction pattern using Cu-Kα radiation at the following 2θ angles: 5.26±0.20°, 7.27±0.20°, 14.12±0.20°, 16.02±0.20° and 24.11±0.20°;

wherein the crystal form is a crystal form A of succinate of the compound of formula (I), wherein the crystal form A of succinate has characteristic peaks in an X-ray powder diffraction pattern using Cu-Kα radiation at the following 2θ angles: 5.26±0.20°, 14.00±0.20°, 15.76±0.20°, 21.07±0.20°, 22.00±0.20° and 27.08±0.20°;

wherein the crystal form is a crystal form B of succinate of the compound of formula (I), wherein the crystal form B of succinate has characteristic peaks in an X-ray powder diffraction pattern using Cu-Kα radiation at the following 2θ angles: 9.54±0.20°, 12.60±0.20°, 14.91±0.20°, 19.17±0.20°, 21.02±0.20° and 24.88±0.20°;

wherein the crystal form is a crystal form B of adipate of the compound of formula (I), wherein the crystal form B of adipate has characteristic peaks in an X-ray powder diffraction pattern using Cu-Kα radiation at the following 2θ angles: 4.98±0.20°, 10.69±0.20°, 13.88±0.20°, 21.41±0.20°, 24.97±0.20° and 26.15±0.20°;

wherein the crystal form is a crystal form A of sebacate of the compound of formula (I), wherein the crystal form A of sebacate has characteristic peaks in an X-ray powder diffraction pattern using Cu-Kα radiation at the following 2θ angles: 4.57±0.20°, 9.27±0.20°, 11.20±0.20°, 14.40±0.20°, 20.16±0.20°, 24.63±0.20° and 26.73±0.20°;

wherein the crystal form is a crystal form A of p-toluenesulfonate of the compound of formula (I), wherein the crystal form A of p-toluenesulfonate has characteristic peaks in an X-ray powder diffraction pattern using Cu-Kα radiation at the following 2θ angles: 6.04±0.20°, 8.59±0.20°, 14.27±0.20°, 17.14±0.20° and 25.29±0.20°;

wherein the crystal form is a crystal form A of benzenesulfonate of the compound of formula (I), wherein the crystal form A of benzenesulfonate has characteristic peaks in an X-ray powder diffraction pattern using Cu-Kα radiation at the following 2θ angles: 6.16±0.20°, 8.98±0.20°, 14.22±0.20°, 16.90±0.20°, 18.31±0.20°, 20.92±0.20°, 25.11±0.20° and 26.29±0.20°;

wherein the crystal form is a crystal form A of hydrobromide of the compound of formula (I), wherein the crystal form A of hydrobromide has characteristic peaks in an X-ray powder diffraction pattern using Cu-Kα radiation at the following 2θ angles: 9.54±0.20° and 24.63±0.20°; or wherein the crystal form is a crystal form B of hydrobromide of the compound of formula (I), wherein the crystal form B of hydrobromide has characteristic peaks in an X-ray powder diffraction pattern using Cu-Kα radiation at the following 2θ angles: 9.48±0.20°, 15.89±0.20° and 23.98±0.20°.

2. The crystal form according to claim 1, wherein the crystal form A of hydrochloride has characteristic peaks in an X-ray powder diffraction pattern at the following 2θ angles: 7.48±0.20°, 13.13±0.20°, 16.47±0.20°, 18.29±0.20°, 19.89±0.20° and 23.94±0.20°;

wherein the crystal form A of sulfate has characteristic peaks in an X-ray powder diffraction pattern at the following 2θ angles: 5.49±0.20°, 6.93±0.20°, 11.08±0.20°, 15.88±0.20°, 17.48±0.20°, 20.82±0.20° and 22.40±0.20°;

wherein the crystal form A of maleate has characteristic peaks in an X-ray powder diffraction pattern at the following 2θ angles: 4.43±0.20°, 9.92±0.20°, 13.86±0.20°, 14.41±0.20°, 15.00±0.20°, 17.82±0.20°, 22.07±0.20°, 22.65±0.20°, 25.58±0.20° and 27.34±0.20°;

wherein the crystal form A of tartrate has characteristic peaks in an X-ray powder diffraction pattern at the following 2θ angles: 5.00±0.20°, 7.34±0.20°, 8.59±0.20°, 15.88±0.20°, 19.54±0.20°, 21.46±0.20°, 23.43±0.20° and 25.08±0.20°;

wherein the crystal form C of tartrate has characteristic peaks in an X-ray powder diffraction pattern at the following 2θ angles: 4.60±0.20°, 7.58±0.20°, 14.39±0.20°, 16.15±0.20°, 18.13±0.20°, 22.32±0.20°, 24.44±0.20° and 26.69±0.20°;

wherein the crystal form A of fumarate has characteristic peaks in an X-ray powder diffraction pattern at the following 2θ angles: 9.52±0.20°, 13.29±0.20°, 14.92±0.20°, 19.02±0.20°, 21.39±0.20°, 25.23±0.20° and 28.07±0.20°;

wherein the crystal form A of succinate has characteristic peaks in an X-ray powder diffraction pattern at the following 2θ angles: 5.26±0.20°, 6.99±0.20°, 7.35±0.20°, 14.00±0.20°, 15.76±0.20°, 21.07±0.20°, 22.00±0.20° and 27.08±0.20°;

wherein the crystal form B of succinate has characteristic peaks in an X-ray powder diffraction pattern at the following 2θ angles: 9.54±0.20°, 12.60±0.20°, 13.28±0.20°, 14.91±0.20°, 15.20±0.20°, 19.17±0.20°, 21.02±0.20°, 24.88±0.20° and 28.15±0.20°;

wherein the crystal form B of adipate has characteristic peaks in an X-ray powder diffraction pattern at the following 2θ angles: 4.98±0.20°, 10.69±0.20°, 13.88±0.20°, 14.28±0.20°, 20.72±0.20°, 21.41±0.20°, 24.97±0.20° and 26.15±0.20°;

wherein the crystal form A of sebacate has characteristic peaks in an X-ray powder diffraction pattern at the following 2θ angles: 4.57±0.20°, 9.27±0.20°, 11.20±0.20°, 14.40±0.20°, 14.95±0.20°, 20.16±0.20°, 20.55±0.20°, 22.95±0.20°, 23.91±0.20°, 24.63±0.20° and 26.73±0.20°;

wherein the crystal form A of p-toluenesulfonate has characteristic peaks in an X-ray powder diffraction pattern at the following 2θ angles: 6.04±0.20°, 8.59±0.20°, 14.27±0.20°, 17.14±0.20°, 20.41±0.20°, 23.68±0.20°, 25.29±0.20° and 27.65±0.20°;

wherein the crystal form A of benzenesulfonate has characteristic peaks in an X-ray powder diffraction pattern at the following 2θ angles: 6.16±0.20°, 8.98±0.20°, 14.22±0.20°, 15.67±0.20°, 16.90±0.20°, 17.55±0.20°, 18.31±0.20°, 20.34±0.20°, 20.92±0.20°, 25.11±0.20°, 26.29±0.20° and 29.24±0.20°; or wherein the crystal form B of hydrobromide has characteristic peaks in an X-ray powder diffraction pattern at the following 2θ angles: 9.48±0.20°, 15.89±0.20°, 19.40±0.20°, 23.98±0.20°, 26.55±0.20° and 28.02±0.20°.

3. The crystal form according to claim 1, wherein the crystal form A of hydrochloride has characteristic peaks in an X-ray powder diffraction pattern at the following 2θ angles: 7.48±0.20°, 13.13±0.20°, 14.86±0.20°, 16.47±0.20°, 18.29±0.20°, 19.89±0.20°, 23.94±0.20° and 26.92±0.20°;

wherein the crystal form A of maleate has characteristic peaks in an X-ray powder diffraction pattern at the following 2θ angles: 4.43±0.20°, 9.92±0.20°, 13.86±0.20°, 14.41±0.20°, 15.00±0.20°, 17.82±0.20°, 22.07±0.20°, 22.65±0.20°, 24.20±0.20°, 24.53±0.20°, 25.58±0.20°, 25.84±0.20° and 27.34±0.20°;

wherein the crystal form B of succinate has characteristic peaks in an X-ray powder diffraction pattern at the following 2θ angles: 9.54±0.20°, 12.60±0.20°, 13.28±0.20°, 14.91±0.20°, 15.20±0.20°, 19.17±0.20°, 19.77±0.20°, 21.02±0.20°, 21.44±0.20°, 24.88±0.20°, 25.22±0.20° and 28.15±0.20°;

wherein the crystal form B of adipate has characteristic peaks in an X-ray powder diffraction pattern at the following 2θ angles: 4.98±0.20°, 9.23±0.20°, 10.69±0.20°, 13.88±0.20°, 14.28±0.20°, 19.35±0.20°, 20.72±0.20°, 21.41±0.20°, 24.97±0.20° and 26.15±0.20°;

wherein the crystal form A of sebacate has characteristic peaks in an X-ray powder diffraction pattern at the following 2θ angles: 4.57±0.20°, 9.27±0.20°, 11.20±0.20°, 14.40±0.20°, 14.95±0.20°, 15.26±0.20°, 18.25±0.20°, 20.16±0.20°, 20.95±0.20°, 22.95±0.20°, 23.91±0.20°, 24.63±0.20° and 26.73±0.20°;

wherein the crystal form A of p-toluenesulfonate has characteristic peaks in an X-ray powder diffraction pattern at the following 2θ angles: 6.04±0.20°, 8.59±0.20°, 12.28±0.20°, 14.27±0.20°, 16.02±0.20°, 17.14±0.20°, 20.41±0.20°, 22.01±0.20°, 23.68±0.20°, 25.29±0.20° and 27.65±0.20°; or wherein the crystal form A of benzenesulfonate has characteristic peaks in an X-ray powder diffraction pattern at the following 2θ angles: 6.16±0.20°, 8.98±0.20°, 14.22±0.20°, 15.67±0.20°, 16.90±0.20°, 17.55±0.20°, 18.31±0.20°, 20.34±0.20°, 20.92±0.20°, 23.54±0.20°, 24.65±0.20°, 25.11±0.20°, 26.29±0.20° and 29.24±0.20°.

4. A pharmaceutical composition comprising the crystal form of the salt of the compound of formula (I) according to claim 1.

5. A method of treatment of an Autotaxin (ATX)-related disease, comprising administering to a patient in need thereof a therapeutically effective amount of the crystal form of the salt of the compound of formula (I) according to claim 1 or a pharmaceutical composition comprising the crystal form of the salt of the compound of formula (I) according to claim 1.

6. The method according to claim 5, wherein the ATX-related disease comprises at least one selected from the following: cancer, metabolic diseases, renal diseases, hepatic diseases, fibrotic diseases, interstitial lung diseases, proliferative diseases, inflammatory diseases, pain, autoimmune diseases, respiratory diseases, cardiovascular diseases, neurodegenerative diseases, dermatological disorders and abnormal angiogenesis-related diseases.

7. The method according to claim 5, wherein the ATX-related disease comprises at least one selected from the following: interstitial lung diseases, pulmonary fibrosis, hepatic fibrosis and renal fibrosis.

8. The method according to claim 5, wherein the ATX-related disease comprises idiopathic pulmonary fibrosis, type II diabetes, non-alcoholic steatohepatitis, neuropathic pain and inflammatory pain.

9. The method according to claim 5, wherein the ATX-related disease comprises osteoarthritis-related pain.

* * * * *